United States Patent [19]

Kikuchi et al.

[11] Patent Number: 5,736,550
[45] Date of Patent: Apr. 7, 1998

[54] PYRIMIDINE DERIVATIVES

[75] Inventors: Haruhiko Kikuchi; Hiroaki Satoh; Ruta Fukutomi; Kohei Inomata; Masashi Suzuki; Koichiro Hagihara; Takeo Arai; Setsuko Mino; Haruko Eguchi, all of Ohimachi, Japan

[73] Assignee: Nisshin Flour Milling Co., Ltd., Tokyo, Japan

[21] Appl. No.: 737,335

[22] PCT Filed: May 17, 1995

[86] PCT No.: PCT/JP95/00937

§ 371 Date: Nov. 15, 1996

§ 102(e) Date: Nov. 15, 1996

[87] PCT Pub. No.: WO95/31442

PCT Pub. Date: Nov. 23, 1995

[30] Foreign Application Priority Data

May 18, 1994 [JP] Japan ................................ 6-127161

[51] Int. Cl.[6] ............ C07D 239/02; C07D 239/00; C07D 241/02; A01N 43/54
[52] U.S. Cl. .............. 514/261; 514/272; 544/311; 544/325; 544/407
[58] Field of Search .................. 544/311, 325, 544/407; 514/269, 272

[56] References Cited

U.S. PATENT DOCUMENTS 4,760,163  7/1988  Wenger et al. ............... 560/34

FOREIGN PATENT DOCUMENTS 32 05 638  8/1983  Germany.
224 032    6/1985  Germany.
229 403    11/1985 Germany.

OTHER PUBLICATIONS

Senda et al., "Pyrimidine Derivatives . . . 1,3-Dimethyluracil", Chem. Pharm. Bull., vol. 26 (1978), pp. 3208-3211.
Stein, "Internal Medicine", Fourth Edition, (1994), Chapter 168 (Diabetes Mellitus), pp. 421.
Senda, "Pyrimidine Derivatives & Related Compounds...", Chem. Pharm. Bull., vol. 26 (1978), 10, pp. 3208-3211.
Chemical Abstracts, vol. 90, No. 15, Apr. 9, 1979, AN 121256t.
Chemical Abstracts, vol. 74, No. 1, Jan. 4, 1971, AN 3582e.
Chemical Abstracts, vol. 115, No. 17, Oct. 28, 1991, AN 183231m.
Kosaku Hirota, et al., Journal of the Chemical Society, Perkin Transaction 1, vol. 8, (1984), pp. 1719-1723, "Pyrimidine Derivatives and Related Compounds. Part 50.[1] Photochemical Reaction of 5-Substituted 6-Azido-1,3-Dimethyluracils with Nucleophiles. Ring Transformation of Pyrimidine to 1,3,5-Triazepine and Hydantoin Ring Systems[2]".

Michael Gelbin, et al., Journal Fuer Praktische Chemie, vol. 329, No. 05, (1987), pp. 753-766, "Ketene-S,N-Acetals As Synthons For Heterocycles New Synthesis of Pyrimidiones".

N.D. Bodnarchuk, et al., ZH. ORG. KHIM., vol. 12, No. 10, (1976), pp. 2253-2256, with Chemical Abstract, vol. 86, No. 11, 11 AN 72568q.

*Primary Examiner*—Mukund J. Shah
*Assistant Examiner*—Tamthom T. Ngo
*Attorney, Agent, or Firm*—Oblon, Spivak, McClelland, Maier & Neustadt, P.C.

[57] ABSTRACT

Pyrimidine derivatives useful as a gastrointestinal prokinetic agent, represented by formula

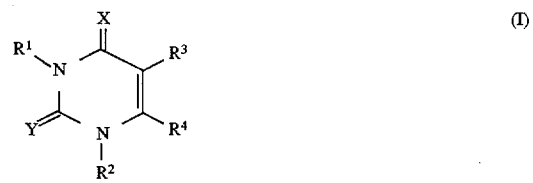

(I)

wherein

X is O or $NR^5$, Y is O, S or $NR^5$ wherein $R^5$ is a hydrogen atom, a $C_1$–$C_6$ alkyl group or the like;

$R^1$ and $R^2$ may be the same or different and each is a hydrogen atom, a $C_1$–$C_6$ alkyl group or the like;

$R^3$ is CN, or $COOR^6$ wherein $R^6$ is a $C_1$–$C_6$ alkyl group, a $C_3$–$C_6$ cycloalkyl group, an aryl group or the like;

$R^4$ is —$SR^7$ or —$NR^8R^9$ wherein $R^7$ is a $C_1$–$C_6$ alkyl group;

$R^8$ is a $C_1$–$C_6$ alkyl group or the like;

$R^9$ is a hydrogen atom, a $C_1$–$C_6$ alkyl group or the like, or $R^8$ and $R^9$ may represent, together with the nitrogen atom to which they are attached, an N-substituted piperazine ring of formula (X)

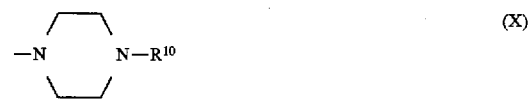

(X)

wherein $R^{10}$ represents a $C_1$–$C_6$ alkyl group or the like or a pharmacologically acceptable salt thereof.

The above-mentioned compounds are useful as a gastrointestinal prokinetic agent used for the therapy of digestive tract diseases.

9 Claims, No Drawings

PYRIMIDINE DERIVATIVES

This is a 371 application of PCT/JP95/00937 filed on May 17, 1995.

TECHNICAL FIELD

This invention relates to new pyrimidine derivatives and pharmacologically acceptable acid addition salts and quaternary ammonium salts thereof, as well as a process for the preparation of such pyrimidine derivatives.

More particularly, this invention relates to a new pyrimidine derivative which has a promoting action of the release of acetylcholine in digestive tracts, thus being useful for the treatment of digestive tract disorders derived from chronic gastritis, diabetes mellitus, post-gastrectomy and peptic ulcer and digestive tract diseases including reflux esophagitis, irritable bowel syndrome and spurious ileus and a gastrointestinal prokinetic agent which comprises as an active ingredient the said derivatives.

BACKGROUND ART

The abnormality in function of a gastrointestinal mobility by various causes such as chronic gastritis, diabetes mellitus, post-gastrectomy syndrome, peptic ulcer and others results in the reflux of the gastric content into the esophagus, delayed emptying of the gastric content and the depressed function of the small and large intestines.

This leads to appearance of nausea, vomiting, heartburn, anorexia, abdominal distention, epigastric dysphoria, abdominaglia, constipation and further reflux esophagitis. One cause of the diseases such as irritable bowel syndrome and spurious ileus is considered to be the depression in gastrointestinal motility.

The agents for the treatment of these conditions and diseases include direct cholinergic agent (e.g. Aclatonium Napadisilate) or Dopamine antagonist (e.g. Doperidone). However, it is well known that these known agents have the problems in their effects and side-effects, which include, for example, diarrhea and extrapyramidal syndrome.

It is well known that acetylcholine is the neurotransmitter participating in the control of gastrointestinal motility. Thus, a compound capable of accelerating the release of acetylcholine in digestive tracts may be a gastrointestinal prokinetic agent with more effectiveness and less side effects. In this circumstance, such a compound has been required to elucidate.

DISCLOSURE OF INVENTION

The present inventors have made earnest studies to solve the above problems and found that the pyrimidine derivatives as defined below have prominent promoting action of the release of acetylcholine, thus leading to the completion of the present invention.

More particularly, this invention is concerned with a pyrimidine derivative represented by formula (I)

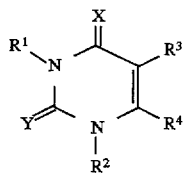

(I)

wherein

X is O or $NR^5$; Y is O, S or $NR^5$ wherein $R^5$ is a hydrogen atom, a $C_1$–$C_6$ alkyl group, a $C_1$–$C_6$ alkylcarbonyl group, an aryl group, an aryl $C_1$–$C_6$ alkyl group, an arylaminocarbonyl group, an aryl $C_1$–$C_4$ alkylaminocarbonyl group, or a $C_1$–$C_6$ alkylaminocarbonyl group;

$R^1$ and $R^2$ may be the same or different and each is a hydrogen atom, a $C_1$–$C_6$ alkyl group, a $C_3$–$C_6$ cycloalkyl group, an aryl group, a $C_3$–$C_6$ cycloalkyl $C_1$–$C_4$ alkyl group, or an aryl $C_1$–$C_4$ alkyl group;

$R^3$ is CN or $COOR^6$ wherein $R^6$ is a $C_1$–$C_6$ alkyl group, a $C_3$–$C_6$ cycloalkyl group, an aryl group, or an aryl $C_1$–$C_4$ alkyl group;

$R^4$ is —$SR^7$ or —$NR^8R^9$ wherein $R^7$ is a $C_1$–$C_6$ alkyl group; $R^8$ is a C–$C_6$ alkyl group, an aryl $C_1$–$C_4$ alkyl group, a heteroaryl $C_1$–$C_4$ alkyl group, an aryloxy $C_2$–$C_6$ alkyl group, in which the aryl or heteroaryl moiety may be optionally mono- to tri-substituted with a halogen atom, a $C_1$–$C_6$ alkyl group, a halo $C_1$–$C_6$ alkyl group, a $C_1$–$C_6$ alkoxy group, a $C_1$–$C_6$ alkoxycarbonyl group or a phenyl group, or $R^8$ represents a group of formulae (II)–(IX)

(II)

(III)

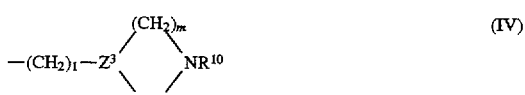

(IV)

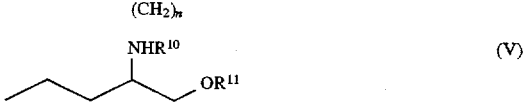

(V)

(VI)

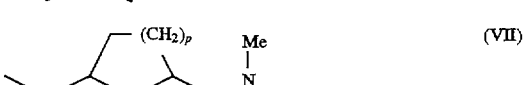

(VII)

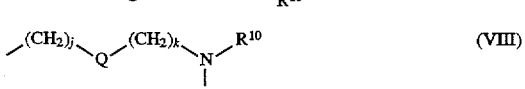

(VIII)

(IX)

wherein $R^{10}$ is a $C_1$–$C_6$ alkyl group, an aryl $C_1$–$C_6$ alkyl group, a heteroaryl $C_1$–$C_6$ alkyl group, an aryloxy $C_2$–$C_6$ alkyl group, a pyrrolidinylcarbonyl $C_1$–$C_4$ alkyl group, in which the aryl moiety may be optionally substituted with a halogen atom, a $C_1$–$C_6$ alkyl group, a halo $C_1$–$C_6$ alkyl group, a $C_1$–$C_6$ alkoxy group, a $C_1$–$C_6$ alkoxycarbonyl group, a phenyl group or an amino group; $R^{11}$ is a hydrogen atom, a $C_1$–$C_6$ alkyl group, an aryl $C_1$–$C_4$ alkyl group or an aryl group; $Z^1$ and $Z^2$ are O, S, N($C_1$–$C_6$ alkyl) or $CH_2$; $Z^3$ is N or CH; l is 0–2; n is 4 when m is 0, n is 1 or 3 when m is 1, n is 2 when m is 2; p is 1–2; j is 0–3; k is 0–3; a sum of j and k is 1–6; h is 1–6; Q is O, $NR^{13}$, $CHOR^{14}$ or $OCH_2CH_2O$; $R^{12}$ and $R^{13}$ may be the same or different and each is a hydrogen atom, a $C_1$–$C_6$ alkyl group or a $C_1$–$C_4$ alkoxy $C_2$–$C_4$ alkyl group; $R^{14}$ is a hydrogen atom or a $C_1$–$C_6$ alkyl group; $R^9$ is a hydrogen atom, a $C_1$–$C_6$ alkyl group or a $C_1$–$C_6$ alkoxy $C_2$–$C_6$ alkyl group; or $R^8$ and $R^9$ may represent, together with the nitrogen atom to which they are attached, an N-substituted piperazine ring of formula (X)

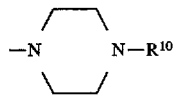
(X)

wherein $R^{10}$ represents the groups as defined above; or a pharmacologically acceptable salt thereof.

In formula (I) for the pyrimidine derivatives of this invention, the $C_1$–$C_6$ alkyl group represented by $R^1$ and $R^2$ includes methyl, ethyl, n-propyl, isopropyl, n-butyl, isobutyl, n-pentyl, neo-pentyl, n-hexyl and the like; the $C_3$–$C_6$ cycloalkyl group includes cyclopropyl, cyclopentyl or cyclohexyl; the aryl group includes phenyl, naphthyl, o-fluorophenyl, m-fluorophenyl, p-fluorophenyl, o-chlorophenyl, m-chlorophenyl, p-chlorophenyl, 3,4-dichlorophenyl, o-methylphenyl, m-methylphenyl, p-methylphenyl, o-ethylphenyl, m-ethylphenyl, p-ethylphenyl, o-methoxyphenyl, m-methoxyphenyl, p-methoxyphenyl, 3,4-dimethoxyphenyl, o-ethoxyphenyl, m-ethoxyphenyl, p-ethoxyphenyl, 3,4-diethoxyphenyl, o-methoxycarbonylphenyl, m-methoxycarbonylphenyl, p-methoxycarbonylphenyl, o-aminophenyl, m-aminophenyl, p-aminophenyl and the like; the $C_3$–$C_6$ cycloalkyl $C_1$–$C_4$ alkyl group includes cyclopropylmethyl, cyclohexylmethyl and the like; the aryl $C_1$–$C_4$ alkyl group includes benzyl, phenethyl, o-fluorobenzyl, m-fluorobenzyl, p-fluorobenzyl, o-chlorobenzyl, m-chlorobenzyl, p-chlorobenzyl, 3,4-dichlorobenzyl, o-methylbenzyl, m-methylbenzyl, p-methylbenzyl, o-trifluoromethylbenzyl, m-trifluoromethylbenzyl, p-trifluoromethylbenzyl, 3,4-ditrifluoromethylbenzyl, o-methoxybenzyl, m-methoxybenzyl, p-methoxybenzyl, 3,4-dimethoxybenzyl, o-methoxycarbonylbenzyl, m-methoxycarbonylbenzyl, p-methoxycarbonylbenzyl, biphenyl-2-ylmethyl, biphenyl-3-ylmethyl, biphenyl-4-ylmethyl, o-aminobenzyl, m-aminobenzyl, p-aminobenzyl, o-fluorophenethyl, m-fluorophenethyl, p-fluorophenethyl, o-chlorophenethyl, m-chlorophenethyl, p-chlorophenethyl, 3,4-dichlorophenethyl, o-methylphenethyl, m-methylphenethyl, p-methylphenethyl, o-trifluoromethylphenethyl, m-trifluoromethylphenethyl, p-trifluoromethylphenethyl, o-methoxyphenethyl, m-methoxyphenethyl, p-methoxyphenethyl, 3,4-dimethoxyphenethyl, o-methoxycarbonylphenethyl, o-methoxycarbonylphenethyl, m-methoxycarbonylphenethyl, p-methoxycarbonylphenethyl, 2-(biphenyl-2-yl)ethyl, 2-(biphenyl-3-yl)ethyl, 2-(biphenyl-4-yl)ethyl, o-aminophenethyl, m-aminophenethyl, p-aminophenethyl; the $C_1$–$C_6$ alkyl group represented by $R^5$ includes methyl, ethyl, n-propyl, iso-propyl, n-butyl, isobutyl, n-pentyl, neo-pentyl, n-hexyl and the like; the $C_1$–$C_6$ alkylcarbonyl group includes acetyl, propionyl, butyryl, isobutyryl, valeryl, isovaleryl, pivaloyl and the like; the aryl group includes phenyl, naphthyl and the like; the aryl $C_1$–$C_6$ alkyl group includes benzyl, phenethyl and the like; the arylaminocarbonyl group includes anilinocarbonyl and the like; the aryl $C_1$–$C_4$ alkylaminocarbonyl group includes benzylaminocarbonyl, phenethylaminocarbonyl and the like; the $C_1$–$C_6$ alkylaminocarbonyl group includes methylaminocarbonyl, n-hexylaminocarbonyl and the like; the $C_1$–$C_6$ alkyl group represented by $R^6$ includes methyl, ethyl, n-propyl, isopropyl, n-butyl, isobutyl, n-pentyl, neopentyl, n-hexyl and the like; the $C_3$–$C_6$ cycloalkyl group includes cyclopropyl, cyclopentyl, cyclohexyl and the like; the aryl group includes phenyl, naphthyl and the like; the aryl $C_1$–$C_4$ alkyl group includes benzyl, phenethyl and the like; the $C_1$–$C_6$ alkyl group represented by $R^7$ includes methyl, ethyl, n-propyl, isopropyl, n-butyl, isobutyl, n-pentyl, neo-pentyl, n-hexyl and the like; the $C_1$–$C_6$ alkyl group represented by $R^9$ includes methyl, ethyl, n-propyl, isopropyl, n-butyl, isobutyl, n-pentyl, neo-pentyl, n-hexyl and the like; the $C_1$–$C_6$ alkoxy $C_2$–$C_6$ alkyl group includes methoxyethyl, ethoxyethyl and the like; the $C_1$–$C_6$ alkyl group represented by $R^8$ includes methyl, ethyl, n-propyl, isopropyl, n-butyl, isobutyl, n-pentyl, neo-pentyl, n-hexyl and the like; the aryl $C_1$–$C_4$ alkyl group includes benzyl, phenethyl, o-fluorobenzyl, m-fluorobenzyl, p-fluorobenzyl, o-chlorobenzyl, m-chlorobenzyl, p-chlorobenzyl, 3,4-dichlorobenzyl, o-methylbenzyl, m-methylbenzyl, p-methylbenzyl, o-trifluoromethylbenzyl, m-trifluoromethylbenzyl, p-trifluoromethylbenzyl, o-methoxybenzyl, m-methoxybenzyl, p-methoxybenzyl, 3,4-dimethoxybenzyl, o-methoxycarbonylbenzyl, m-methoxycarbonylbenzyl, p-methoxycarbonylbenzyl, biphenyl-2-ylmethyl, biphenyl-3-ylmethyl, biphenyl-4-ylmethyl, o-aminobenzyl, m-aminobenzyl, p-aminobenzyl, o-fluorophenethyl, m-fluorophenethyl, p-fluorophenethyl, o-chlorophenethyl, m-chlorophenethyl, p-chlorophenethyl, 3,4-dichlorophenethyl, o-methylphenethyl, m-methylphenethyl, p-methylphenethyl, o-trifluoromethylphenethyl, m-trifluoromethylphenethyl, p-trifluoromethylphenethyl, o-methoxyphenethyl, m-methoxyphenethyl, p-methoxyphenethyl, 3,4-dimethoxyphenethyl, o-methoxycarbonylphenethyl, m-methoxycarbonylphenethyl, p-methoxycarbonylphenethyl, 2-(biphenyl-2-yl)ethyl, 2-(biphenyl-3-yl)ethyl, 2-(biphenyl-4-yl)ethyl, o-aminophenethyl, m-aminophenethyl, p-aminophenethyl and the like; the heteroaryl $C_1$–$C_4$ alkyl group includes 2-pyridylmethyl, 3-pyridylmethyl, 4-pyridylmethyl, 1H-indol-3-ylethyl and the like; the aryloxy $C_2$–$C_6$ alkyl group includes phenoxy-2-ethyl, phenoxy-3-propyl, 4-fluorophenoxypropyl and the like.

The $C_1$–$C_6$ alkyl group represented by $R^{10}$ in formulae (II)–(IX) includes methyl, ethyl, n-propyl, isopropyl, n-butyl, isobutyl, n-pentyl, neo-pentyl, n-hexyl and the like; the aryl $C_1$–$C_4$ alkyl group includes benzyl, phenethyl, o-fluorobenzyl, m-fluorobenzyl, p-fluorobenzyl, o-chlorobenzyl, m-chlorobenzyl, p-chlorobenzyl, 3,4-dichlorobenzyl, o-methylbenzyl, m-methylbenzyl, p-methylbenzyl, o-trifluoromethylbenzyl, m-trifluoromethylbenzyl, p-trifluoromethylbenzyl, o-methoxybenzyl, m-methoxybenzyl, p-methoxybenzyl, 3,4-dimethoxybenzyl, o-methoxycarbonylbenzyl, m-methoxycarbonylbenzyl, p-methoxycarbonylbenzyl, biphenyl-2-ylmethyl, biphenyl-3-ylmethyl, biphenyl-4-ylmethyl, o-aminobenzyl, m-aminobenzyl, p-aminobenzyl, o-fluorophenethyl, m-fluorophenethyl, p-fluorophenethyl, o-chlorophenethyl, m-chlorophenethyl, p-chlorophenethyl, 3,4-dichlorophenethyl, o-methylphenethyl, m-methylphenethyl, p-methylphenethyl, o-trifluoromethylphenethyl, m-trifluoromethylphenethyl, p-trifluoromethylphenethyl, o-methoxyphenethyl, m-methoxyphenethyl, p-methoxyphenethyl, 3,4-dimethoxyphenethyl, o-methoxycarbonylphenethyl, m-methoxycarbonylphenethyl, p-methoxycarbonylphenethyl, 2-(biphenyl-2-yl)ethyl, 2-(biphenyl-3-yl)ethyl, 2-(biphenyl-4-yl)ethyl, o-aminophenethyl, m-aminophenethyl, p-aminophenethyl and the like; the heteroaryl $C_1$–$C_4$ alkyl group may include 2-pyridylmethyl, 3-pyridylmethyl, 4-pyridylmethyl, 1H-indol-3-ylethyl and the like; the aryloxy $C_2$–$C_6$ alkyl group includes phenoxy-2-ethyl, phenoxy-3-propyl, 2-fluorophenoxy-3-propyl, 3-fluorophenoxy-3-propyl, 4-fluorophenoxy-3-propyl, 2-chlorophenoxy-3-propyl, 3-chlorophenoxy-3-propyl, 4-chlorophenoxy-3-propyl, 3,4-dichlorophenoxy-3-propyl and the like; the pyrrolidinylcarbonyl $C_1$–$C_4$ alkyl group includes pyrrolidinylcarbonylmethyl and the like; the $C_1$–$C_6$ alkyl group represented by $R^{11}$ includes methyl, ethyl, n-propyl, isopropyl, n-butyl, isobutyl, n-pentyl, neo-pentyl, n-hexyl and the like; the aryl $C_1$–$C_4$ alkyl group includes benzyl, phenethyl and the like; the aryl group includes phenyl, naphthyl and the like; the $C_1$–$C_6$ alkyl group in the $N(C_1$–$C_6$ alkyl) group for $Z^1$ and $Z^2$ includes methyl, ethyl, n-propyl, isopropyl, n-butyl, isobutyl, n-pentyl, neo-pentyl, n-hexyl and the like; the $C_1$–$C_6$ alkyl group represented by $R^{12}$ and $R^{13}$ includes methyl, ethyl, n-propyl, isopropyl, n-butyl, isobutyl, n-pentyl, neo-pentyl, n-hexyl and the like; the $C_1$–$C_4$ alkoxy $C_2$–$C_4$ alkyl group includes methoxyethyl, ethoxyethyl and the like; the $C_1$–$C_6$ alkyl group represented by $R^{14}$ includes methyl, ethyl, n-propyl, isopropyl, n-butyl, isobutyl, n-pentyl, neo-pentyl, n-hexyl and the like.

The compounds represented by formula (I) of this invention may be prepared according to various processes as explained below. In the following processes, X, Y, and $R^1$–$R^{14}$ are as defined above.

(1) In the case where $R^4$ is —$SR^7$:

(i) In the case where $R^1$ and $R^2$ are the same and Y is S:

The compound represented by formula (i) may be prepared by reacting an isothiocyanate represented by formula (XI)

$$R^1NCY(Y=S) \qquad (XI)$$

with a compound represented by formula (XII)

$$R^3CH_2R^{3'} \qquad (XII)$$

wherein $R^{3'}$ may be identical with or different from $R^3$ and represents CN or $COOR^6$ in the presence of a base followed by reaction with an alkyl halide represented by formula $R^7$—Hal wherein Hal represents a halogen atom.

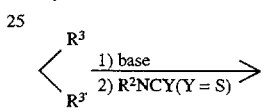

(Y = S)

Where $R^{3'}=COOR^6$, X=O; where $R^{3'}=CN$, X=NH.

In this case, the isothiocyanate represented by formula (XI) includes methyl isothiocyanate, ethyl isothiocyanate, propyl isothiocyanate, isopropyl isothiocyanate, butyl isothiocyanate, isobutyl isothiocyanate, phenyl isothiocyanate and the like. The compound represented by formula (XII) includes malononitrile, methyl cyanoacetate, ethyl cyanoacetate, butyl cyanoacetate, cyclohexyl cyanoacetate, phenyl cyanoacetate, benzyl cyanoacetate, dimethyl malonate, diethyl malonate, di-n-propyl malonate, diisopropyl malonate, di-n-butyl malonate, dipentyl malonate, dihexyl malonate, dicyclohexyl malonate, diphenyl malonate, dibenzyl malonate and the like.

The above-mentioned reaction may be carried out by using the compound represented by formula (XI) in an amount of 0.1–10 moles, preferably 0.2–2 moles, per one mole of the compound represented by the formula (XI) in the presence of an organic solvent at a temperature ranging from −78° C. to 200° C., preferably −10° C. to 150° C.

(ii) In the case where $R^1$ and $R^2$ are different each other:

The compound represented by formula (I) may be prepared by reacting an isothiocyanate represented by formula (XIII)

$$R^2NCY(Y=S) \qquad (XIII)$$

with a compound represented by formula (XII)

$$R^3CH_2R^{3'} \qquad (XII)$$

wherein $R^{3'}$ is as defined above, in the presence of a base, then reacting with an isothiocyanate represented by formula (XI)

$$R^1NCY(Y=S) \qquad (XI)$$

and subsequently reacting with an alkyl halide represented by formula $R^7$—Hal wherein Hal is as defined above.

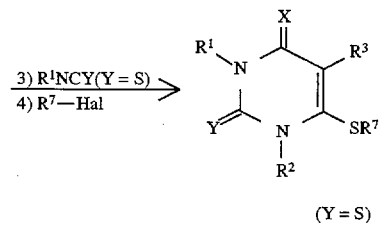

(Y = S)

Where $R^{3'}=COOR^6$, X=O; where $R^{3'}=CN$, X=NH.

In this case, the isothiocyanate represented by formula (XI) or (XIII) includes methyl isothiocyanate, ethyl isothiocyanate, propyl isothiocyanate, isopropyl isothiocyanate, butyl isothiocyanate, isobutyl isothiocyanate, phenyl isothiocyanate and the like. The compound represented by formula (XII) includes malononitrile, methyl cyanoacetate, ethyl cyanoacetate, butyl cyanoacetate, cyclohexyl cyanoacetate, phenyl cyanoacetate, benzyl cyanoacetate, dimethyl malonate, diethyl malonate, di-n-propyl malonate, diisopropyl malonate, di-n-butyl malonate, dipentyl malonate, dihexyl malonate, dicyclohexyl malonate, diphenyl malonate, dibenzyl malonate and the like.

The above-mentioned reaction may be carried out by using the compound represented by formula (XI) in an amount of 0.1–10 moles, preferably 0.2–2 moles, and subsequently the compound of formula (XII) in an amount of 0.1–10 moles, preferably 0.5–2 moles, per one mole of the compound represented by the formula (XIII) in the presence of an organic solvent at a temperature ranging from −78° C. to 200° C., preferably −10° C. to 150° C.

(iii) In the case where $R^1$ and $R^2$ may be the same or different and Y is O, S or $NR^5$:

The compound represented by formula (I) may be prepared by reacting an isothiocyanate represented by formula (XIII)

$$R^2NCY(Y=S) \qquad (XIII)$$

with a compound represented by formula (XII)

R³CH₂R³' (XII)

wherein R³' is as defined above in the presence of a base, then reacting with an alkyl halide represented by formula R⁷—Hal wherein Hal is as defined above to form a methylidene derivative represented by the formula (XIV)

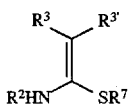

(XIV)

and then reacting with an isocyanate, isothiocyanate or carbodiimide represented by formula (XI)

R¹NCY(Y=O, S, NR⁵) (XI).

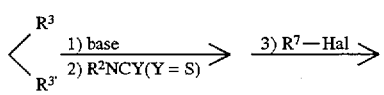

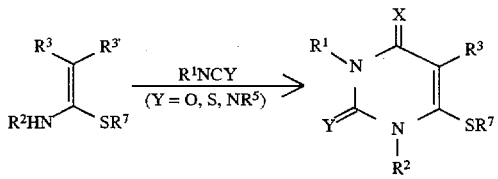

(Y = O, S, NR⁵)

Where R³'=COOR⁶, X=O; where R³'=CN, X=NH or NCONHR¹.

In this case, the isothiocyanate represented by formula (XI) or (XIII) includes methyl isothiocyanate, ethyl isothiocyanate, propyl isothiocyanate, isopropyl isothiocyanate, butyl isothiocyanate, isobutyl isothiocyanate, phenyl isothiocyanate and the like. The isocyanate represented by formula (XI) includes methyl isocyanate, ethyl isocyanate, propyl isocyanate, isopropyl isocyanate, butyl isocyanate, isobutyl isocyanate, phenyl isocyanate and the like; the carbodiimide includes dimethylcarbodiimide, diethylcarbodiimide, diisopropylcarbodiimide, di-tert-butylcarbodiimide, diphenylcarbodiimide and the like. The compound represented by formula (XII) includes malononitrile, methyl cyanoacetate, ethyl cyanoacetate, butyl cyanoacetate, cyclohexyl cyanoacetate, phenyl cyanoacetate, benzyl cyanoacetate, dimethyl malonate, diethyl malonate, di-n-propyl malonate, diisopropyl malonate, di-n-butyl malonate, dipentyl malonate, dihexyl malonate, dicyclohexyl malonate, diphenyl malonate, dibenzyl malonate and the like.

The above-mentioned reaction may be carried out by using the compound represented by formula (XII) in an amount of 0.1–10 moles, preferably 0.2–2 moles and the compound represented by formula (XI) in an amount of 0.1–10 moles, preferably 0.5–4 moles, per one mole of the compound represented by the formula (XIII) in the presence of an organic solvent at a temperature ranging from –78° C. to 200° C., preferably –10° C. to 150° C.

(2) In the case where R⁴ is —NR⁸R⁹:

The pyrimidine derivative represented by formula (I) (R⁴=SR⁷) obtained in the above item (1), after isolation or subsequently without any isolation, may be reacted with an amino compound represented by formula (XV)

HNR⁸R⁹ (XV)

to form the desired compound.

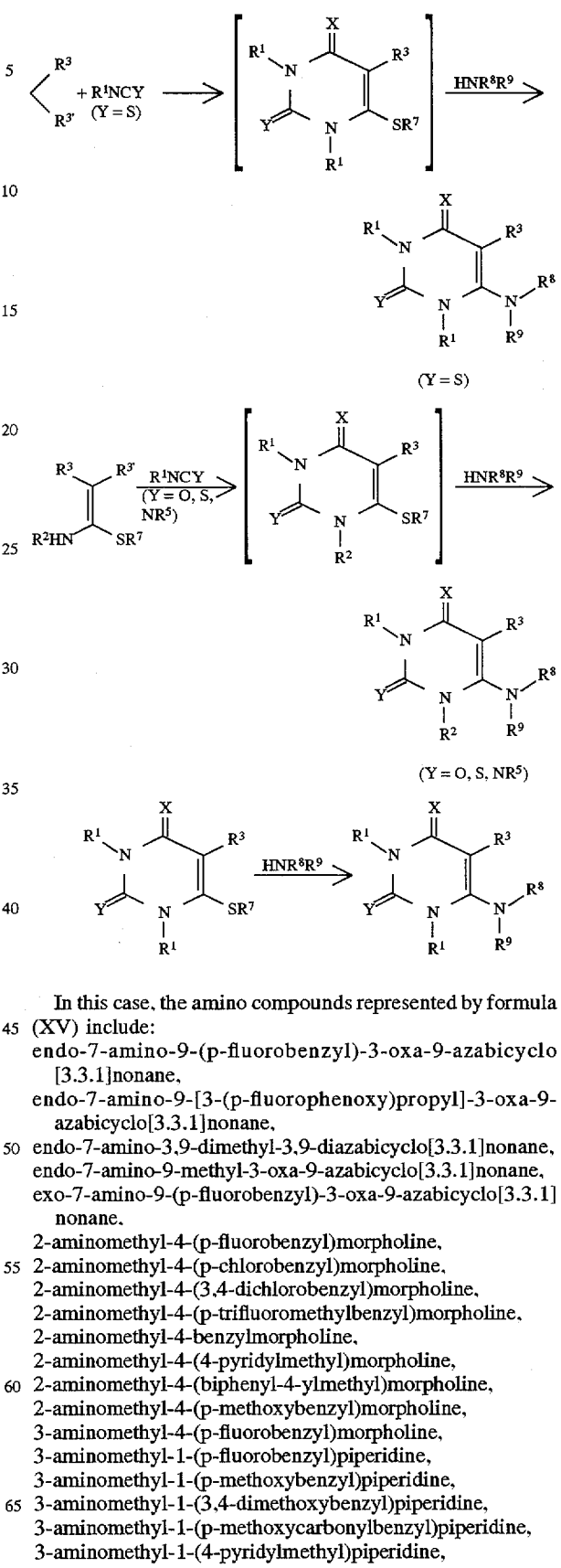

In this case, the amino compounds represented by formula (XV) include:
endo-7-amino-9-(p-fluorobenzyl)-3-oxa-9-azabicyclo[3.3.1]nonane,
endo-7-amino-9-[3-(p-fluorophenoxy)propyl]-3-oxa-9-azabicyclo[3.3.1]nonane,
endo-7-amino-3,9-dimethyl-3,9-diazabicyclo[3.3.1]nonane,
endo-7-amino-9-methyl-3-oxa-9-azabicyclo[3.3.1]nonane,
exo-7-amino-9-(p-fluorobenzyl)-3-oxa-9-azabicyclo[3.3.1]nonane,
2-aminomethyl-4-(p-fluorobenzyl)morpholine,
2-aminomethyl-4-(p-chlorobenzyl)morpholine,
2-aminomethyl-4-(3,4-dichlorobenzyl)morpholine,
2-aminomethyl-4-(p-trifluoromethylbenzyl)morpholine,
2-aminomethyl-4-benzylmorpholine,
2-aminomethyl-4-(4-pyridylmethyl)morpholine,
2-aminomethyl-4-(biphenyl-4-ylmethyl)morpholine,
2-aminomethyl-4-(p-methoxybenzyl)morpholine,
3-aminomethyl-4-(p-fluorobenzyl)morpholine,
3-aminomethyl-1-(p-fluorobenzyl)piperidine,
3-aminomethyl-1-(p-methoxybenzyl)piperidine,
3-aminomethyl-1-(3,4-dimethoxybenzyl)piperidine,
3-aminomethyl-1-(p-methoxycarbonylbenzyl)piperidine,
3-aminomethyl-1-(4-pyridylmethyl)piperidine, 3-aminomethyl-1-(p-trifluoromethylbenzyl)piperidine,
3-aminomethyl-1-(p-chlorobenzyl)piperidine,
3-aminomethyl-1-(3,4-dichlorobenzyl)piperidine,
3-amino-1-(p-fluorobenzyl)azetidine,
4-amino-1-(p-fluorobenzyl)piperidine,
1-(p-fluorobenzyl)piperazine,
1-(p-fluorobenzyl)-4-(2-aminoethyl)piperazine,
2-(2-methylaminoethyl)-1-(p-fluorobenzyl)piperidine,
4-aminomethyl-1-(p-fluorobenzyl)piperidine,
2-aminomethyl-1-(p-fluorobenzyl)piperidine,
1-[2-oxo-2-(1-pyrrolidinyl)ethyl]piperazine,
3-(p-fluorobenzylamino)-6-phenyl-5-oxahexylamine,
2-(p-fluorobenzyl)-3aβ,5α,6aβ-octahydrocyclopenta[c]-pyrrole-5-amine,
5-(p-fluorophenyl)-1-amino-4-aza-2-pentanol,
N-(p-fluorobenzyl)-N,N'-bis(2-methoxyethyl)-1,3-propanediamine,
4-(p-fluorobenzyl)-4-aza-7-oxaoctylamine,
cis-2-aminomethyl-6-[N-ethoxycarbonyl-N-(p-fluorobenzyl)aminomethyl]tetrahydropyrane,
trans-2-aminomethyl-6-[N-ethoxycarbonyl-N-(p-fluorobenzyl)aminomethyl]tetrahydropyran,
trans-2-aminomethyl-5-[N-methoxycarbonyl-N-(p-fluorobenzyl)aminomethyl]tetrahydrofuran,
cis-2-aminomethyl-5-[N-methoxycarbonyl-N-(p-fluorobenzyl)aminomethyl]tetrahydrofuran,
tryptamine,
isopropylamine,
p-fluorobenzylamine,
tert-butyl N-(5-amino-3-tert-butoxycarbonyl-3-azapentyl)-N-(p-fluorobenzyl)carbamate,
tert-butyl N-(5-amino-3-oxapentyl)-N-(p-fluorobenzyl)carbamate,
tert-butyl N-(3-aminopropyl)-N-(p-fluorobenzyl)carbamate,
tert-butyl N-(4-aminobutyl)-N-(p-fluorobenzyl)carbamate and
5-cyano-4-imino-1,3-dimethyl-6-methylthio-3,4-dihydro-2(1H)-pyrimidinethione,
tert-butyl N-(5-aminopentyl)-N-(p-fluorobenzyl)carbamate,
tert-butyl N-(3-amino-2-methoxypropyl)-N-(p-fluorobenzyl)carbamate,
tert-butyl N-(p-fluorobenzyl)-N-(5-amino-3-oxapentyl)carbamate and others.

The corresponding tert-butyl carbamate derivatives having the protected amino group as shown above may be deprotected after the reaction to form the corresponding pyrimidine derivatives (I).

The above-mentioned reaction may be carried out by using the compound represented by formula (XV) in an amount of 0.1–10 moles, preferably 0.2–2 moles, per one mole of the pyrimidine derivative represented by formula (I) obtained in the above item (1) in the presence of an organic solvent at a temperature ranging from −78° C. to 200° C., preferably −10° C. to 150° C.

Alternatively, the compound (I) may be prepared by reacting a diaminomethylidene derivative represented by formula (XVI)

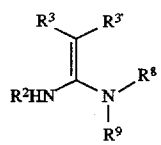
(XVI)

with a compound represented by formula (XI)

R¹NCY (Y=O, S, NR⁵)  (XI)

in the presence of a base.

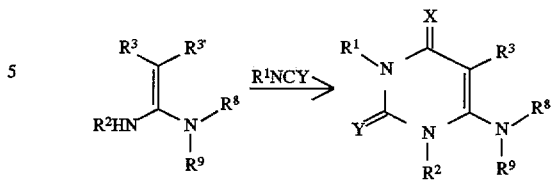

In this case, the diaminomethylidene derivatives represented by formula (XVI) include:
2-[4-(p-fluorobenzyl)-2-morpholinylmethylamino]-2-methylamino-1,1-ethylenedicarbonitrile,
2-[4-(p-chlorobenzyl)-2-morpholinylmethylamino]-2-methylamino-1,1-ethylenedicarbonitrile,
2-[4-(3,4-dichlorobenzyl)-2-morpholinylmethylamino]-2-methylamino-1,1-ethylenedicarbonitrile,
2-[4-(p-trifluoromethylbenzyl)-2-morpholinylmethylamino]-2-methylamino-1,1-ethylenedicarbonitrile,
2-(4-benzyl-2-morpholinylmethylamino)-2-methylamino-1,1-ethylenedicarbonitrile,
2-methylamino-2-[4-(4-pyridylmethyl)-2-morpholinylmethyl-amino]-1,1-ethylenedicarbonitrile,
2-[4-(biphenyl-4-ylmethyl)-2-morpholinylmethylamino]-2-methylamino-1,1-ethylenedicarbonitrile,
2-[4-(p-methoxybenzyl)-2-morpholinylmethylamino]-2-methylamino-1,1-ethylenedicarbonitrile,
2-[1-(p-fluorobenzyl)-3-piperidinylmethylamino]-2-methylamino-1,1-ethylenedicarbonitrile,
2-[1-(p-methoxybenzyl)-3-piperidinylmethylamino]-2-methylamino-1,1-ethylenedicarbonitrile,
2-[1-(3,4-dimethoxybenzyl)-3-piperidinylmethylamino]-2-methylamino-1,1-ethylenedicarbonitrile,
2-[1-(p-methoxycarbonylbenzyl)-3-piperidinylmethylamino]-2-methylamino-1,1-ethylenedicarbonitrile,
2-methylamino-2-[1-(4-pyridylmethyl)-3-piperidinylmethyl-amino]-1,1-ethylenedicarbonitrile,
2-[1-(p-trifluoromethylbenzyl)-3-piperidinylmethylamino]-2-methylamino-1,1-ethylenedicarbonitrile,
2-[1-(p-chlorobenzyl)-3-piperidinylmethylamino]-2-methylamino-1,1-ethylenedicarbonitrile,
2-[1-(3,4-dichlorobenzyl)-3-piperidinylmethylamino]-2-methylamino-1,1-ethylenedicarbonitrile,
2-[endo-9-(p-fluorobenzyl)-3-oxa-9-azabicyclo[3.3.1]non-7-ylamino]-2-methylamino-1,1-ethylenedicarbonitrile,
2-[endo-9-[3-(p-fluorophenoxy)propyl]-3-oxa-9-azabicyclo[3.3.1]non-7-ylamino]-2-methylamino-1,1-ethylenedicarbonitrile,
2-methylamino-2-(endo-3,9-dimethyl-3,9-diazabicyclo[3.3.1]non-7-ylamino)-1,1-ethylenedicarbonitrile,
2-methylamino-2-(endo-9-methyl-3-oxa-9-azabicyclo[3.3.1]non-7-ylamino)-1,1-ethylenedicarbonitrile,
2-[exo-9-(p-fluorobenzyl)-3-oxa-9-azabicyclo[3.3.1]non-7-ylamino]-2-methylamino-1,1-ethylenedicarbonitrile,
2-[1-(p-fluorobenzyl)-3-azetidinylamino]-2-methylamino-1,1-ethylenedicarbonitrile,
2-[1-(p-fluorobenzyl)-4-piperidinylamino]-2-methylamino-1,1-ethylenedicarbonitrile,
2-[4-(p-fluorobenzyl)-1-piperazinyl]-2-methylamino-1,1-ethylenedicarbonitrile,
2-[2-[4-(p-fluorobenzyl)-1-piperazinyl]ethylamino]-2-methylamino-1,1-ethylenedicarbonitrile,
2-[N-[2-[1-(p-fluorobenzyl)-2-piperidinyl]ethyl]-N-methylamino]-2-methylamino-1,1-ethylenedicarbonitrile,
2-[1-(p-fluorobenzyl)-4-piperidinylmethylamino]-2-methylamino-1,1-ethylenedicarbonitrile, 2-[1-(p-fluorobenzyl)-2-piperidinylmethylamino]-2-methylamino-1,1-ethylenedicarbonitrile, 2-methylamino-2-[4-[2-oxo-2-(1-pyrrolidinyl)ethyl]-1-piperazinyl]-1,1-ethylenedicarbonitrile, 2-[4-benzyloxy-3-(p-fluorobenzylamino)butylamino]-2-methylamino-1,1-ethylenedicarbonitrile, 2-[2-(p-fluorobenzyl)-3aβ,5α,6aβ-octahydrocyclopenta[c]pyrrole-5-amino]-2-methylamino-1,1-ethylenedicarbonitrile, 2-[5-(p-fluorophenyl)-2-hydroxy-4-azapentylamino]-2-methylamino-1,1-ethylenedicarbonitrile, 2-[N-[5-p-fluorophenyl-4-(2-methoxyethyl)-4-azapentyl]-N-(2-methoxyethyl)amino]-2-methylamino-1,1-ethylenedicarbonitrile, 2-[4-(p-fluorobenzyl)-4-aza-7-oxaoctylamino]-2-methylamino-1,1-ethylenedicarbonitrile, 2-[cis-6-[N-(p-fluorobenzyl)-N-methylaminomethyl]-2-tetrahydropyranylmethylamino]-2-methylamino-1,1-ethylenedicarbonitrile, 2-[trans-6-[N-(p-fluorobenzyl)-N-methylaminomethyl]-2-tetrahydropyranylmethylamino]-2-methylamino-1,1-ethylenedicarbonitrile, 2-[trans-5-[N-(p-fluorobenzyl)-N-methylaminomethyl]-2-tetrahydrofuranylmethylamino]-2-methylamino-1,1-ethylenedicarbonitrile, 2-[cis-5-[N-(p-fluorobenzyl)-N-methylaminomethyl]-2-tetrahydrofuranylmethylamino]-2-methylamino-1,1-ethylenedicarbonitrile, 2-benzylamino-2-[4-(p-fluorobenzyl)-1-piperazinyl]-1,1-ethylenedicarbonitrile, ethyl 3-methylamino-3-[4-(p-fluorobenzyl)-2-morpholinylmethylamino]-2-cyanoacrylate and others.

(3) In the case where X is —NR$^5$ (provided that R$^5$ is as defined above, but excluding the hydrogen atom):

The compound of formula (I) wherein X is NH may be reacted with an acid anhydride, an acid halide, an alkyl halide or an isocyanate in the presence of a base to introduce the substituent R$^5$, thereby producing the compound of formula (I) wherein X is NR$^5$.

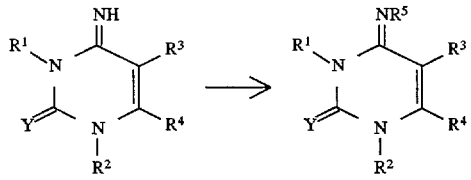

In this case, the acid anhydride includes acetic anhydride, while the acid halide includes acetyl chloride, propionyl chloride, valeryl chloride and the like.

The organic solvent which is used in the reactions as described in the above items (1)–(3) may be any of conventional organic solvents if they could not undergo any change under the respective reaction conditions. More illustratively, there may be used aliphatic hydrocarbon solvents such as hexane, cyclohexane, petroleum ether and the like, aromatic hydrocarbon solvents such as benzene, toluene, xylene and the like, halogenated hydrocarbon solvents such as methylene chloride, chloroform, carbon tetrachloride, dichloroethane and the like, alcohol solvents such as methanol, ethanol, isopropanol and the like, ether solvents such as diethyl ether, isopropyl ether, tetrahydrofuran, dioxane and the like, ketone solvents such as acetone, methyl ethyl ketone and the like, ethyl acetate, acetonitrile, N,N-dimethylformamide and others.

The base which is used in the respective reactions as stated above may be any of inorganic or organic bases. The bases include alkali metal hydroxides such as sodium hydroxide, potassium hydroxide and the like, alkaline earth metal hydroxides such as barium hydroxide and the like, alkali metal carbonates such as sodium carbonate, potassium carbonate and the like, alkaline earth metal carbonates such as calcium carbonate and the like, alkali or alkaline earth metal alcoholates such as sodium methylate, sodium ethylate, potassium ethylate, potassium tert-butoxide and the like, organic aimines such as pyridine, picoline, 4-dimethylaminopyridine, triethylamine and the like, or alkali metal hydrides such as sodium hydride and the like.

The alkyl halides include methyl chloride, ethyl chloride, propyl chloride, butyl chloride, methyl bromide, ethyl bromide, propyl bromide, butyl bromide, methyl iodide, ethyl iodide, propyl iodide, butyl iodide and the like.

Illustrative examples of the present compounds obtained as described above are listed as follows:

5-cyano-6-[endo-9-(p-fluorobenzyl)-3-oxa-9-azabicyclo[3.3.1]non-7-ylamino]-4-imino-1,3-dimethyl-3,4-dihydro-2(1H)-pyrimidinethione, 5-cyano-6-[endo-9-[3-(p-fluorophenoxy)propyl]-3-oxa-9-azabicyclo[3.3.1]non-7-ylamino]-4-imino-1,3-dimethyl-3,4-dihydro-2(1H)-pyrimidinethione, 5-cyano-4-imino-1,3-dimethyl-6-(endo-3,9-dimethyl-3,9-diazabicyclo[3.3.1]non-7-ylamino)-3,4-dihydro-2(1H)-pyrimidinethione, 5-cyano-4-imino-1,3-dimethyl-6-[endo-9-methyl-3-oxa-9-azabicyclo[3.3.1]non-7-ylamino]-3,4-dihydro-2(1H)-pyrimidinethione, 5-cyano-6-[exo-9-(p-fluorobenzyl)-3-oxa-9-azabicyclo[3.3.1]non-7-ylamino]-4-imino-1,3-dimethyl-3,4-dihydro-2(1H)-pyrimidinethione, 5-cyano-6-[endo-9-(p-fluorobenzyl)-3-oxa-9-azabicyclo[3.3.1]non-7-ylamino]-1,3-dimethyl-4-methylimino-3,4-dihydro-2(1H)-pyrimidinethione, 5-cyano-6-[4-(p-fluorobenzyl)-2-morpholinylmethylamino]-4-imino-1,3-dimethyl-3,4-dihydro-2(1H)-pyrimidinethione, 5-cyano-6-[4-(p-fluorobenzyl)-2-morpholinylmethylamino]-4-imino-3-methyl-1-phenyl-3,4-dihydro-2(1H)-pyrimidinethione, 1-[5-cyano-6-[4-(p-fluorobenzyl)-2-morpholinylmethylamino]-1-methyl-2-oxo-3-phenyl-1,2,3,4-tetrahydropyrimidin-4-ylidene]-3-phenylurea, 5-cyano-6-[4-(p-fluorobenzyl)-2-morpholinylmethylamino]-1,3-dimethyl-2-thioxo-2,3-dihydro-4(1H)-pyrimidinone, 5-cyano-6-[4-(p-fluorobenzyl)-2-morpholinylmethylamino]-1,3-dimethyl-2,4(1H,3H)-pyrimidinedione, 5-cyano-6-[4-(p-fluorobenzyl)-2-morpholinylmethylamino]-3-methyl-1-phenyl-2,4(1H,3H)-pyrimidinedione, 6-[4-(3,4-dichlorobenzyl)-2-morpholinylmethylamino]-5-cyano-1,3-dimethyl-2-thioxo-2,3-dihydro-4(1H)-pyrimidinone, 6-[4-(p-fluorobenzyl)-2-morpholinylamino]-3-methyl-1-phenyl-5-(2-propoxycarbonyl)-2-thioxo-2,3-dihydro-4(1H)-pyrimidinone, 6-[4-(p-fluorobenzyl)-2-morpholinylamino]-5-methoxycarbonyl-3-methyl-1-phenyl-2-thioxo-2,3-dihydro-4(1H)-pyrimidinone, 6-[4-(p-fluorobenzyl)-2-morpholinylamino]-5-cyclohexyloxycarbonyl-3-methyl-1-phenyl-2-thioxo-2,3-dihydro-4(1H)-pyrimidinone, 5-n-butoxycarbonyl-6-[4-(p-fluorobenzyl)-2-morpholinylamino]-3-methyl-1-phenyl-2-thioxo-2,3-dihydro-4(1H)-pyrimidinone, 5-benzyloxycarbonyl-6-[4-(p-fluorobenzyl)-2-morpholinylamino]-3-methyl-1-phenyl-2-thioxo-2,3-dihydro-4(1H)-pyrimidinone, 5-methoxycarbonyl-6-[4-(3,4-dichlorobenzyl)-2-morpholinylamino]-3-methyl-1-phenyl-2-thioxo-2,3-dihydro-4(1H)-pyrimidinone, 6-[4-(3,4-dichlorobenzyl)-2-morpholinylamino]-3-methyl-1-phenyl-5-(2-propoxycarbonyl)-2-thioxo-2,3-dihydro-4(1H)-pyrimidinone, 5-benzyloxycarbonyl-6-[4-(3,4-dichlorobenzyl)-2-morpholinylamino]-3-methyl-1-phenyl-2-thioxo-2,3-dihydro-4(1H)-pyrimidinone, 6-[4-(p-trifluoromethylbenzyl)-2-morpholinylamino]-3-methyl-1-phenyl-5-(2-propoxycarbonyl)-2-thioxo-2,3-dihydro-4(1H)-pyrimidinone, 6-[4-(p-trifluoromethylbenzyl)-2-morpholinylamino]-5-methoxycarbonyl-3-methyl-1-phenyl-2-thioxo-2,3-dihydro-(1H)-pyrimidinone, 6-(4-benzyl-2-morpholinylmethylamino)-5-cyano-4-imino-1,3-dimethyl-3,4-dihydro-2(1H)-pyrimidinethione, 6-[4-(3,4-dichlorobenzyl)-2-morpholinylmethylamino]-5-cyano-4-imino-1,3-dimethyl-3,4-dihydro-2(1H)-pyrimidinethione, 5-cyano-6-[4-(p-trifluoromethylbenzyl)-2-morpholinylmethylamino]-4-imino-1,3-dimethyl-3,4-dihydro-2(1H)-pyrimidinethione, 5-cyano-4-imino-1,3-dimethyl-6-[4-(4-pyridylmethyl)-2-morpholinylmethylamino]-3,4-dihydro-2(1H)-pyrimidinethione, 1-[5-cyano-6-[4-(p-fluorobenzyl)-2-morpholinylmethylamino]-3-methyl-1-phenyl-2-thioxo-1,2,3,4-tetrahydropyrimidin-4-ylidene]-3-phenylurea, 1-[6-[4-(p-chlorobenzyl)-2-morpholinylmethylamino]-5-cyano-3-methyl-1-phenyl-2-thioxo-1,2,3,4-tetrahydropyrimidin-4-ylidene]-3-phenylurea, 1-[5-cyano-6-[4-(p-fluorobenzyl)-2-morpholinylmethylamino]-1,3-dimethyl-2-thioxo-1,2,3,4-tetrahydropyrimidin-4-ylidene]-3-methylurea, 1-[5-cyano-1,3-dimethyl-6-[4-(p-fluorobenzyl)-2-morpholinylmethylamino]-2-thioxo-1,2,3,4-tetrahydropyrimidin-4-ylidene]-3-phenylurea, 1-[5-cyano-6-[4-(p-fluorobenzyl)-2-morpholinylmethylamino]-3-methyl-1-phenyl-2-thioxo-1,2,3,4-tetrahydropyrimidin-4-ylidene]-3-isopropylurea, 4-acetylimino-5-cyano-3-methyl-6-[4-(p-fluorobenzyl)-2-morpholinylmethylamino]-1-phenyl-3,4-dihydro-2(1H)-pyrimidinethione, 6-[4-(p-chlorobenzyl)-2-morpholinylmethylamino]-5-cyano-4-imino-1,3-dimethyl-3,4-dihydro-2(1H)-pyrimidinethione, 6-[4-(biphenyl-4-ylmethyl)-2-morpholinylmethylamino]-5-cyano-4-imino-1,3-dimethyl-3,4-dihydro-2(1H)-pyrimidinethione, 5-cyano-4-imino-6-[4-(p-methoxybenzyl)-2-morpholinylmethylamino]-1,3-dimethyl-3,4-dihydro-2(1H)-pyrimidinethione, 5-ethoxycarbonyl-6-[4-(p-fluorobenzyl)-2-morpholinylmethylamino]-1,3-dimethyl-2-thioxo-2,3-dihydro-4(1H)-pyrimidinone, 1,3-diisobutyl-5-cyano-6-[4-(p-fluorobenzyl)-2-morpholinylmethylamino]-4-imino-3,4-dihydro-2(1H)-pyrimidinethione, 5-cyano-6-[4-(p-fluorobenzyl)-2-morpholinylmethylamino]-1-methyl-3-phenyl-2,4(1H,3H)-pyrimidinedione, 5-cyano-6-[4-(p-fluorobenzyl)-2-morpholinylmethylamino]-4-imino-1,3-dimethyl-3,4-dihydro-2(1H)-pyrimidinone, 5-cyano-6-[4-(p-fluorobenzyl)-2-morpholinylmethylamino]-3-methyl-1-phenyl-2-thioxo-2,3-dihydro-4(1H)-pyrimidinone, 5-cyano-6-[4-(p-fluorobenzyl)-2-morpholinylmethylamino]-4-imino-1-methyl-3-phenyl-3,4-dihydro-2(1H)-pyrimidinethione, 5-cyano-6-[1-(p-fluorobenzyl)-3-piperidylmethylamino]-4-imino-1,3-dimethyl-3,4-dihydro-2(1H)-pyrimidinethione, 5-cyano-4-imino-6-[1-(p-methoxybenzyl)-3-piperidylmethylamino]-1,3-dimethyl-3,4-dihydro-2(1H)-pyrimidinethione, 5-cyano-4-imino-6-[1-(3,4-dimethoxybenzyl)-3-piperidylmethylamino]-1,3-dimethyl-3,4-dihydro-2(1H)-pyrimidinethione, 5-cyano-1,3-dimethyl-6-[1-(p-methoxycarbonylbenzyl)-3-piperidylmethylamino]-4-imino-3,4-dihydro-2(1H)-pyrimidinethione, 5-cyano-4-imino-1,3-dimethyl-6-[1-(4-pyridylmethyl)-3-piperidylmethylamino]-3,4-dihydro-2(1H)-pyrimidinethione, 5-cyano-6-[1-(p-trifluoromethylbenzyl)-3-piperidylmethylamino]-4-imino-1,3-dimethyl-3,4-dihydro-2(1H)-pyrimidinethione, 5-cyano-6-[1-(p-chlorobenzyl)-3-piperidylmethylamino]-4-imino-1,3-dimethyl-3,4-dihydro-2(1H)-pyrimidinethione, 5-cyano-6-[1-(3,4-dichlorobenzyl)-3-piperidylmethylamino]-4-imino-1,3-dimethyl-3,4-dihydro-2(1H)-pyrimidinethione, 5-cyano-6-[1-(p-fluorobenzyl)-3-azetidinylamino]-4-imino-1,3-dimethyl-3,4-dihydro-2(1H)-pyrimidinethione, 5-cyano-6-[1-(p-fluorobenzyl)-4-piperidinylamino]-4-imino-1,3-dimethyl-3,4-dihydro-2(1H)-pyrimidinethione, 5-cyano-6-[4-(p-fluorobenzyl)-1-piperazinyl]-4-imino-1,3-dimethyl-3,4-dihydro-2(1H)-pyrimidinethione, 5-cyano-6-[2-[4-(p-fluorobenzyl)-1-piperazinyl]ethylamino]-4-imino-1,3-dimethyl-3,4-dihydro-2(1H)-pyrimidinethione, 5-cyano-6-[N-[2-[1-(p-fluorobenzyl)-2-piperidyl]ethyl]-N-methylamino]-4-imino-1,3-dimethyl-3,4-dihydro-2(1H)-pyrimidinethione, 5-cyano-6-[1-(p-fluorobenzyl)-4-piperidylmethylamino]-4-imino-1,3-dimethyl-3,4-dihydro-2(1H)-pyrimidinethione, 5-cyano-6-[1-(p-fluorobenzyl)-2-piperidylmethylamino]-4-imino-1,3-dimethyl-3,4-dihydro-2(1H)-pyrimidinethione, 5-cyano-4-imino-1,3-dimethyl-6-[4-[2-oxo-2-(1-pyrrolidinyl)ethyl]-1-piperazinyl]-3,4-dihydro-2(1H)-pyrimidinethione, 1-benzyl-5-cyano-6-[4-(p-fluorobenzyl)-1-piperazinyl]-4-imino-3-methyl-3,4-dihydro-2(1H)-pyrimidinethione, 5-cyano-6-[4-benzyloxy-3-(p-fluorobenzylamino)butylamino]-4-imino-1,3-dimethyl-3,4-dihydro-2(1H)-pyrimidinethione, 6-[2-(p-fluorobenzyl)-3aβ,5α,6aβ-octahydrocyclopenta[c]pyrrol-5-amino]-5-cyano-4-imino-1,3-dimethyl-3,4-dihydro-(1H)-pyrimidinethione, 6-[2-(p-fluorobenzyl)-3aβ,5α,6aβ-octahydrocyclopenta[c]pyrrol-5-amino]-5-cyano-4-imino-3-methyl-1-phenyl-3,4-dihydro-2(1H)-pyrimidinethione, 5-cyano-6-[5-(p-fluorophenyl)-2-hydroxy-4-azapentylamino]-4-imino-1,3-dimethyl-3,4-dihydro-2(1H)-pyrimidinethione, 5-cyano-6-[N-[5-p-fluorophenyl-4-(2-methoxyethyl)-4-azapentyl]-N-(2-methoxyethyl)amino]-4-imino-1,3-dimethyl-3,4-dihydro-2(1H)-pyrimidinethione, 5-cyano-1,3-dimethyl-6-[4-(p-fluorobenzyl)-4-aza-7-oxaoctylamino]-4-imino-3,4-dihydro-2(1H)-pyrimidinethione, 5-cyano-6-[7-(p-fluorophenyl)-3,6-diaza-1-heptylamino]-4-imino-1,3-dimethyl-3,4-dihydro-2(1H)-pyrimidinethione, 5-cyano-6-[7-(p-fluorophenyl)-6-aza-3-oxaheptylamino]-4-imino-1,3-dimethyl-3,4-dihydro-2(1H)-pyrimidinethione,
5-cyano-6-[5-(p-fluorophenyl)-4-azapentylamino]-4-imino-3,4-dihydro-1,3-dimethyl-2(1H)-pyrimidinethione,
5cyano-6-[6-(p-fluorophenyl)-5-azahexylamino]-4-imino-1,3-dimethyl-3,4-dihydro-2(1H)-pyrimidinethione,
5-cyano-6-[7-(p-fluorophenyl)-6-azaheptylamino]-4-imino-1,3-dimethyl-3,4-dihydro-2(1H)-pyrimidinethione,
5-cyano-6-[5-(p-fluorophenyl)-2-methoxy-4-azapentylamino]-4-imino-1,3-dimethyl-3,4-dihydro-2(1H)-pyrimidinethione,
5-cyano-6-[7-(p-fluorophenyl)-6-aza-3-oxaheptylamino]-1,3-dimethyl-2-thioxo-2,3-dihydro-4(1H)-pyrimidinone,
5-ethoxycarbonyl-6-[7-(p-fluorophenyl)-6-aza-3-oxaheptylamino]-1,3-dimethyl-2-thioxo-2,3-dihydro-4(1H)-pyrimidinone,
5-cyano-6-[cis-6-[N-(p-fluorobenzyl)-N-methylaminomethyl]-2-tetrahydropyranylmethylamino]-4-imino-1,3-dimethyl-3,4-dihydro-2(1H)-pyrimidinethione,
5-cyano-6-[trans-6-[N-(p-fluorobenzyl)-N-methylaminomethyl]-2-tetrahydropyranylmethylamino]-4-imino-1,3-dimethyl-3,4-dihydro-2(1H)-pyrimidinethione,
5-cyano-6-[trans-5-[N-(p-fluorobenzyl)-N-methylaminomethyl]-2-tetrahydrofuranylmethylamino]-4-imino-1,3-dimethyl-3,4-dihydro-2(1H)-pyrimidinethione,
5-cyano-6-[cis-5-[N-(p-fluorobenzyl)-N-methylaminomethyl]-2-tetrahydrofuranylmethylamino]-4-imino-1,3-dimethyl-3,4-dihydro-2(1H)-pyrimidinethione,
5-cyano-4-imino-6-[2-(3-indolyl)ethylamino]-1,3-dimethyl-3,4-dihydro-2(1H)-pyrimidinethione,
5-cyano-4-imino-1,3-dimethyl-6-isopropylamino-3,4-dihydro-(1H)-pyrimidinethione,
5-cyano-6-(p-fluorobenzylamino)-4-imino-1,3-dimethyl-3,4-dihydro-2(1H)-pyrimidinethione,
6-(p-fluorobenzyl)amino-5-cyano-1,3-dimethyl-4-benzylimino-3,4-dihydro-2(1H)-pyrimidinethione,
5-cyano-4-imino-1,3-dimethyl-6-methylthio-3,4-dihydro-2(1H)-pyrimidinethione,
5-cyano-1,3-dimethyl-6-methylthio-2-thioxo-2,3-dihydro-4(1H)-pyrimidinone,
5-methoxycarbonyl-3-methyl-6-methylthio-1-phenyl-2-thioxo-2,3-dihydro-4(1H)-pyrimidinone,
5-cyano-4-imino-3-methyl-6-methylthio-1-phenyl-3,4-dihydro-(1H)-pyrimidinethione,
3-methyl-6-methylthio-1-phenyl-5-(2-propoxycarbonyl)-2-thioxo-2,3-dihydro-4(1H)-pyrimidinone,
5-benzyloxycarbonyl-3-methyl-6-methylthio-1-phenyl-2-thioxo-2,3-dihydro-4(1H)-pyrimidinone,
5-n-butoxycarbonyl-3-methyl-6-methylthio-1-phenyl-2-thioxo-2,3-dihydro-4(1H)-pyrimidinone,
5-cyclohexyloxycarbonyl-3-methyl-6-methylthio-1-phenyl-2-thioxo-2,3-dihydro-4(1H)-pyrimidinone,
5-cyano-1,3-dimethyl-6-methylthio-2,4(1H,3H)-pyrimidinedione,
5-cyano-3-methyl-6-methylthio-1-phenyl-2,4(1H,3H)-pyrimidinedione,
1-(5-cyano-3-methyl-6-methylthio-1-phenyl-2-thioxo-1,2,3,4-tetrahydroprimidin-4-ylidene)-3-phenylurea,
1-(5-cyano-1,3-dimethyl-6-methylthio-2-thioxo-1,2,3,4-tetrahydroprimidin-4-ylidene)-3-methylurea,
1-(5-cyano-1,3-dimethyl-6-methylthio-2-thioxo-1,2,3,4-tetrahydroprimidin-4-ylidene)-3-phenylurea,
1-(5-cyano-3-methyl-6-methylthio-1-phenyl-2-thioxo-1,2,3,4-tetrahydroprimidin-4-ylidene)-3-isopropylurea,
1-acetylimino-5-cyano-3-methyl-6-methylthio-1-phenyl-3,4-dihydro-2(1H)-pyrimidinethione,
1-(5-cyano-6-methylthio-2-oxo-1,3-diphenyl-1,2,3,4-tetrahydroprimidin-4-ylidene)-3-phenylurea,
1-(5-cyano-1-methyl-6-methylthio-2-oxo-3-phenyl-1,2,3,4-tetrahydroprimidin-4-ylidene)-3-phenylurea,
5-cyano-6-[4-(p-fluorobenzyl)-3-morpholinylmethylamino]-4-imino-1,3-dimethyl-3,4-dihydro-2(1H)-pyrimidinethione.

The present compounds as described above have a noticeable gastrointestinal prokinetic activity as illustrated by the following examples, thus being useful as a therapeutic agent for digestive tract diseases.

The compounds of formula (I) may be converted, if desired, to the corresponding acid addition salts with pharmacologically acceptable acids. These acid addition salts fall in the scope of this invention. The acid addition salts include, for example, the salts with inorganic acids such as hydrochloric acid, hydrobromic acid, sulfuric acid, nitric acid, phosphoric acid and the like, or the salts with organic acids such as acetic acid, succinic acid, oxalic acid, malic acid, tartaric acid and the like.

The compounds represented by formula (I) when applied as drugs may be formulated into pharmaceutical preparations of various dosage forms. More specifically, the preparations may be orally administered in the form of tablets, sugar-coated tablets, soft capsules, hard capsules, solutions, emulsions or suspensions. The preparations may be parenterally administered in the form of injections.

These preparations can be prepared by adding conventional additives for formulation, for example, excipients, stabilizers, preservatives, solubilizers, wetting agents, emulsifiers, lubricants, sweetening agents, colorants, flavorings, isotonic agents, buffers, antioxidants and the like.

The route and dosage for administration of the present gastrointestinal prokinetic agents are not specifically limited and may be appropriately chosen depending upon various dosage forms, sex of patients, severity of the diseases to be treated, and a daily dose of the active ingredient is 0.001 mg to 1000 mg.

BEST MODE FOR CARRYING OUT THE INVENTION

This invention will be more fully illustrated by way of the following Preparation Examples and working Examples, and the Preparation Examples will explain some synthetic examples of the strating materials to prepare the present compounds, while the working Examples will explain some actual examples of the synthesis and application as drugs of the present compounds. These Preparation Examples and working Examples are given simply for the purpose of illustrating this invention and are not to be construed to limit this invention.

PREPARATION EXAMPLE 1 endo-7-Amino-9-[3-(p-fluorophenoxy)propyl]-3-oxa-9-azabicyclo[3.3.1]nonane

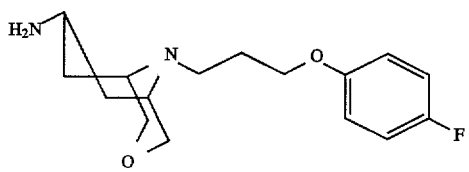

a) 9-[3-(p-Fluorophenoxy)propyl]-7-oxo-3-oxa-9-azabicyclo-[3.3.1]nonane

A solution of 2.5-dihydrofuran (3.06 g, 43.7 mmol) in methanol (100 ml) was cooled to −78° C. and ozone was aerated for one hour and 40 minutes. Then the reaction mixture was cooled with ice, platinum dioxide (0.1 g) was added and the mixture was stirred at room temperature under hydrogen atmosphere at ordinary pressure for one hour and 20 minutes. The platinum dioxide was filtered off and the filtrate was concentrated. The concentrate was added to an aqueous solution of disodium hydrogenphosphate (22.4 g) and citric acid (10.6 g)(1 liter), acetone dicarboxylic acid (6.38 g, 43.7 mmol) and 3-(p-fluorophenoxy)propylamine (7.39 g, 43.7 mmol) were added and the mixture was stirred for 12 hours. The reaction mixture was adjusted to a pH value of 12 by the addition of aqueous sodium hydroxide and then extracted with chloroform (500 ml×8). The organic layer was dried over potassium carbonate and concentrated under reduced pressure. The residue was purified by silica gel column chromatography (ethyl acetate) to give [3-(p-fluorophenoxy)propyl]-7-oxo-3-oxa-9-azabicyclo-[3.3.1]nonane (2.07 g) as a colorless oil. Yield=18%.

$^1$HNMR(CDCl$_3$)δ1.97(quint,J=6 Hz,2H), 2.31(d,J=16 Hz,2H), 2.67(dd,J=6 Hz,16 Hz,2H), 2.89(t,J=6 Hz,2H), 3.19 (d,J=6 Hz,2H), 3.72(d,J=11 Hz,2H), 3.77(d,J=11 Hz,2H), 4.05(t,J=6 Hz,2H), 6.83–6.86(m,2H), 6.94–7.00(m,2H)

IR(film) 2952, 2862, 1710, 1509, 1249, 1206, 790cm$^{-1}$
MS m/z 293 (M$^+$)

b) endo-7-Amino-9-[3-(p-fluorophenoxy)propyl]-3-oxa-9-azabicyclo[3.3.1]nonane

9-[3-(p-Fluorophenoxy)propyl]-7-oxo-3-oxa-9-azabicyclo[3.3.1]nonane (1.90 g, 7.33 mmol) was dissolved in ethanol (15 ml), pyridine (1.2 ml) and hydroxylamine hydrochloride (0.54 g, 7.69 mmol) were added and the mixture was heated under reflux for 4 hours. The reaction mixture was cooled to room temperature, water (1.5 ml) and potassium carbonate (3.0 g) were added and the mixture was stirred for one hour. Insolubles were recovered by filtration and the filtrate was concentrated to give a white solid (1.69 g). The solid (1.69 g) was placed into an autoclave and dissolved in ethanol (100 ml), ammonium acetate (5.5 g) and a catalytic amount of Raney nickel (W-5) were added and the mixture was stirred at 70° C. and 50 atmospheres for 6 hours. The reaction mixture was cooled to room temperature, the catalyst was filtered off, the filtrate was concentrated. To the residue was added an aqueous solution of sodium hydroxide (100 ml) and extracted with chloroform (150 ml×6). Insolubles were filtered off with Celite, the filtrate was washed with a saturated aqueous solution of sodium chloride and concentrated under reduced pressure to give the title compound (1.38 g) as a brown oil. Yield=86%.

$^1$HNMR(CDCl$_3$)δ1.36(d,J=15 Hz,2H), 1.86(quint, J=7 Hz,2H), 2.29(bs,2H), 2.34–2.41(m,2H), 2.66(bs,2H), 2.78(t, J=7 Hz,2H), 3.17(t,J=7 Hz,1H), 3.70(d,J=11 Hz,2H), 3.86 (d,J=11 Hz,2H), 4.00(t,J=7 Hz,2H), 6.81–6.86(m,2H), 6.93–7.28(m,2H)

IR(film) 2920, 2854, 1601, 1509, 1250, 1204, 830, 756cm$^{-1}$

PREPARATION EXAMPLE 2 exo-7-Amino-9-(p-fluorobenzyl)-3-oxa-9-azabicyclo[3.3.1]nonane

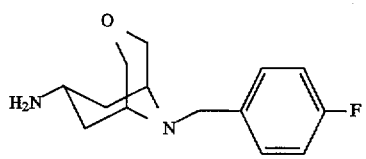

To a solution of crude 9-(p-fluorobenzyl)-3-oxa-9-azabicyclo[3.3.1]nona-7-one oxime (2.0 g, 7.6 mmol) in 1-pentanol (20 ml) was added metallic sodium (1.84 g, 80.0 mmol) portionwise over 20 minutes while heating under reflux and the mixture was stirred for 1.5 hours. After purified water (30 ml) was added to the reaction mixture under ice-cooling, the mixture was made acidic with conc. hydrochloric acid. The aqueous layer was washed with ethyl acetate (50 ml) and made strongly basic with 10% aqueous sodium hydroxide. Then, it was extracted with chloroform (50 ml×3) and the combined organic layer was dried over potassium carbonate and the solvent was distilled off under reduced pressure to give crude exo-7-amino-9-(p-fluorobenzyl)-3-oxa-9-azabicyclo[3.3.1]nonane (1.61 g). Yield=85%. This compound was used for the subsequent reaction without purification.

PREPARATION EXAMPLE 3

2-Aminomethyl-4-(p-chlorobenzyl)morpholine

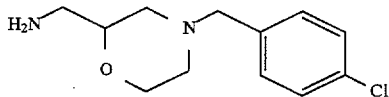

a) 2-(p-Chlorobenzylamino)ethanol

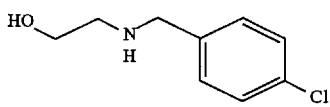

To a solution of 2-aminoethanol (62.30 g, 1.02 mol) in methanol (100 ml) was added p-chlorobenzyl chloride (32.85 g, 0.204 mol) and then sodium hydroxide (8.98 g, 0.224 mol) and the mixture was heated under reflux for 3 hours. After the methanol and 2-aminoethanol were distilled off under reduced pressure, the residue was extracted with chloroform and dried over anhydrous magnesium sulfate. The chloroform was distilled off to give 35.54 g of the title compound as an oily substance. Yield=94%.

$^1$HNMR(CDCl$_3$)δ1.30–2.00(bs,2H), 2.80(t,J=5 Hz,2H), 3.66(t,J=5 Hz,2H), 3.78(s,2H), 7.20–7.35(m,4H)

b) 4-(p-Chlorobenzyl)-2-chloromethylmorpholine

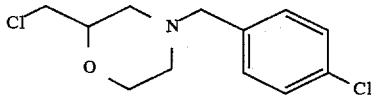

To 2-(p-chlorobenzylamino)ethanol (35.54 g, 0.19 mol) was added epichlorohydrin (45 ml, 0.57 mol) and the mixture was stirred at 60° C. for 2.5 hours. After the excess epichlorohydrin was distilled off, sulfuric acid (57 ml) was added and the mixture was heated at 150° C. for 30 minutes. The reaction mixture was poured into ice-water (500 ml) and made basic with 40% aqueous sodium hydroxide. After extracting with toluene, the extract was dried over anhydrous magnesium sulfate and the toluene was distilled off to give 26.82 g of the title compound as an oily substance.

¹HNMR(CDCl₃)δ2.00(t,J=11 Hz,1H), 2.20(dt,J=3 Hz,11 Hz,1H), 2.63(dd,J=2 Hz,11 Hz,1H), 2.82(d,J=11 Hz,1H), 3.48(s,2H), 3.40–3.95(m,5H), 7.20–7.37(m,4H)

c) 4-(p-Chlorobenzyl)-2-phthalimidomethylmorpholine

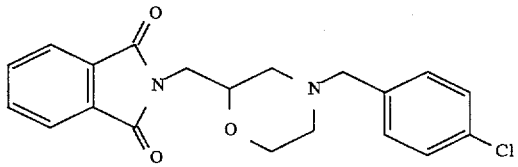

To a solution of 4-(p-chlorobenzyl)-2-chloromethylmorpholine (26.82 g, 0.103 mol) in DMF (150 ml) was added potassium phthalimide (21.00 g, 0.113 mol) and the mixture was heated under reflux for 1.5 hours. After completion of the reaction, the DMF was distilled off under reduced pressure and the residue was extracted with chloroform. The chloroform layer was dried over anhydrous magnesium sulfate and concentrated under reduced pressure. The crystal thus separated was recrystallized from chloroform-ethanol to give 21.40 g of the title compound. Yield=70%.

d) 2-Aminomethyl-4-(p-chlorobenzyl)morpholine

To a solution of 4-(p-chlorobenzyl)-2-phthalimidomethylmorpholine (20.28 g, 54.7 mmol) in ethanol (110 ml) was added hydrazine monohydrate (5.71 g, 0.114 mol) and the mixture was stirred at room temperature. 50 ml of dioxane was further added and the mixture was stirred at room temperature overnight. The crystal thus separated was filtered off and the filtrate was concentrated. The residue was dissolved in chloroform and the insolubles were filtered off. The filtrate was distilled off to give 9.31 g of the title compound as an oily substance. Yield=71%.

¹HNMR(CDCl₃)δ1.45–1.80(bs,2H), 1.87(t,J=10 Hz,1H), 2.16(dt,J=3 Hz,11 Hz,1H), 2.55–2.80(m,4H), 3.38–3.55(m,3H), 3.60–3.92(m,2H), 7.16–7.36(m,4H)

PREPARATION EXAMPLE 4

2-Aminomethyl-4-(p-fluorobenzyl)morpholine

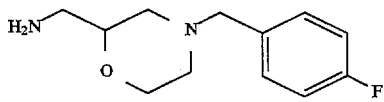

This compound was synthesized from p-fluorobenzyl chloride according to the same process as described in the Preparation Example 3.

¹HNMR(CDCl₃)δ1.42–1.70(br,2H), 1.87(t,J=10 Hz,1H), 2.15(dt,J=3 Hz,11 Hz,1H), 2.60–2.78(m,4H), 3.38–3.55(m,3H), 3.67(dt,J=2 Hz,11 Hz,1H), 3.83–3.92(m,1H), 7.00(t,J=9 Hz,2H), 7.23–7.35(m,2H)

PREPARATION EXAMPLE 5

2-Aminomethyl-4-(p-trifluoromethylbenzyl)morpholine

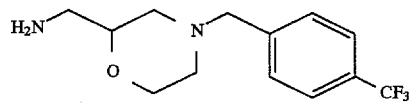

a) 3-Benzyl-6-chloro-3-azahexane-1,5-diol

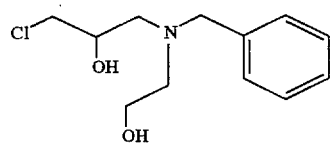

To a solution of N-benzylethanolamine (100 g, 0.66 mol) in toluene-ethanol (5/1, 600 ml) was added dropwise epichlorohydrin (62 ml, 0.79 mol) under ice-cooling over 20 minutes and then allowed to rise to room temperature. The mixture was stirred for 24 hours. The solvent was distilled off from the reaction mixture under reduced pressure and the residue was used for the subsequent reaction without purification.

b) 4-Benzyl-2-chloromethylmorpholine

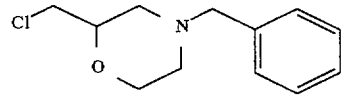

To 3-benzyl-6-chloro-3-azahexane-1,5-diol (164 g) was added dropwise under ice-cooling over 30 minutes conc. sulfuric acid (205 ml, 1.99 mol) in the absence of a solvent and allowed to rise to room temperature and stirred for 25 minutes. The reaction mixture was heated at 150° C. for 45 minutes. After cooling, ice-water (1000 ml) was added to the reaction mixture under ice-cooling and then 50% aqueous sodium hydroxide (1000 ml) was added dropwise over one hour. After insolubles were filtered off, the filtrate was extracted with chloroform (1000 ml×3). The organic layer was washed successively with purified water (1000 ml) and a saturated aqueous solution of sodium chloride (1000 ml), dried over potassium carbonate and the solvent was distilled off under reduced pressure. The residue was chromatographed over silica gel and the fraction from ethyl acetate-hexane (1/6) gave 4-benzyl-2-chloromethylmorpholine (107.25 g) as a colorless oil. A total yield of the two steps=72%.

¹HNMR(CDCl₃)δ2.01(t,J=10 Hz,1H), 2.20(dt,J=3 Hz,11 Hz,1H), 2.65(ddd,J=2 Hz,4 Hz,12 Hz, 1H), 2.84(dt,J=1 Hz, 11 Hz,1H), 3.43–3.56(m,2H), 3.52(s,2H), 3.65–3.79(m,2H), 3.90(ddd,J=2 Hz,3 Hz,11 Hz,1H), 7.19–7.39(m,5H)

c) 4-Benzyl-2-phthalimidomethylmorpholine

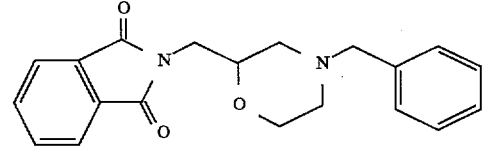

To a solution of 4-benzyl-2-chloromethyl-morpholine (43 g, 0.19 mol) in 500 ml of dimethylformamide was added potassium phthalimide (37 g, 0.20 mol) and the mixture was stirred at 100° C. for 16 hours. After insolubles were filtered off, the solvent was distilled off from the filtrate under reduced pressure to give crude 4-benzyl-2-phthalimidomethylmorpholine (70 g). This compound was used for the subsequent reaction without purification.

d) 2-Aminomethyl-4-benzylmorpholine

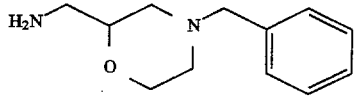

To a solution of crude 4-benzyl-2-phthalimidomethylmorpholine (64 g) in ethanol (500 ml) was added hydrazine monohydrate (18 ml, 0.57 mol) and the mixture was heated under reflux for 2 hours. After cooling, 10% aqueous sodium hydroxide (200 ml) was added to dissolve insolubles and the ethanol was distilled off under reduced pressure. The aqueous layer was extracted with chloroform (200 ml×3), the combined organic layer was dried over potassium carbonate and the solvent was distilled off to give crude 2-aminomethyl-4-benzylmorpholine (42.97 g). This compound was used for the subsequent reaction without purification.

e) 2-(N-Acetylaminomethyl)-4-benzylmorpholine

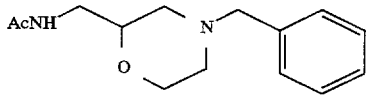

To a solution of crude 2-aminomethyl-4-benzylmorpholine (48 g) in toluene (400 ml) was added pyridine (24.5 ml, 0.303 mol) and then acetic anhydride (26.4 ml, 0.280 mol) was added dropwise under ice-cooling over 10 minutes and then allowed to rise to room temperature and the mixture was stirred for one hour. To the reaction mixture was added aqueous saturated sodium hydrogen carbonate (200 ml) under ice-cooling and then 10% aqueous sodium hydroxide was added until the mixture became strongly basic. The reaction mixture was extracted with ethyl acetate (200 ml×3) and the combined organic layer was washed with aqueous saturated sodium chloride (200 ml). The organic layer was dried over potassium carbonate and the solvent was distilled off under reduced pressure. The residue was recrystallized from ethyl acetate-hexane (1/1) to give 2-(N-acetylaminomethyl)-4-benzylmorpholine (25.93 g). A total yield of 3 steps=56%.

$^1$HNMR(CDCl$_3$)δ1.90(t,J=10 Hz,1H), 1.98(s,3H), 2.15 (dt,J=3 Hz,15 Hz,1H), 2.65(d,J=12 Hz,1H), 2.72(d,J=11 Hz,1H), 3.01–3.18(m,1H), 3.41–3.58(m,2H), 3.49(s,2H), 3.58–3.72(m,2H), 3.84(ddd,J=1 Hz,3 Hz,11 Hz,1H), 5.75–5.90(br,1H), 7.18–7.39(m,5H)

f) 2-(N-Acetylaminomethyl)morpholine

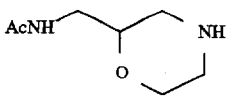

In a solution of 2-(N-acetylaminomethyl)-4-benzylmorpholine (20 g, 80.7 mmol) in ethanol-acetic acid (20/1, 210 ml) was suspended 2.0 g of 10% palladium-carbon and the mixture was stirred at 60° C. under hydrogen stream for 22 hours. The reaction mixture was filtered with Celite, the solvent was distilled off from the filtrate under reduced pressure to give crude 2-(N-acetylaminomethyl) morpholine (15.62 g). Yield=100%. This compound was used for the subsequent reaction without purification.

g) 2-(N-Acetylaminomethyl)-4-(p-trifluoromethylbenzyl) morpholine

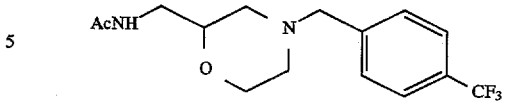

To a solution of crude 2-(N-acetylaminomethyl) morpholine (7.0 g) in methyl ethyl ketone (100 ml) were added successively potassium carbonate (82.7 g, 0.598 mol), potassium iodide (497 mg, 2.99 mmol) and p-trifluorobenzyl bromide (11.1 ml, 71.8 mmol) and the mixture was heated under reflux for 2 hours. The reaction mixture was filtered with Celite and the solvent was distilled off from the filtrate under reduced pressure. The residue was dissolved in chloroform (150 ml) and washed with aqueous saturated sodium chloride (50 ml). The organic layer was dried over potassium carbonate and the solvent distilled off under reduced pressure to give crude 2-(N-acetylaminomethyl)-4-(p-trifluoromethylbenzyl)morpholine (17.06 g). This compound was used for the subsequent reaction without purification.

h) 2-Aminomethyl-4-(p-trifluoromethylbenzyl)morpholine

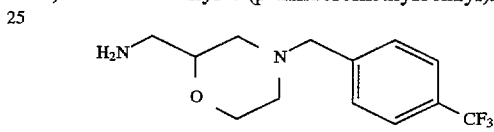

A solution of crude 2-(N-acetylaminomethyl)-4-(p-trifluoromethylbenzyl)morpholine (17.06 g) in 10% aqueous hydrochloric acid (200 ml) was heated under reflux for 3 hours. After cooling, the reaction mixture was made basic by the addition of 50% aqueous sodium hydroxide (100 ml) and then extracted with chloroform (100 ml×3). The combined organic layer was dried over potassium carbonate and the solvent was distilled off under reduced pressure to give crude 2-aminomethyl-4-(p-trifluoromethylbenzyl) morpholine. A total yield of 2 steps=100%. This compound was used for the subsequent reaction without purification.

PREPARATION EXAMPLE 6

2-Aminomethyl-4-(p-methoxybenzyl)morpholine

This compound was synthesized from p-methoxybenzyl chloride in the same manner as in Preparation Examples 5g–5h.

This compound was used for the subsequent reaction without purification.

2-Acetylaminomethyl-4-(p-methoxybenzyl)morpholine $^1$HNMR(CDCl$_3$)δ1.87(t,J=11 Hz,1H), 1.99(s,3H), 2.12 (dt,J=3 Hz, 11 Hz,1H), 2.60–2.76(m,2H), 3.04–3.14(m,1H), 3.43(s,2H), 3.45–3.89(m,4H), 3.80(s,3H), 5.75–5.90(br,1H), 6.85(d,J=9 Hz,2H), 7.20(d,J=9 Hz,2H)

PREPARATION EXAMPLE 7

2-Aminomethyl-4-(biphenyl-4-ylmethyl)morpholine

This compound was synthesized from 4-(chloromethyl) biphenyl in the same manner as in Preparation Examples 5g–5h.

$^1$HNMR(CDCl$_3$)δ1.20–1.55(br,2H), 1.91(t,J=11 Hz,1H), 2.20(dt,J=3 Hz,11 Hz,1H), 2.60–2.79(m,4H), 3.41–3.60(m, 3H), 3.65–3.94(m,2H), 7.29–7.50(m,5H), 7.50–7.65(m,4H)

Similarly, the following compounds were synthesized.

2-Aminomethyl-4-(3,4-dichlorobenzyl)morpholine

2-Aminomethyl-4-(4-pyridylmethyl)morpholine

PREPARATION EXAMPLE 8

3-Aminomethyl-1-(3,4-dimethoxybenzyl)piperidine

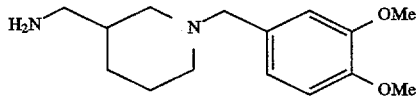

a) 3,4-Dimethoxybenzyl alcohol

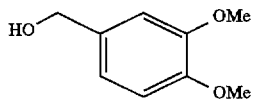

To a solution of 3,4-dimethoxybenzaldehyde (5.00 g, 0.030 mol) in methanol (20 ml) was added slowly under ice-cooling sodium borohydride (0.6 g, 0.016 mol) and the mixture was stirred at room temperature for one hour. After completion of the reaction, the methanol was distilled off and extracted with chloroform. After drying over anhydrous magnesium sulfate, the chloroform was distilled off to give 4.96 g of the title compound as an oily substance. Yield= 98%.

b) 3,4-Dimethoxybenzyl chloride

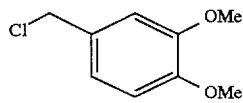

To 3,4-dimethoxybenzyl alcohol (4.96 g, 0.029 mol) was added thionyl chloride (6.45 ml, 0.088 mol) and the mixture was heated under reflux for 20 minutes. The reaction mixture was poured into ice-water and extracted with chloroform. After drying over anhydrous magnesium sulfate and decoloring with active charcoal, the solvent was distilled off to give 5.50 g of the title compound as an oily substance. Yield=100%.

$^1$HNMR(CDCl$_3$)δ3.89(s,3H), 3.90(s,3H), 4.57(s,2H), 6.83(d,J=8 Hz,1H), 6.90–6.95(m,2H)

c) 3-Hydroxymethyl-1-(3,4-dimethoxybenzyl)piperidine

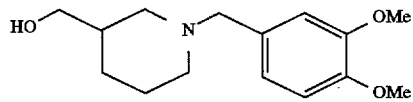

To 3,4-dimethoxybenzyl chloride (5.60 g, 0.03 mol) was added 3-(hydroxymethyl)piperidine (3.53 g, 0.03 mol) and the mixture was stirred. After completion of the exothermic reaction, the mixture was dissolved in methanol (40 ml) and sodium hydroxide (1.6 g) was added and stirred for 2 hours. After the methanol was distilled off, it was extracted with chloroform and dried over anhydrous magnesium sulfate. The chloroform was distilled off and purified by silica gel column chromatography. The fraction with chloroform-methanol (10/1) gave 4.78 g of the title compound as an oily substance. Yield=61%.

$^1$HNMR(CDCl$_3$)δ1.17–1.32(m,1H), 1.50–1.93(m,5H), 2.06–2.33(m,2H), 2.45–2.80(m,2H), 3.44(d,J=19 Hz,1H), 3.45(d,J=19 Hz,1H), 3.57(dd,J=6 Hz,11 Hz,1H), 3.66(dd, J=5 Hz,11 Hz,1H), 3.87(s,3H), 3.89(s,3H), 6.81(s,2H), 6.89 (s,1H)

d) 3-Chloromethyl-1-(3,4-dimethoxybenzyl)piperidine

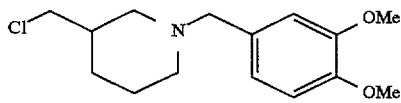

To 3-hydroxymethyl-1-(3,4-dimethoxybenzyl)piperidine (5.79 g, 0.022 mol) was added dropwise slowly thionyl chloride (4.77 ml, 0.066 mol). The mixture was stirred at room temperature for 2 hours, poured into ice-water and neutralized with sodium hydrogen carbonate. Extraction with chloroform was made under basic condition, the extract was dried over anhydrous magnesium sulfate and then the chloroform was distilled off to give 5.67 g of the title compound as an oily substance. Yield=92%.

$^1$HNMR(CDCl$_3$)δ1.06–1.21(m,1H), 1.48–2.10(m,6H), 2.62–2.93(m,2H), 3.33–3.56(m,4H), 3.87(s,3H), 3.89(s,3H), 6.81(s,2H), 6.90(s,1H)

e) 3-Phthalimidomethyl-1-(3,4-dimethoxybenzyl)piperidine

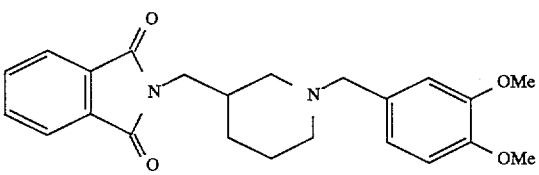

This compound was synthesized from 3-chloromethyl-1-(3,4-dimethoxybenzyl)piperidine according to the same process as in Preparation Example 3c. Yield=92%.

$^1$HNMR(CDCl$_3$)δ1.00–1.16(m,1H), 1.44–2.19(m,6H), 2.58–2.79(m,2H), 3.35(d,J=13 Hz,1H), 3.45(d,J=13 Hz,1H), 3.57(dd,J=7 Hz,14 Hz,1H), 3.63(dd,J=7 Hz,14 Hz,1H), 3.85 (s,3H), 3.89(s,3H), 6.73–6.82(m,2H), 6.87(s,1H), 7.71(dd, J=3 Hz,5 Hz,2H), 7.83(dd,J=3 Hz,5 Hz, 2H)

f) 3-Aminomethyl-1-(3,4-dimethoxybenzyl)piperidine

This compound was synthesized from 3-phthalimidomethyl-1-(3,4-dimethoxybenzyl)piperidine according to the same process as in Preparation Example 3d. Yield=100%.

$^1$HNMR(CDCl$_3$)δ0.86–1.00(m,1H), 1.29–2.10(m,8H), 2.56(d,J=6 Hz,2H), 2.72–2.90(m,2H), 3.41(d,J=13 Hz,1H), 3.45(d,J=13 Hz,1H), 3.87(s,3H), 3.89(s,3H), 6.81(s,2H), 6.89(s,1H)

PREPARATION EXAMPLE 9

3-Aminomethyl-1-(p-methoxycarbonylbenzyl)piperidine

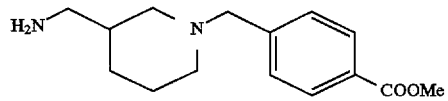

3-Phthalimidomethyl-1-(p-methoxycarbonylbenzyl) piperidine was synthesized from p-methoxycarbonylbenzaldehyde according to the same process as in Preparation Examples 8a–8e.

$^1$HNMR(CDCl$_3$)δ1.00–1.15(m,1H), 1.45–1.60(m,1H), 1.63–1.74(m,2H), 1.87–2.20(m,3H), 2.58–2.77(m,2H), 3.46 (d,J=14 Hz,1H), 3.55(d,J=14 Hz,1H), 3.57(dd,J=7 Hz,14 Hz, 1H), 3.63(dd,J=7 Hz,14 Hz,1H), 3.90(s,3H), 7.37(d,J=8 Hz,1H), 7.71(dd,J=3 Hz,5 Hz,2H), 7.83(dd,J=3 Hz,5 Hz,2H), 7.95(d,J=8 Hz,1H)

The 3-phthalimidomethyl-1-(p-methoxycarbonylbenzyl) piperidine thus obtained (13.81 g, 0.0352 mol) was dissolved in 2-propanol (70 ml), hydrazine monohydrate (1.76 g, 0.0352 mol) was added and then synthesized according to the same process as in Preparation Example 8f. Yield=16%.

$^1$HNMR(CDCl$_3$)δ1.00–1.20(m,1H), 1.43–2.20(m,8H), 2.54–2.89(m,4H), 3.44–3.63(m,2H), 3.90(s,3H), 7.37(d,J=8 Hz,2H), 7.96(d,J=8 Hz,2H)

PREPARATION EXAMPLE 10

3-Aminomethyl-1-(p-methoxybenzyl)piperidine

This compound was synthesized from p-methoxybenzyl chloride in the same manner as in Preparation Examples 8c–8f.

$^1$HNMR(CDCl$_3$)δ0.83–0.97(m,1H), 1.43–1.99(m,8H), 2.55(d,J=6 Hz,2H), 2.72–2.90(m,2H), 3.42(d,J=13 Hz,1H), 3.45(d,J=13 Hz,1H), 3.80(s,3H), 6.85(d,J=8 Hz,2H), 7.22(d, J=8 Hz,2H)

PREPARATION EXAMPLE 11

3-Aminomethyl-1-(p-fluorobenzyl)piperidine

This compound was synthesized from p-fluorobenzyl chloride in the same manner as in Preparation Examples 8c–8f.

$^1$HNMR(CDCl$_3$)δ0.83–0.97(m,1H), 1.00–1.99(m,8H), 2.55(d,J=6 Hz,2H), 2.68–2.90(m,2H), 3.43(d,J=13 Hz,1H), 3.46(d,J=13 Hz,1H), 6.94–7.03(m,2H), 7.22–7.31(m,2H)

PREPARATION EXAMPLE 12

3-Aminomethyl-1-(p-fluorobenzyl)piperidine

This compound was synthesized from p-fluorobenzyl chloride and 2-(hydroxymethyl)piperidine in the same manner as in Preparation Examples 8c–8f.

$^1$HNMR(CDCl$_3$)δ1.30–1.80(m,8H), 2.24–2.37(m,1H), 2.47–2.64(m,1H), 2.70–3.05(m,3H), 3.21(d,J=13 Hz,1H), 3.98(d,J=13 Hz,1H), 6.95–7.05(m,2H), 7.24–7.35(m,2H)

PREPARATION EXAMPLE 13 a) 3-Hydroxymethyl-1-(4-pyridylmethyl)piperidine

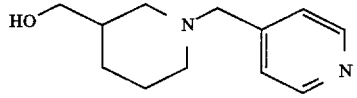

To a solution of 3-hydroxymethylpiperidine (5.0 g, 43 mmol) in methyl ethyl ketone (50 ml) were added successively potassium carbonate (60 g, 0.43 mol), sodium iodide (1.30 g, 8.68 mmol), 4-chloromethylpyridine hydrochloride (8.54 g, 52.1 mmol) and the mixture was heated under reflux for 8 hours. The reaction mixture was filtered with Celite and the solvent was distilled off from the filtrate under reduced pressure. The residue was chromatographed using silica gel column and the fraction from methanol-chloroform (1/20) gave 3-hydroxymethyl-1-(4-pyridylmethyl)piperidine (8.29 g). Yield=93%.

$^1$HNMR(CDCl$_3$)δ1.02–1.25(m,1H), 1.48–1.90(m,4H), 1.95–2.40(m,3H), 2.50–2.70(m,1H), 2.80(d,J=8 Hz,1H), 3.48(s,2H), 3.53(dd,J=6 Hz,10 Hz,1H), 3.62(dd,J=5 Hz,11 Hz,1H), 7.26(d,J=8 Hz,2H), 8.52(dd,J=1 Hz,4 Hz,2H)

Similarly, the following compounds were obtained.

1-(p-Chlorobenzyl)-3-hydroxymethylpiperidine

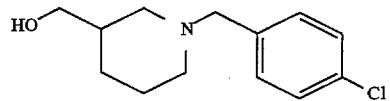

$^1$HNMR(CDCl$_3$)δ1.08–1.25(m,1H), 1.45–1.62(m,1H), 1.63–1.84(m,3H), 1.95–2.10(brm,1H), 2.11–2.21(brm,1H), 2.22–2.62(brm,2H), 2.76(d,J=11 Hz,1H), 3.50(s,2H), 3.49 (dd,J=4 Hz,10 Hz,1H), 3.59(dd,J=5 Hz,11 Hz,1H), 7.05–7.32(m,4H)

1-(p-Trifluoromethylbenzyl)-3-hydroxymethylpiperidine

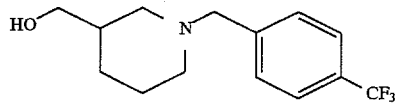

$^1$HNMR(CDCl$_3$-CD$_3$OD)δ0.92–1.09(m,1H), 1.50–1.65 (m,1H), 1.66–1.93(m,4H), 2.52–2.85(brm,2H), 2.86–3.01 (m,1H), 3.28–3.61(m,2H), 3.40(s,2H), 7.45(d,J=8 Hz,2H), 7.58(d,J=8 Hz, 2H)

1-(3,4-Dichlorobenzyl)-3-hydroxymethylpiperidine

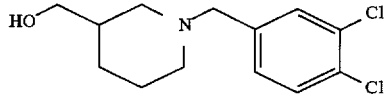

$^1$HNMR(CDCl$_3$)δ1.02–1.21(m,1H), 1.49–1.64(m,1H), 1.64–1.86(m,3H), 1.99(brt,J=9 Hz,1H), 2.12(brt,J=10 Hz,1H), 2.15–2.41(brm,1H), 2.54–2.68(m,1H), 2.79(d,J=9 Hz,1H), 3.43(s,2H), 3.52(dd,J=6 Hz,10 Hz,1H), 3.61(dd,J=5 Hz,11 Hz,1H), 7.16(dd,J=2 Hz,8 Hz,1H), 7.37(d,J=8 Hz,1H), 7.41(d,J=2 Hz,1H)

b) 3-Aminomethyl-1-(p-chlorobenzyl)piperidine

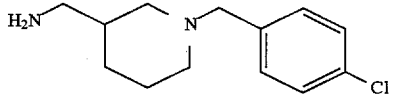

To a solution of 1-(p-chlorobenzyl)-3-hydroxymethyl piperidine (4.0 g, 19 mmol) in THF (40 ml) were added successively triphenylphosphine (5.60 g, 21.3 mmol), phthalimide (3.14 g, 21.4 mmol) and diethyl azodicarboxylate (3.4 ml, 21 mmol) under ice-cooling and the mixture was stirred for 1.5 hours. The solvent was distilled off from the reaction mixture under reduced pressure to give 10.52 g of crude 1-(p-chlorobenzyl)-3-phthalimidomethylpiperidine. This compound was used for the subsequent reaction without purification.

To a solution of 10.52 g of the crude 1-(p-chlorobenzyl)-3-phthalimidomethylpiperidine in ethanol (100 ml) was added hydrazine monohydrate (1.8 ml, 58 mmol) and the mixture was heated under reflux for 2 hours. After cooling, 10% aqueous sodium hydroxide (200 ml) was added to dissolve insolubles and the ethanol was distilled off under reduced pressure. The aqueous layer was extracted with chloroform (150 ml×3) and then the combined organic layer was then extracted with 10% aqueous hydrochloric acid (150 ml×3). The combined aqueous hydrochloric acid layer was washed with chloroform (100 ml). 10% aqueous sodium hydroxide was added until it became strongly basic and then extracted with chloroform (100 ml×3). The combined organic layer was dried over potassium carbonate and the solvent was distilled off under reduced pressure to give crude 3-aminomethyl-1-(p-chlorobenzyl)piperidine (3.93 g). A total yield of two steps=92%. This compound was used for the subsequent reaction without purification.

Similarly, the following compounds were obtained:
3-Aminomethyl-1-(4-pyridylmethyl)piperidine
3-Aminomethyl-1-(p-trifluoromethylbenzyl)piperidine
3-Aminomethyl-1-(3,4-dichlorobenzyl)piperidine.

PREPARATION EXAMPLE 14

4-Aminomethyl-1-(p-fluorobenzyl)piperidine

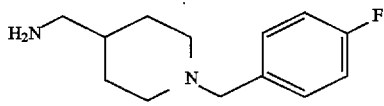

a) Methyl isonipecotinate

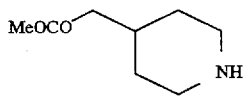

To a solution of isonipecotic acid (20.0 g, 0.155 mol) in methanol (350 ml) was added sulfuric acid (11.3 ml, 0.142 mol) and the mixture was heated under reflux for 29 hours. The methanol was distilled off, water was added and the mixture was neutralized with sodium hydrogencarbonate. It was extracted with ethyl acetate and dried over anhydrous magnesium sulfate and the solvent was distilled off to give 7.92 g of the title compound. Yield=36%.

$^1$HNMR(CDCl$_3$)δ1.61(dq,J=4 Hz,12 Hz,2H), 1.89(dd, J=4 Hz,12 Hz,2H), 2.43(tt,J=4 Hz,12 Hz,2H), 2.64(dt,J=4 Hz,12 Hz,2H), 3.10(td,J=4 Hz,12 Hz,2H), 3.68(s,3H)

b) Methyl 1-(p-fluorobenzyl)isonipecotinate

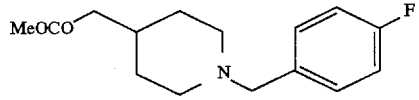

To methyl isonipecotinate (3.05 g, 21.3 mmol) was added p-fluorobenzyl chloride (3.07 g, 21.3 mmol) and the mixture was stirred with a glass rod. After completion of the exothermic reaction, it was dissolved in methanol (15 ml), sodium hydroxide (1.0 g) was added and the mixture was stirred for 2 hours. After the methanol was distilled off, it was extracted with chloroform and dried over anhydrous magnesium sulfate. After the chloroform was distilled off, it was purified by silica gel column chromatography and the fraction from chloroform-methanol (10/1) gave 2.57 g of the title compound as an oily substance. Yield=48%.

$^1$HNMR(CDCl$_3$)δ1.75(dq,J=4 Hz,12 Hz,2H), 1.87(dd, J=4 Hz,12 Hz, 2H), 2.01(dt,J=4 Hz,12 Hz,2H), 2.29(tt,J=4 Hz,12 Hz,1H), 2.82(td,J=4 Hz,12 Hz,2H), 3.43(s,2H), 3.67 (s,3H), 6.94–7.04(m,2H), 7.23–7.31(m,2H)

c) 1-(p-Fluorobenzyl)-4-hydroxymethylpiperidine

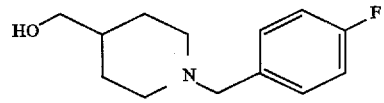

Lithium aluminium hydride (1.13 g, 30 mmol) was suspended in ether (250 ml) and a solution of methyl 1-(p-fluorobenzyl)isonipecotinate (2.51 g, 10 mmol) in ether (20 ml) was slowly added dropwise under stirring. The mixture was stirred at room temperature for 3 days, water (1.1 ml), 40% aqueous sodium hydroxide (1.1 ml) and water (3.4 ml) were in turn added and the mixture was stirred for 3 hours. The alumina separated out was filtered off and the ether was distilled off to give 2.13 g of the title compound as an oily substance. Yield=96%.

$^1$HNMR(CDCl$_3$)δ1.27(dq,J=4 Hz,12 Hz,2H), 1.30–1.80 (m,2H), 1.70(d,J=13 Hz,2H), 1.94(t,J=12 Hz,2H), 2.88(d,J= 12 Hz,2H), 3.45(s,2H), 3.49(d,J=6 Hz,2H), 6.92–7.05(m, 2H), 7.23–7.35(m,2H)

d) 4-Aminomethyl-1-(p-fluorobenzyl)piperidine

This compound was synthesized from 1-(p-fluorobenzyl)-4-hydroxymethylpiperidine in the same manner as in Preparation Examples 8d–8f.

$^1$HNMR(CD$_3$OD)δ1.17–1.37(m,2H), 1.37–1.52(m,1H), 1.76(t,J=13 Hz,2H), 2.01(dt,J=2 Hz,12 Hz,2H), 2.61(d,J=7 Hz,2H), 2.91(d,J=12 Hz,2H), 3.50(s,2H), 7.00–7.09(m,2H), 7.27–7.36(m,2H)

PREPARATION EXAMPLE 15

2-(2-Methylaminoethyl)-1-(p-fluorobenzyl)piperidine

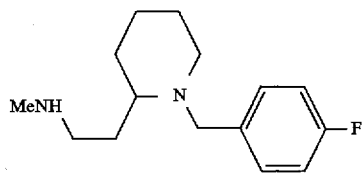

a) 5-Hydroxypentyl p-toluenesulfonate

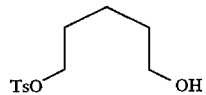

To a solution of 1,5-pentanediol (30 g, 0.29 mol) in dichloromethane/DMF (15/1, 320 ml) were added triethylamine (38.1 ml, 0.274 mol), dimethylaminopyridine (7.04 g, 57.6 mmol) and p-toluenesulfonic acid chloride (49.42 g, 0.259 mol) were in turn added at –30° C. and the mixture was stirred for 2.5 hours. To the reaction mixture was added purified water (200 ml) and the aqueous layer was extracted with chloroform (150 ml×3). The combined organic layer was washed succcessively with 5% aqueous hydrochloric acid (200 ml), saturated aqueous sodium hydrogen carbonate (200 ml) and saturated aqueous sodium chloride (200 ml), dried over anhydrous magnesium sulfate and the solvent was distilled off. The residue was chromatographed over silica gel and the fraction from ethyl acetate-hexane (1/1) gave 19.65 g of 5-hydroxypentyl p-toluenesulfonate. Yield=26%.

$^1$HNMR(CDCl$_3$)δ1.30–1.58(m,5H), 1.67(quint,J=6 Hz,2H), 2.44(s,3H), 3.60(t,J=8 Hz,2H), 4.04(t,J=8 Hz,2H), 7.35(d,J=9 Hz,2H), 7.78(d,J=9 Hz,2H)

b) Ethyl 7-(p-toluenesulfonyloxy)-2-heptenoate

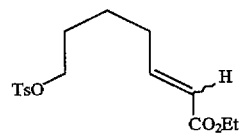

To a solution of oxalic chloride (19.9 ml, 0.229 mol) in dichloromethane (400 ml) was added dimethyl sulfoxide (32.4 ml, 0.457 mol) at −78° C. and the mixture was stirred for 15 minutes. To the reaction mixture was added dropwise over 30 minutes a solution of 5-hydroxypentyl p-toluenesulfonate (19.65 g, 76.16 mmol) in dichloromethane (50 ml) and the mixture was stirred for 15 minutes and then triethylamine (95.5 ml, 0.686 mol) was added dropwise over 10 minutes and allowed to rise to room temperature. After chloroform (200 ml) was added to the reaction mixture, it was washed successively with 5% aqueous hydrochloric acid (200 ml), saturated aqueous sodium hydrogen carbonate (200 ml) and saturated aqueous sodium chloride (200 ml), dried over anhydrous magnesium sulfate and the solvent was distilled off under reduced pressure to give 7-(p-toluenesulfonyloxy)-2-heptenal (24.5 g). This aldehyde was used for the subsequent reaction without purification.

To a suspension of sodium hydride (3.35 g, 83.78 mmol) in THF (100 ml) was added under ice-cooling ethyl diethylphosphonoacetate (18.1 ml, 91.4 mmol) and the mixture was stirred for 20 minutes. A solution of the aldehyde (19.5 g, 76.2 mmol) in THF (200 ml) was added dropwise over 30 minutes, the mixture was allowed to rise to room temperature and stirred for 17 hours. Purified water (150 ml) was added to the reaction mixture under ice-cooling and the aqueous layer was extracted with diethyl ether (150 ml×3). The combined organic layer was washed in turn with purified water (200 ml) and saturated aqueous sodium chloride (200 ml), dried over anhydrous magnesium sulfate and the solvent was distilled off under reduced pressure. The residue was chromatographed using silica gel column and the fraction from ethyl acetate-hexane (1/4) gave the title compound (14.0 g) as an E/Z mixture. A total yield of two steps=56%. A part of this product was purified in the same manner as above to afford (Z)-ethyl 7-(p-toluenesulfonyloxy)-2-heptenoate from the low polar fraction and (E)-ethyl 7-(p-toluenesulfonyloxy)-2-heptenoate from the high polar fraction and then their spectrum data were measured. (E)-Ethyl 7-(p-toluenesulfonyloxy)-2-heptenoate $^1$HNMR(CDCl$_3$)δ1.29(t,J=7 Hz,3H), 1.40–1.54(m,2H), 1.57–1.74(m,2H), 2.16(dd,J=1 Hz,7 Hz,2H), 2.46(s,3H), 4.03(t,J=6 Hz,2H), 4.18(q,J=7 Hz,2H), 5.77(d,J=16 Hz,1H), 6.87(dt,J=7 Hz,16 Hz,1H), 7.35(d,J=8 Hz,2H), 7.79(d,J=8 Hz,2H)

IR(film) 1720, 1360, 1180cm$^{-1}$ (Z) Ethyl 7-(p-toluenesulfonyloxy)-2-heptenoate $^1$HNMR(CDCl$_3$)δ1.29(t,J=7 Hz,3H), 1.41–1.59(m,2H), 1.60–1.75(m,2H), 2.45(s,3H), 2.54–2.69(m,2H), 4.03(t,J=6 Hz,2H), 4.18(q,J=7 Hz,2H), 5.76(d,J=16 Hz,1H), 6.86(dt, J=7 Hz,16 Hz,1H), 7.35(d,J=8 Hz,2H), 7.79(d,J=8 Hz,2H)

IR(film) 1719, 1649, 1365, 1179cm$^{-1}$ c) Ethyl 2-[1-(p-fluorobenzyl)-2-piperidyl]acetate

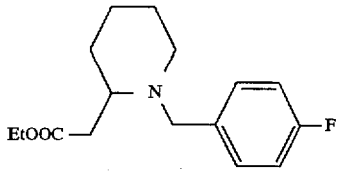

To a solution of ethyl 7-(p-toluenesulfonyloxy)-2-heptenoate (3.0 g, 9.2 mmol) in ethanol (30 ml) were added in turn triethylamine (1.3 ml, 9.2 mmol) and p-fluorobenzylamine (1.2 ml, 10 mmol) and the mixture was heated under reflux for 12 hours. After purified water (30 ml) was added to the reaction mixture, the ethanol was distilled off under reduced pressure. The aqueous layer was extracted with chloroform (100 ml×3) and the combined organic layer was washed successively with saturated aqueous sodium hydrogen carbonate (50 ml) and saturated aqueous sodium chloride (50 ml), dried over potassium carbonate and the solvent was distilled off under reduced pressure. The residue was chromatographed using silica gel column and the fraction from ethyl acetate-hexane (1/3) gave the title compound (2.98 g). Yield=100%.

$^1$HNMR(CDCl$_3$)δ1.24(t,J=7 Hz,2H), 1.32–1.56(m,4H), 1.57–1.68(m,1H), 1.68–1.80(m,1H), 2.09–2.20(m,1H), 2.43 (dd,J=8 Hz,15 Hz,1H), 2.52–2.62(m,1H), 2.67(dd,J=5 Hz,15 Hz, 1H), 2.80–3.01(m,1H), 3.32(d,J=14 Hz,1H), 3.75 (d,J=14 Hz,1H), 4.13(q,J=7 Hz,2H), 6.98(t,J=9 Hz,2H), 7.26 (d,J=5 Hz,1H), 7.28(d,J=6 Hz,1H)

IR(film) 1740, 1516, 1224cm$^{-1}$ d) N-Methyl-2-[1-(p-fluorobenzyl)-2-piperidyl]acetamide

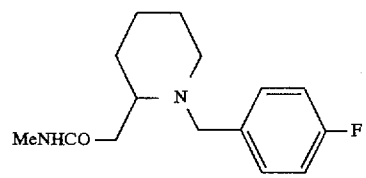

To a suspension of methylamine hydrochloride (508 mg, 7.53 mmol) in toluene (20 ml) was added trimethylaluminum (2M/solution in toluene, 3.8 ml, 7.53 mmol) under ice-cooling and the mixture was stirred for 30 minutes and then at room temperature for further 35 minutes. The reaction mixture was again ice-cooled, a solution of ethyl 2-[1-(p-fluorobenzyl)-2-piperidyl]acetate (1.75 g, 6.27 mmol) in toluene (20 ml) was added dropwise over 10 minutes and the mixture was allowed to rise to room temperature and stirred for 21 hours. To the reaction mixture was added carefully aqueous ammonia (40 ml) under ice-cooling, the mixture was filtered with Celite and the filtrate was extracted with ethyl acetate (100 ml×3). The combined organic layer was washed with saturated aqueous sodium chloride (50 ml), dried over potassium carbonate and the solvent was distilled off under reduced pressure. The residue was chromatographed using silica gel column and the fraction from methanol-chloroform (1/20) gave 1.13 g of the title compound as a colorless oily substance. Yield=68%.

$^1$HNMR(CDCl$_3$)δ1.23–1.46(m,1H), 1.47–1.62(brm,2H), 1.62–1.82(m,2H), 1.93–2.09(m,1H), 2.44(dd,J=4 Hz,17 Hz,1H), 2.55–2.93(m,4H), 2.82(d,J=5 Hz,3H), 3.20(d,J=13 Hz,1H), 4.03(d,J=13 Hz,1H), 7.02(t,J=9 Hz,2H), 7.18(d,J=5 Hz,1H), 7.20(d,J=5 Hz,1H)

IR(film) 3300, 1650, 1510, 1220cm$^{-1}$ e) 2-(2-Methylaminoethyl)-1-(p-fluorobenzyl)piperidine To a suspension of lithium aluminum hydride (243 mg, 6.40 mmol) in THF (10 ml) was added dropwise under ice-cooling a solution of N-methyl-2-[1-(p-fluorobenzyl)-2-piperidyl]acetamide (1.13 g, 4.26 mmol) in THF (20 ml). The mixture was stirred for 20 minutes and then heated under reflux for 1.5 hours. To the reaction mixture was added dropwise under ice-cooling aqueous ammonia (20 ml) and the mixture was stirred at room temperature for 3 hours. Then, it was filtered with Celite and the aqueous layer was extracted with chloroform (50 ml×3). The combined organic layer was washed with saturated aqueous sodium chloride (20 ml), dried over potassium carbonate and the solvent was distilled off under reduced pressure to give crude 2-(2-methylaminoethyl)-1-(p-fluorobenzyl)piperidine (860 mg). Yield=76%. This compound was used for the subsequent reaction without purification.

PREPARATION EXAMPLE 16

4-Amino-1-(p-fluorobenzyl)piperidine

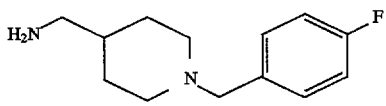

a) 1-(p-Fluorobenzyl)-4-hydroxypiperidine

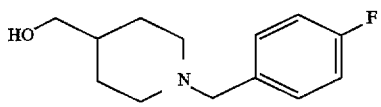

To a solution of 4-hydroxypiperidine (10.0 g, 98.7 mmol) in chloroform (100 ml) were added triethylamine (15 ml, 98.7 mmol) and p-fluorobenzyl chloride (12 ml, 98.7 mmol) and the mixture was stirred at room temperature for 12 hours. The reaction mixture was washed successively with 20% aqueous sodium hydroxide (100 ml×2), and saturated aqueous sodium chloride (100 ml), dried over anhydrous magnesium sulfate. The solvent was distilled off under reduced pressure to give 17.1 g of the title compound as a pale yellow oily substance. Yield=83%.

$^1$HNMR(CDCl$_3$)δ1.53–1.63(m,1H), 1.85–1.92(m,1H), 2.10–2.16(m,1H), 2.70–2.75(m,1H), 3.46(s,2H), 3.70(m, 1H), 6.99(t,J=9 Hz,2H), 7.27(dd,J=6 Hz,9 Hz,2H)

b) 1-(p-Fluorobenzyl)-4-phthalimidopiperidine

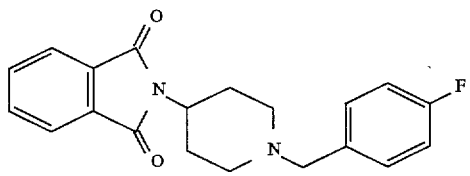

To a suspension of 1-(p-fluorobenzyl)-4-hydroxypiperidine (9.6 g, 46.0 mmol), phthalimide (8.1 g, 55.2 mmol) and triphenylphosphine (14.5 g, 55.2 mmol) in THF (45 ml) was added under ice-cooling a solution of diethyl azodicarboxylate (9.6 g, 55.2 mmol) in THF (20 ml) and the mixture was stirred at room temperature overnight. The solvent was distilled off under reduced pressure, and the resulting yellow oily substance was chromatographed using silica gel column and the fraction from acetone-hexane gave 3.4 g of the title compound. Yield=22%.

$^1$HNMR(CDCl$_3$)δ1.22(bs,2H), 2.09(ddd,J=2 Hz,12 Hz,12 Hz,2H), 2.56(ddd,J=2 Hz,12 Hz,12 Hz,2H), 2.98(bs,2H), 3.51(s,2H), 4.13(tt,J=4 Hz,12 Hz,1H), 7.01(t,J=9 Hz,2H), 7.30(dd,J=6 Hz, 9 Hz,2H), 7.75(dd,J=3 Hz,5 Hz,2H), 7.87 (dd,J=3 Hz,5 Hz,2H)

c) 4-Amino-1-(p-fluorobenzyl)piperidine

To a solution of 1-(p-fluorobenzyl)-4-phthalimidopiperidine (3.0 g, 8.9 mmol) in ethanol (30 ml) was added hydrazine monohydrate (0.7 ml) and the mixture was heated under reflux for 3 hours. After allowed to cool, to the reaction mixture was added 5N hydrochloric acid (50 ml) and insolubles were filtered off. Then, the filtrate was washed with chloroform (30 ml×3). The aqueous layer was neutralized with potassium carbonate and then extracted with chloroform (50 ml×4). After drying over anhydrous magnesium sulfate, the solvent was distilled off to give 1.7 g of the title compound. Yield=94%.

$^1$HNMR(CDCl$_3$)δ1.38(ddd,J=3 Hz,12 Hz,12 Hz,2H), 1.79(bs,2H), 2.01(ddd,J=3 Hz,12 Hz,12 Hz,2H), 2.66(tt,J=4 Hz,10 Hz,1H), 2.80(bs,2H), 3.45(S,2H), 6.99(t,J=8 Hz,2H), 7.26(dd,J=6 Hz,8 Hz,2H)

PREPARATION EXAMPLE 17

1-(p-Fluorobenzyl)-4-(2-aminoethyl)piperazine

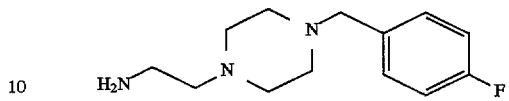

This compound was synthesized from 1-(2-hydroxyethyl)piperazine according to the same process as in Preparation Example 16.

a) 1-(p-Fluorobenzyl)-4-(2-hydroxyethyl)piperazine Yield=86%.

$^1$HNMR(CDCl$_3$)δ2.47(brm,8H), 2.54(t,J=5 Hz,2H), 3.47 (s,2H), 3.60(t,J=5 Hz,2H), 7.00(t,J=9 Hz,2H), 7.28(dd,J=5 Hz,9 Hz,2H)

b) 1-(p-Fluorobenzyl)-4-(2-phthalimidoethyl)piperazine Yield=64%.

$^1$HNMR(CDCl$_3$)δ2.40–2.55(brm,4H), 2.63(t,J=7 Hz,2H), 3.43(s,2H), 3.81(t,J=7 Hz,2H), 7.00(t,J=9 Hz,2H), 7.25(dd, J=5 Hz,9 Hz,2H), 7.71(dd,J=3 Hz,5 Hz,2H), 7.84(dd,J=3 Hz,5 Hz,2H)

c) 1-(p-Fluorobenzyl)-4-(2-aminoethyl)piperazine Yield=92%.

$^1$HNMR(CDCl$_3$)δ2.42(t,J=6 Hz,2H), 2.47(bs,8H), 2.78(t, J=6 Hz,2H), 3.47(s,2H), 6.99(t,J=9 Hz,2H), 7.27(dd,J=6 Hz,9 Hz,2H)

PREPARATION EXAMPLE 18

3-Amino-1-(p-fluorobenzyl)azetidine

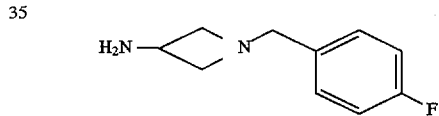

a) 3-Chloro-1-(p-fluorobenzylamino)-2-propanol

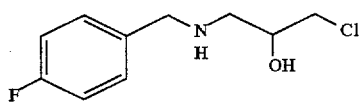

To a solution of p-fluorobenzylamine (50.6 g, 0.405 mol) in ligroin (400 ml) was added epichlorohydrin (31.7 ml, 0.405 mol) and the mixture was stirred at room temperature for 4 days. The so separated substance was recovered by filtration, washed with ligroin and dried at room temperature under reduced pressure for 5 hours to give 61.5 g of the title compound. Yield=70%.

$^1$HNMR(CDCl$_3$)δ2.72(dd,J=7 Hz,12 Hz,1H), 2.83(dd, J=4 Hz,12 Hz, 1H), 3.57(s,1H), 3.58(s,1H), 3.77(bs,1H), 3.80(bs,1H), 3.85–3.92(m,1H), 7.02(t,J=9 Hz,2H), 7.28(dd, J=5 Hz,9 Hz,2H)

b) 1-(p-Fluorobenzyl)-3-trimethylsilyloxyazetidine

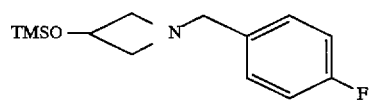

To a solution of 3-chloro-1-(p-fluorobenzylamino)-2-propanol (50.0 g, 0.230 mol) in acetonitrile (200 ml) were added triethylamine (96 ml, 0.69 mol) and N-trimethylsilylacetamide (30.2 g, 0.230 mol) and the mixture was heated under reflux for 20 hours. After the so separated substance was filtered off, the filtrate was distilled off under reduced pressure. After ligroin (500 ml) was added thereto, insolubles were further filtered off. The filtrate was distilled off under reduced pressure to give a yellow oily substance, which was then distilled under reduced pressure (125°–130° C./4–5 mmHg) to give 51.4 g of the title compound as a main fraction as a colorless oily substance. Purity=65%. Reduced yield=33%. This compound was used for the subsequent reaction without purification.

$^1$HNMR(CDCl$_3$)δ0.09(s,9H), 2.86(ddd,J=2 Hz,6 Hz,6 Hz,2H), 3.57(s,2H), 3.60(ddd,J=2 Hz,6 Hz,6 Hz,2H), 4.41(quint,J=6 Hz, 1H), 6.99(t,J=9 Hz,2H), 7.22(dd,J=6 Hz,9 Hz,2H)

c) 1-(p-Fluorobenzyl)-3-hydroxyazetidine

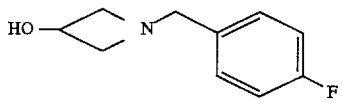

To 1-(p-fluorobenzyl)-3-trimethylsilyloxyazetidine (35.8 g, 0.112 mol) was added a 2.8% sodium methylate solution in methanol (350 ml). After 5 minutes, the solvent was distilled off under reduced pressure and the resulting residue was mixed with water (200 ml) and extracted with chloroform (250 ml×4). The chloroform layer was dried over anhydrous magnesium sulfate and the solvent was distilled off under reduced pressure to give the title compound substantially quantitatively. This compound was used for the subsquent reaction without purification.

$^1$HNMR(CDCl$_3$)δ2.94(ddd,J=2 Hz,6 Hz,6 Hz,2H), 3.58(s,2H), 3.60(ddd,J=2 Hz,6 Hz,6 Hz,2H), 4.43(quint,J=6 Hz,1H), 6.99(t,J=9 Hz,2H),7.22(dd,J=6 Hz,9 Hz,2H)

d) 3-Amino-1-(p-fluorobenzyl)azetidine

This compound was synthesized from 1-(p-fluorobenzyl)-3-hydroxyazetidine according to the same process as in Preparation Examples 16b–16c. 1-(p-Fluorobenzyl)-3-phthalimidoazetidine Yield=47%.

$^1$HNMR(CD$_3$OD)δ3.69(ddd,J=2 Hz,9 Hz,9 Hz,2H), 3.79(s,2H), 3.85(ddd,J=2 Hz,9 Hz,9 Hz,2H), 7.76–7.84(m,4H) 3-Amino-1-(p-fluorobenzyl)azetidine Yield=78%.

$^1$HNMR(CDCl$_3$)δ1.90(m,2H), 2.75(s,2H), 2.83(bs,2H), 6.19(t,J=9 Hz,2H), 6.43(dd,J=6 Hz,9 Hz,2H)

PREPARATION EXAMPLE 19

1-(p-Fluorobenzyl)piperazine

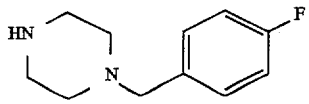

To a solution of piperazine (86 g, 1.00 mol) in ethanol (500 ml) was added under ice-cooling a solution of p-fluorobenzyl chloride (12 ml, 0.77 mol) in ethanol (200 ml) and the mixture was stirred at room temperature for 12 hours. After the so separated substance was filtered off, the filtrate was distilled off under reduced pressure. The residue was mixed with 45% sodium hydroxide (200 ml) and extracted with diethyl ether (400 ml×3). The ether layer was dried over potassium hydroxide and distilled off under reduced pressure. The oily substance thus obtained was distilled under reduced pressure to give 56.1 g of the title compound as colorless crystals. Yield=29%. b.p. 293° C.

$^1$HNMR(CDCl$_3$)δ2.39(bs,4H), 2.88(t,J=5 Hz,4H), 3.45(s,2H), 6.99(t,J=8 Hz,2H), 7.28(dd,J=5 Hz,8 Hz,2H)

PREPARATION EXAMPLE 20

3-(p-Fluorobenzylamino)-6-phenyl-5-oxahexylamine

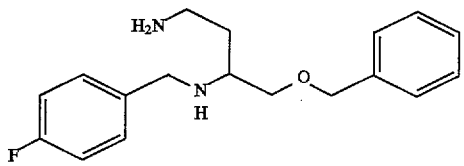

a) O-Benzylglycidol

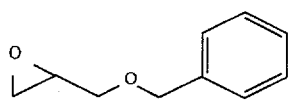

To a solution of epichlorohydrin (50 g, 0.54 mol) in benzyl alcohol (140 ml) was added under ice-cooling boron trifluoride etherate (2.0 ml, 16 mmol) and the mixture was stirred at 60° C. for 3 hours. To the reaction mixture were added at room temperature diethyl ether (400 ml) and a solution of sodium hydroxide (32.4 g, 0.811 mol) in purified water (800 ml) and the mixture was stirred for 15 hours. The reaction mixture was extracted with diethyl ether (200 ml×3), the combined organic layer was washed with saturated aqueous sodium chloride (300 ml×2), dried over anhydrous magnesium sulfate and the solvent was distilled off under reduced pressure. The residue was distilled under reduced pressure to give 68.06 g of the title compound. Yield=85%. b.p.$_{0.5}$ 100°–140° C $^1$HNMR(CDCl$_3$)δ2.62(dd,J=3 Hz,5 Hz,1H), 2.81(t,J=4 Hz,1H), 3.13–3.22(m,1H), 3.44(dd,J=6 Hz,11 Hz,1H), 3.77(dd,J=3 Hz,11 Hz, 1H), 4.56(d,J=12 Hz,1H), 4.65(d,J=12 Hz,1H), 7.26–7.40(m,5H)

b) 3-Hydroxy-6-phenyl-5-oxahexanenitrile

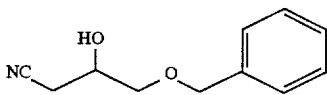

To a solution of O-benzylglycidol (1.0 g, 6.8 mmol) in dimethylformamide-purified water (5/1, 12 ml) was added potassium cyanide (880 mg, 13.5 mmol) and the mixture was stirred at room temperature for 15 hours. To the reaction mixture was added 10% aqueous sodium hydroxide (30 ml) and extracted with diethyl ether (100 ml×3). The combined organic layer was washed successively with purified water (100 ml) and saturated aqueous sodium chloride (100 ml) and dried over sodium sulfate. The solvent was distilled off under reduced pressure to give crude 3-hydroxy-6-phenyl-5-oxahexanenitrile (680 mg). Yield=52%. This compound was used for the subsequent reaction without purification.

c) 6-Phenyl-5-oxa-2-hexenenitrile

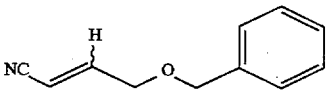

To a solution of 3-hydroxy-6-phenyl-5-oxahexanenitrile (3.51 g, 18.4 mmol) in dichloromethane (40 ml) were added in turn triethylamine (2.8 ml, 20 mmol), dimethylaminopyridine (224 mg, 1.84 mmol) and methanesulfonyl chloride (2.1 ml, 28 mmol) and the mixture was stirred at room temperature for 30 minutes. Thereafter, 1,8-diazabicyclo[5.4.0]-7-undecene (4.1 ml, 28 mmol) was added to the reaction mixture and heated under reflux for one hour. To the reaction mixture was added methylene chloride (100 ml) and washed successively with saturated aqueous ammonium chloride (50 ml), saturated aqueous sodium hydrogen carbonate (50 ml) and saturated aqueous sodium chloride (50 ml), dried over anhydrous magnesium sulfate and the solvent was distilled off under reduced pressure. The residue was chromatographed using silica gel column to give the title compound (2.94 g) from the fraction with ethyl acetate-hexane (1/4). Yield=92%. Mixture of E/Z=1/1

$^1$HNMR(CDCl$_3$)δ4.14, 4.35(dd,J=2 Hz,4 Hz and dd,J=2 Hz,6 Hz, 1H), 4.56, 4.57(s×2,1H), 5.72, 5.45(dt×2,2 Hz,16 Hz and J=2 Hz,12 Hz,1H), 6.61, 6.74(dt×2,J=6 Hz,12 Hz and J=4 Hz,16 Hz,1H), 7.25–7.39(m,5H)

d) 3-(p-Fluorobenzylamino)-6-phenyl-5-oxahexanenitrile

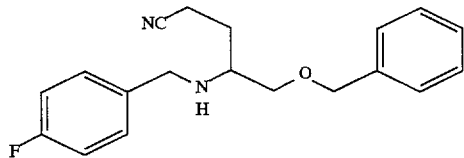

To a solution of 6-phenyl-5-oxa-2-hexenenitrile (240 mg, 1.39 mmol) in ethanol (5 ml) was added p-fluorobenzylamine (0.23 ml, 2.8 mmol) and the mixture was heated under reflux for 4 hours. The solvent was distilled off under reduced pressure and the residue was chromatographed using silica gel column to give 340 mg of the title compound from the fraction from ethyl acetate-hexane (1/9). Yield=82%.

$^1$HNMR(CDCl$_3$)δ2.56(d,J=6 Hz,2H), 3.03–3.12(m,1H), 3.54(d,J=5 Hz,2H), 3.77(d,J=4 Hz,2H), 4.52(d,J=2 Hz,2H), 6.97–7.03(m,2H), 7.25–7.38(m,7H)

e) 3-(p-Fluorobenzylamino)-6-phenyl-5-oxahexylamine

To a suspension of lithium aluminum hydride (136 mg, 3.58 mmol) in diethyl ether (10 ml) was added under ice-cooling conc. sulfuric acid (0.15 ml, 1.5 mmol) and, after stirring for 0.5 hour, a solution of 3-(p-fluorobenzylamino)-6-phenyl-5-oxahexanenitrile (300 mg, 1.01 mmol) in diethyl ether (5 ml) was added dropwise and the mixture was heated under reflux for one hour. After cooling, aqueous ammonia (2 ml) was added under ice-cooling to the reaction mixture and stirred for 2 hours. The reaction mixture was filtered with Celite and the filtrate was distilled off under reduced pressure. The residue was chromatographed using silica gel column to give the title compound as a colorless oily substance from the fraction from methanol-chloroform-aqueous ammonia (90/10/0.5). Yield=82%.

$^1$HNMR(CDCl$_3$)δ1.62(dd,J=7 Hz,13 Hz,2H), 2.72–2.87 (m,3H), 3.41 (dd,J=6 Hz,9 Hz,1H), 3.52(dd,J=4 Hz,10 Hz,1H), 4.51(s,2H), 6.95–7.01(m,2H), 7.25–7.37(m,5H)

PREPARATION EXAMPLE 21

2-(p-Fluorobenzyl)-3aβ,5α,6aβ-octahydrocyclopenta[c]pyrrol-5-amine

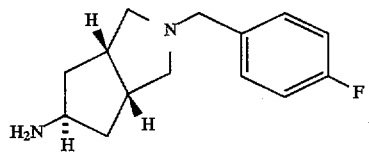

a) N-Allyl-p-fluorobenzamide

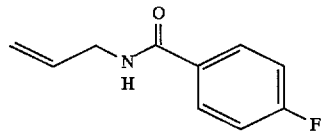

To a solution of allylamine (10 g, 0.18 mol) in methylene chloride (150 ml) were added in turn triethylamine (26.9 ml, 0.193 mol) and dimethylaminopyridine (2.14 g, 17.5 mmol) and then p-fluorobenzoyl chloride (21.7 ml, 0.184 mol) under ice-cooling. After stirring for 30 minutes, the mixture was allowed to rise to room temperature and stirred for 17.5 hours. To the reaction mixture was added saturated aqueous sodium hydrogencarbonate (100 ml) and extracted with methylene chloride (50 ml×3). The combined organic layer was washed with saturated aqueous sodium chloride (100 ml), dried over anhydrous magnesium sulfate and the solvent was distilled off under reduced pressure. The residue was chromatographed using silica gel column to give 30.74 g of the title compound from the fraction from ethyl acetate-hexane (1/3). Yield=98%.

$^1$HNMR(CDCl$_3$)δ4.01–4.14(m,2H), 5.20(dd,J=1 Hz,10 Hz,1H), 5.27 (dd,J=1 Hz,17 Hz,1H), 5.84–5.99(m,1H), 6.09–6.32(br,1H), 7.11(t,J=8 Hz,2H), 7.79(d,J=5 Hz,1H), 7.81(d,J=5 Hz,1H)

b) N-Allyl-N-(1-propynyl)-p-fluorobenzamide

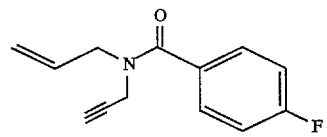

To a solution of sodium hydride (581 mg, 14.5 mmol) in dimethylformamide (15 ml) was added under ice-cooling a solution of N-allyl-p-fluorobenzamide (2.0 g, 11 mmol) in dimethylformamide (15 ml) and the mixture was stirred for 10 minutes, allowed to rise to room temperature and then stirred for 15 minutes. To the reaction mixture was added under ice-cooling propargyl bromide (1.29 ml, 14.5 mmol) and the mixture was stirred for 15 minutes, allowed to rise to room temperature and then stirred for further 30 minutes. To the reaction mixture was added saturated aqueous sodium hydrogencarbonate (30 ml) and extracted with ethyl acetate (80 ml×3). The combined organic layer was washed successively with purified water (50 ml) and saturated aqueous sodium chloride (50 ml), dried over anhydrous magnesium sulfate and the solvent was distilled off under reduced pressure. The residue was chromatographed using silica gel column to give 2.32 g of the title compound from the fraction from ethyl acetate-hexane (1/4). Yield=96%.

$^1$HNMR(CDCl$_3$)δ2.18–2.44(br,1H), 3.78–4.51(brm,4H), 5.18–5.40 (m,2H), 5.68–5.96(br,1H), 6.99–7.21(m,2H), 7.38–7.70(m,2H)

c) 2-(p-Fluorobenzoyl)-2,3,3a,4-tetrahydrocyclopenta[c]-pyrrol-5(1H)-one

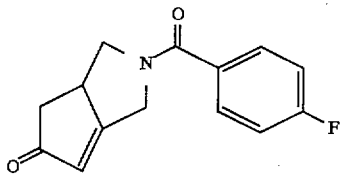

To a solution of N-allyl-N-(2-propynyl)-p-fluorobenzamide (2.32 g, 10.7 mmol) in methylene chloride (50 ml) was added dicobalt octacarbonyl (4.02 g, 11.8 mmol) at room temperature and the mixture was stirred for one hour. Then, to the reaction mixture was added portionwise N-methylmorpholine-N-oxide (7.51 g, 64.2 mmol) over 10 minutes and the mixture was stirred for 20 minutes. The reaction mixture was filtered with silica gel and the filtrate was distilled under reduced pressure. The residue was chromatographed using silica gel column to give 1.54 g of the title compound from the fraction from ethyl acetate-hexane (4/1). Yield=59%.

$^1$HNMR(CDCl$_3$)δ2.08–2.32(m,1H), 2.53–2.80(m,1H), 2.99–3.4 (m,2H), 3.92–4.09(m,1H), 4.26–4.58(m,2H), 4.69–4.85(m,1H), 6.05,6.20(s×2,1H), 7.13(t,J=9 Hz,2H), 7.47–7.62(m,2H)

d) 2-(p-Fluorobenzoyl)-3aβ,5α,6aβ-octahydrocyclopenta[c]pyrrol-5-ol

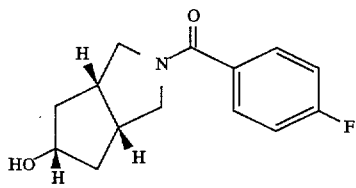

To a solution of 2-(p-fluorobenzoyl)-2,3,3a,4-tetrahydrocyclopenta[c]pyrrol-5(1H)-one (1.54 g, 6.29 mmol) in methanol-chloroform (3/2, 15 ml) was added 10% palladium-carbon (154 mg) and the mixture was stirred at room temperature under hydrogen stream for 26 hours. The reaction mixture was filtered with Celite and the filtrate was distilled under reduced pressure to give crude 2-(p-fluorobenzoyl)-3aβ,6aβ-hexahydrocyclopenta[c]pyrrol-5(1H)-one (1.78 g). This compound was used for the subsequent reaction without purification.

To a solution of the crude 2-(p-fluorobenzoyl)-3aβ,6aβ-hexahydrocyclopenta[c]pyrrol-5(1H)-one (1.78 g) in ethanol (15 ml) was added portionwise sodium borohydride (327 mg, 8.65 mmol) under ice-cooling over 10 minutes and the mixture was stirred for 20 minutes. To the reaction mixture was added acetone (5 ml) and the solvent was distilled off under reduced pressure. The residue was dissolved in chloroform (100 ml), washed successively with saturated aqueous sodium hydrogen carbonate (30 ml) and saturated aqueous sodium chloride (30 ml), dried over anhydrous magnesium sulfate and the solvent was distilled off under reduced pressure. The residue was chromatographed using silica gel column to give 1.65 g of the title compound from the fraction from methanol-chloroform (1/20). A total yield of two steps=100%.

$^1$HNMR(CDCl$_3$)δ1.40–1.78(brm,3H), 2.00–2.28(brm,2H), 2.59–2.79(brm,2H), 3.32–3.93(brm,4H), 4.25–4.41(m,1H), 7.07(t,J=9 Hz,2H), 7.50(d,J=5 Hz,2H), 7.52(d,J=5 Hz,1H)

e) 2-(p-Fluorobenzyl)-3aβ,5α,6aβ-octahydrocyclopenta[c]pyrrol-5-amine

To a solution of lithium aluminum hydride (229 mg, 6.02 mmol) in THF (10 ml) was added dropwise under ice-cooling a solution of 2-(p-fluorobenzoyl)-3aβ,5α,6aβ-octahydrocyclopenta[c]pyrrol-5-ol (1.0 g, 4.02 mmol) in THF (10 ml) and the mixture was stirred for 10 minutes and then heated under reflux for a further 6.5 hours. To the reaction mixture was added aqueous ammonia (10 ml) under ice-cooling and the mixture was stirred for one hour. It was filtered with Celite and the filtrate was extracted with ethyl acetate (30 ml×3). The combined organic layer was dried over potassium carbonate and distilled off under reduced pressure to give crude 2-(p-fluorobenzyl)-3aβ,5β,6aβ-octahydrocyclopenta[c]pyrrol-5-ol (850 mg).

To a solution of 2-(p-fluorobenzyl)-3aβ,5β,6aβ-octahydrocyclopenta[c]pyrrol-5-ol (850 mg, 3.62 mmol) in THF (10 ml) were added in turn triphenylphosphine (1.14 g, 4.34 mmol), phthalimide (639 mg, 4.34 mmol) and diethyl azodicarboxylate (0.68 ml, 4.34 mmol) and the mixture was stirred for one hour and then at room temperature for further 15 hours. The reaction mixture was distilled off under reduced pressure. The residue was dissolved in ethanol (15 ml) and hydrazine monohydrate (0.41 ml, 13.19 mmol) was added and the mixture was heated under reflux for 35 minutes. After cooling, purified water (50 ml) was added to dissolve insolubles and then the ethanol was distilled off under reduced pressure. The aqueous layer was made strongly basic by the addition of potassium carbonate and extracted with chloroform (50 ml×3). The combined organic layer was extracted with 10% aqueous hydrochloric acid (50 ml×3). The combined aqueous hydrochloric acid layer was washed with chloroform (100 ml) and the aqueous layer was made strongly basic by the addition of 10% aqueous sodium hydroxide and extracted with chloroform (80 ml×3). The combined organic layer was dried over potassium carbonate and distilled off under reduced pressure to give crude 2-(p-fluorobenzyl)-3aβ,5α,6aβ-octahydrocyclopenta[c]pyrrol-5-amine (950 mg). Yield of two steps=100%. This compound was used for the subsequent reaction without purification.

PREPARATION EXAMPLE 22

2-Aminomethyl-6-[N-ethoxycarbonyl-N-(p-fluorobenzyl)aminomethyl]tetrahydropyrane

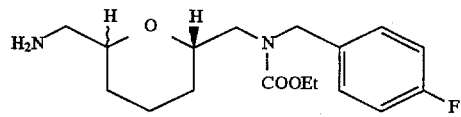

a) 3-Chloro-1-(p-fluorobenzylamino)-2-propanol

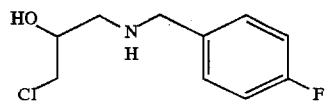

Epichlorohydrin (13 ml, 0.17 mol) was added a solution of p-fluorobenzylamine (20.8 g, 0.166 mol) in ligroin (200 ml) at room temperature and the mixture was stirred for 94 hours. The product separated out in the reaction mixture was recovered by filtration to give the title compound (20.78 g). Yield=63%.

$^1$HNMR(CDCl$_3$)δ2.14–2.57(br,2H), 2.71(dd,J=7 Hz,13 Hz,1H), 2.83(dd,J=4 Hz,13 Hz,1H), 3.57(d,J=5 Hz,2H), 3.76(d,J=13 Hz,1H), 3.81(d,J=14 Hz,1H), 3.80–3.99(m,1H), 7.02(t,J=8 Hz,2H), 7.27(d,J=5 Hz,1H), 7.29(d,J=6 Hz,1H)

b) Ethyl N-(p-fluorobenzyl)-N-oxiranylmethylcarbamate

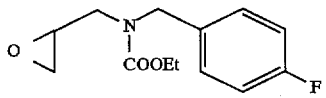

To a solution of 3-chloro-1-(p-fluorobenzylamino)-2-propanol (20.78 g, 66.50 mmol) in methylene chloride (150 ml) were added in turn triethylamine (10.2 ml, 73.2 mmol), dimethylaminopyridine (812 mg, 6.65 mmol), ethyl chlorocarbonate (5.7 ml, 73 mmol) under ice-cooling and the mixture was stirred for one hour, allowed to rise to room temperature and then stirred for further 19 hours. The reaction mixture was diluted with chloroform (100 ml), washed successively with 10% aqueous hydrochloric acid (50 ml), saturated aqueous sodium hydrogen carbonate (50 ml) and saturated aqueous sodium chloride (50 ml), dried over anhydrous magnesium sulfate. The solvent was distilled off under reduced pressure to give crude ethyl N-(p-fluorobenzyl)-N-(3-chloro-2-hydroxypropyl)carbamate (24.28 g). This compound was used for the subsequent reaction without purification.

To a solution of the crude ethyl N-(p-fluorobenzyl)-N-(3-chloro-2-hydroxypropyl)carbamate (24 g) in THF (200 ml) was added 10% aqueous sodium hydroxide (51.8 ml, 0.130 mol) under ice-cooling and the mixture was stirred for 15 minutes and then at room temperature for further 2.5 hours. The reaction mixture was extracted with diethyl ether (100 ml×3). The combined organic layer was washed successively with purified water (100 ml), and saturated aqueous sodium chloride (100 ml), dried over anhydrous magnesium sulfate and the solvent was distilled off under reduced pressure. The residue was chromatographed using silica gel column to give 14.82 g of the title compound from the fraction from ethyl acetate-hexane (1/3). Yield=67%.

¹HNMR(CDCl₃)δ1.19–1.25(brm,3H), 2.34–2.54(brm, 1H), 2.63–2.80(brm,1H), 2.92–3.19(brm,2H), 3.41–3.61, 3.68–3.85 (pair of brm,1H), 4.21(q,J=7 Hz,2H), 4.46(d,J=15 Hz,1H), 4.52–4.71(brm,1H), 7.01(t,J=8 Hz,2H), 7.09–7.35 (brm,2H)

c) Ethyl N-(p-fluorobenzyl)-N-(2-hydroxy-6-heptenyl)carbamate

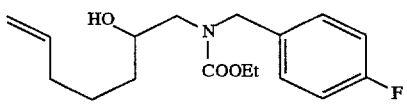

To a suspension of magnesium ribbons (1.69 g, 69.3 mmol) in anhydrous THF (150 ml) was added dropwise 4-bromo-1-butene (6.9 ml, 68 mmol) over 20 minutes so as to maintain a gentle refluxing. The reaction mixture was cooled to −24° C., copper iodide (6.47 g, 34.0 mmol) was added and the mixture was stirred for 10 minutes. Then, a solution of ethyl N-(p-fluorobenzyl)-N-oxiranylmethylcarbamate (4.73 g, 13.6 mmol) in anhydrous THF (20 ml) was added dropwise over 5 minutes and stirred for 30 minutes. To the reaction mixture was added a saturated aqueous solution of ammonium chloride (100 ml) and filtered with Celite. The filtrate was extracted with ethyl acetate (100 ml×3). The combined organic layer was washed with saturated aqueous sodium chloride (100 ml), dried over anhydrous magnesium sulfate and the solvent was distilled off under reduced pressure. The residue was chromatographed using silica gel column to give 5.2 g of the title compound from the fraction from ethyl acetate-hexane (1/2). Yield=100%.

¹HNMR(CDCl₃)δ1.27(t,J=7 Hz,3H), 1.33–1.42(brm,2H), 1.42–1.60(m,1H), 1.83–2.12(brm,3H), 2.98–3.57(brm,3H), 3.68–3.84(brm,1H), 4.20(q,J=1 Hz,2H), 4.40–4.63(brm, 2H), 4.88–5.05(m,2H), 6.60–8.40(m,1H), 7.02(t,J=9 Hz,2H), 7.09–7.34(brm,2H)

d) 6-[N-Ethoxycarbonyl-N-(p-fluorobenzyl)aminomethyl]-2-iodomethyltetrahydropyrane

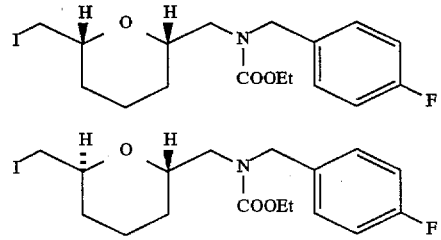

To a solution of ethyl N-(p-fluorobenzyl)-N-(2-hydroxy-6-heptenyl)carbamate (1.0 g, 2.5 mmol) in methylene chloride (15 ml) was added iodine (1.26 g, 4.95 mmol) and the mixture was stirred at room temperature for 15 hours and then heated under reflux for further 7 hours. The reaction mixture was diluted with methylene chloride (50 ml) and washed successively with saturated aqueous sodium hydrogen carbonate (50 ml), 10% aqueous sodium thiosulfate (50 ml×2), saturated aqueous sodium hydrogen carbonate (50 ml) and saturated aqueous sodium chloride (50 ml), dried over anhydrous sodium sulfate and the solvent was distilled off under reduced pressure. The residue was chromatographed using silica gel column to give cis-6-[N-ethoxycarbonyl-N-(p-fluorobenzyl)aminomethyl]-2-iodomethyltetrahydropyrane (560 mg, yield 51%) and trans-6-[N-ethoxycarbonyl-N-(p-fluorobenzyl)aminomethyl]-2-iodomethyltetrahydropyrane (190 mg, yield 17%) from the fraction from ethyl acetate-benzene (1/30).

cis-6-[N-Ethoxycarbonyl-N-(p-fluorobenzyl)aminomethyl]-2-iodomethyltetrahydropyrane ¹HNMR(CDCl₃)δ1.06–1.30(m,5H), 1.19–1.30(m,2H), 1.68–1.78 (brd,J=13 Hz,1H), 1.80–1.90(brd,J=13 Hz,1H), 2.94–3.72 (brm,6H), 4.16(d,J=7 Hz,1H), 4.20(d,J=7 Hz,1H), 4.58(brd,J=15 Hz,1H), 4.79(brd,J=15 Hz,1H), 6.99(t,J=9 Hz,2H), 7.12–7.32(brm,2H)

trans-6-[N-Ethoxycarbonyl-N-(p-fluorobenzyl) aminomethyl]-2-iodomethyltetrahydropyrane ¹HNMR(CDCl₃)δ1.18–1.38(brm,5H), 1.42–1.84(brm, 4H), 3.18–3.40(brm,4H), 3.79–4.00(brm,2H), 4.17(d,J=7 Hz,1H), 4.21(d,J=7 Hz,1H), 4.52(d,J=16 Hz,1H), 7.00(t,J=9 Hz,2H), 7.12–7.34(brm,2H)

e) cis-2-Aminomethyl-6-[N-ethoxycarbonyl-N-(p-fluorobenzyl)-aminomethyl]tetrahydropyrane

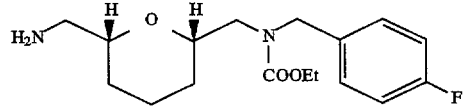

To a solution of cis-6-[N-ethoxycarbonyl-N-(p-fluorobenzyl)aminomethyl]-2-iodomethyltetrahydropyrane (2.71 g, 5.10 mmol) in dimethylformamide (30 ml) was added potassium phthalimide (1.04 g, 5.61 mmol) and the mixture was stirred at 100° C. for 10 hours. To the reaction mixture was added ethyl acetate (200 ml), washed successively with purified water (50 ml) and saturated aqueous sodium chloride (50 ml), dried over anhydrous magnesium sulfate and the solvent was distilled off under reduced pressure to give crude cis-6-[N-ethoxycarbonyl-N-(p- fluorobenzyl)aminomethyl]-2-phthalimidomethyltetrahydropyrane (4.69 g). This compound was used for the subsequent reaction without purification.

To a solution of the crude cis-6-[N-ethoxycarbonyl-N-(p-fluorobenzyl)aminomethyl]-2-phthalimidomethyltetrahydropyrane (2.81 g, 6.19 mmol) in methanol (30 ml) was added hydrazine monohydrate (0.48 ml, 15 mmol) and heated under reflux for 2 hours. To the reaction mixture was added purified water (30 ml) to dissolve insolubles and the ethanol was distilled off under reduced pressure. The aqueous layer was extracted with chloroform (50 ml×3). The combined organic layer was dried over potassium carbonate and the solvent was distilled off under reduced pressure to give crude cis-2-aminomethyl-6-[N-ethoxycarbonyl-N-(p-fluorobenzyl)aminomethyl]tetrahydropyrane (2.0 g). This compound was used for the subsequent reaction without purification. Yield of two steps=100%.

Similarly, the following compounds were prepared.

trans-2-Aminomethyl-6-[N-ethoxycarbonyl-N-(p-fluorobenzyl)-aminomethyl]tetrahydropyrane Yield=100%.

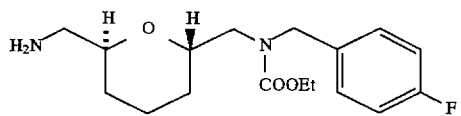

2-Aminomethyl-5-[N-ethoxycarbonyl-N-(p-fluorobenzyl)aminomethyl]tetrahydrofuran

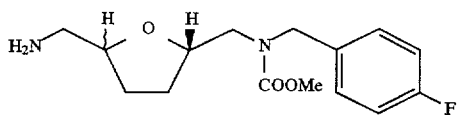

Methyl N-(p-fluorobenzyl)-N-oxiranylmethylcarbamate Yield=40%.

$^1$HNMR(CDCl$_3$)δ2.38–2.50(br,1H), 2.67–2.74(brm,1H), 2.97–3.18(brm,2H), 3.76(s,3H), 4.46(d,J=16 Hz,1H), 4.62 (d,J=15 Hz,1H), 7.00(bs,2H), 7.09–7.34(brm,2H) Methyl N-(p-fluorobenzyl)-N-(2-hydroxy-5-hexenyl)carbamate Yield=73%.

$^1$HNMR(CDCl$_3$)δ1.69–1.15(m,2H), 2.10–2.23(m,2H), 3.1–3.28(m,1H), 3.29–3.55(m,2H), 3.75(s,3H), 4.45–4.62 (brm,2H), 4.88–5.30(m,2H), 5.69–5.84(m,1H), 7.10–7.28 (m,4H)

trans-5-[N-methoxycarbonyl-N-(p-fluorobenzyl)aminomethyl]-2-iodomethyltetrahydrofuran Yield=35%.

$^1$HNMR(CDCl$_3$)δ1.46–1.73(brm,2H), 1.95–2.20(brm, 2H), 3.03–3.57(brm,3H), 3.23(dd,J=5 Hz,10 Hz,1H), 3.73 (s,3H), 3.97–4.10(brm,1H), 4.19–4.38(brm,1H), 4.56(brd,J= 16 Hz,1H), 4.70(brd,J=16 Hz,1H), 7.04–7.38(m,4H)

cis-5-[N-methoxycarbonyl-N-(p-fluorobenzyl)aminomethyl]-2-iodomethyltetrahydrofuran Yield=19%.

$^1$HNMR(CDCl$_3$)δ1.55–1.76(m,2H), 1.87–2.29(m,2H), 3.03–3.28 (m,2H), 3.61–3.51(m,1H), 3.73(s,3H), 3.96 (br.quint,J=6 Hz, H), 4.03–4.23(brm,1H), 4.56(brd,J=16 Hz,1H), 4.76(brd, J=16 Hz,1H), 7.11–7.38(brm,4H)

trans-2-Aminomethyl-5-[N-methoxycarbonyl-N-(p-fluorobenzyl)aminomethyl]tetrahydrofuran

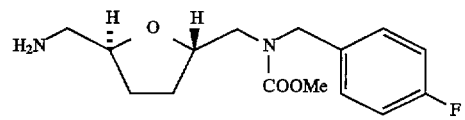

Yield=52%.

cis-2-Aminomethyl-5-[N-methoxycarbonyl-N-(p-fluorobenzyl)-aminomethyl]tetrahydrofuran

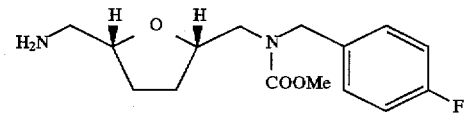

Yield=68%.

PREPARATION EXAMPLE 23 tert-Butyl N-(5-amino-tert-butoxycarbonyl-3-azapentyl)-N-(p-fluorobenzyl)carbamate

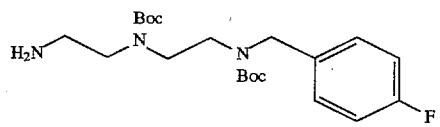

a) 7-(p-fluorophenyl)-3,6-diaza-1-heptanol

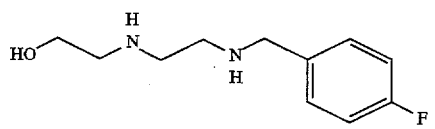

To a solution of p-fluorobenzaldehyde (12.2 g, 97.9 mmol) in methanol (120 ml) was added 2-(2-aminoethylamino)ethanol (10.2 g, 97.9 mmol). Then, sodium borohydride (7.4 g, 0.196 mol) was added under ice-cooling and the mixture was stirred at room temperature for 3 hours. After adding 10% aqueous sodium hydride (300 ml), the mixture was extracted with ethyl acetate (200 ml×2), dried over anhydrous magnesium sulfate and the solvent was distilled off under reduced pressure to give 19.0 g of the title compound as a pale yellow oily substance. Rough yield=91%. This compound was used for the subsequent reaction without purification.

$^1$HNMR(CDCl$_3$)δ2.76(m,6H), 3.64(t,J=5 Hz,2H), 3.77(s, 2H), 7.00(t,J=9 Hz,2H), 7.29(dd,J=5 Hz,9 Hz,2H)

b) tert-Butyl N-(3-tert-butoxycarbonyl-5-hydroxy-3-azapentyl)-N-(p-fluorobenzyl)carbamate

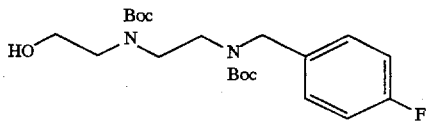

To a solution of 7-(p-fluorophenyl)-3,6-diaza-1-heptanol (12.9 g, 60.6 mmol) in ethyl acetate (120 ml) was added 20% aqueous sodium hydroxide (60 ml). Then, di-tert-butyl dicarbonate (7.0 g, 0.182 mol) was added under ice-cooling and the mixture was stirred at room temperature for one hour. The organic layer was separated and washed with water (50 ml×2), dried over anhydrous magnesium sulfate and the solvent was distilled off under reduced pressure. The residue was chromatographed using silica gel column to give 18.2 g of the title compound from the fraction from acetone-hexane as a colorless oily substance. Yield=50%.

¹HNMR(CDCl₃)δ1.45(s,18H), 3.37(bs,6H), 3.72(bs,2H), 4.42(s,2H), 7.00(t,J=8 Hz,2H), 7.19(bs,2H)

c) N-[7-(p-Fluorophenyl)-3,6-di(tert-butoxycarbonyl)-3,6-diaza-1-heptyl]phthalimide

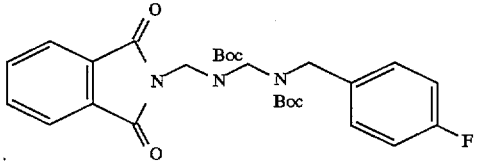

To a suspension of tert-butyl N-(3-tert-butoxycarbonyl-5-hydroxy-3-azapentyl)-N-(p-fluorobenzyl)carbamate (13.0 g, 31.4 mmol), phthalimide (5.1 g, 34.5 mmol) and triphenylphosphine (9.1 g, 34.5 mmol) in THF (50 ml) was added under ice-cooling a solution of diethyl azodicarboxylate (6.0 g, 34.5 mmol) in THF (10 ml) and the mixture was stirred at room temperature overnight. After completion of the reaction, the solvent was distilled off under reduced pressure. The residue was chromatographed using silica gel column to give 15.7 g of the title compound from the fraction from acetone-hexane as a colorless oily substance. Yield=92%.

¹HNMR(CDCl₃/40° C.)δ1.24(bs,9H), 1.46(bs,9H), 3.30 (bs,4H), 3.48(bs,2H), 3.81(bs,2H), 4.38(bs,2H), 6.98(t,J=8 Hz,2H), 7.18(bs,2H), 7.71(bs,2H), 7.83(bs,2H)

d) tert-Butyl N-(5-amino-3-tert-butoxycarbonyl-3-azapentyl)-N-(p-fluorobenzyl)carbamate To a solution of N-[7-(p-fluorophenyl)-3,6-di(tert-butoxycarbonyl)-3,6-diaza-1-heptyl]phthalimide (14.5 g, 26.7 mmol) in methanol (200 ml) was added hydrazine monohydrate (1.4 ml) and heated under reflux for 5 hours. After completion of the reaction, the solvent was distilled off under reduced pressure. To the residue was added chloroform (200 ml) and washed with aqueous ammonia (150 ml×2). The organic layer was dried over anhydrous potassium carbonate and the solvent was distilled off under reduced pressure. The resulting colorless oily substance was chromatographed using silica gel column to give 4.7 g of the title compound from the fraction from methylene chloride-methanol-aqueous ammonia (90/10/0.5) as a colorless oily substance. Yield=43%.

¹HNMR(CD₃OD/40° C.)δ1.46(bs,18H), 2.75(t,J=7 Hz,2H), 3.26(t,J=7 Hz,2H), 3.30–3.35(brm,4H), 4.43(s,2H), 7.05(t,J=9 Hz,2H), 7.25(bs,2H)

PREPARATION EXAMPLE 24 tert-Butyl N-(5-amino-3-oxapentyl)-N-(p-fluorobenzyl)carbamate

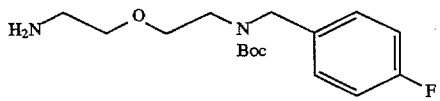

This compound was synthesized from p-fluorobenzaldehyde and 2-(2-aminoethoxy)ethanol according to the same process as in Preparation Example 23.

a) 7-(p-Fluorophenyl)-6-aza-3-oxaheptanol

Rough yield=94%.

¹HNMR(CDCl₃)δ2.82(t,J=5 Hz,2H), 3.59(t,J=4 Hz,2H), 3.64(t,J=5 Hz,2H), 3.72(t,J=4 Hz,2H), 3.78(s,2H), 7.01(t,J=9 Hz,2H), 7.29(dd,J=5 Hz,9 Hz,2H)

b) tert-Butyl N-(p-fluorobenzyl)-N-(5-hydroxy-3-oxapentyl)carbamate

Yield=86%.

¹HNMR(CDCl₃)δ1.43–1.49(brm,9H), 3.33–3.60(brm, 6H), 3.68–3.72(s,2H), 4.46(bs,2H), 7.01(t,J=9 Hz,2H), 7.20 (bs,2H)

c) N-[7-(p-Fluorophenyl)-6-aza-6-(tert-butoxycarbonyl)-3-oxaheptyl]phthalimide

Yield=79%.

¹HNMR(CDCl₃)δ1.38, 1.45(bs×2,9H), 3.21, 3.33(bs×2, 2H), 3.51,3.59(bs×2,2H), 3.65(bs,2H), 4.36, 4.39(bs×2,2H), 6.94(bs,2H), 7.12, 7.18(bs×2,2H), 7.72(dd,J=3 Hz,5 Hz,2H), 7.84(bs,1H)

d) tert-Butyl N-(5-amino-3-oxapentyl)-N-(p-fluorobenzyl)carbamate

Yield=82%.

¹HNMR(CD₃OD/40° C.)δ1.45(bs,9H), 2.75(t,J=3 Hz,2H), 3.36–3.45(m,2H), 3.50–3.58(brm,2H), 4.48(s,2H), 7.04(t,J=9 Hz,2H), 7.23–7.27(m,2H)

PREPARATION EXAMPLE 25 tert-Butyl N-(4-aminobutyl)-N-(tert-butoxycarbonyl)carbamate

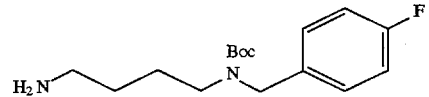

This compound was synthesized from p-fluorobenzaldehyde and 4-amino-1-butanol according to the same process as in Preparation Example 23.

a) 4-(p-Fluorobenzylamine)-1-butanol

Rough yield=94%.

¹HNMR(CDCl₃)δ1.60–1.72(m,4H), 2.69(t,J=5 Hz,2H), 3.60(t,J=5 Hz,2H), 3.75(s,2H), 7.01(t,J=9 Hz,2H), 7.28(dd, J=5 Hz,9 Hz,2H)

b) tert-Butyl N-(4-hydroxybutyl)-N-(p-fluorobenzyl)carbamate

Yield=100%.

¹HNMR(CDCl₃)δ1.45–1.61(brm,13H), 3.21(bs,2H), 3.60–3.65(brm,2H), 7.00(t,J=9 Hz,2H), 7.19(bs,2H)

c) N-[6-(p-Fluorophenyl)-5-(tert-butoxycarbonyl)-5-azahexyl]phthalimide

Yield=50%.

¹HNMR(CDCl₃)δ1.44(s,9H), 1.48–1.53(brm,2H), 1.61–1.66(brm,2H), 3.19(bs,2H), 3.66(t,J=7 Hz,2H), 4.37(s, 2H), 6.95(t,J=9 Hz,2H), 7.18(bs,2H), 7.11(dd,J=3 Hz,5 Hz,2H), 7.83(dd,J=3 Hz,5 Hz,2H)

d) tert-Butyl N-(4-aminobutyl)-N-(tert-butoxycarbonyl)carbamate

Yield=90%.

¹HNMR(CDCl₃)δ1.38–1.48(brm,13H), 2.67(t,J=? Hz,2H), 3.12–3.20(brm,2H), 4.38(bs,2H), 7.00(t,J=9 Hz,2H), 7.19(bs,2H)

PREPARATION EXAMPLE 26 tert-Butyl N-(5-aminopentyl)-N-(p-fluorobenzyl)carbamate

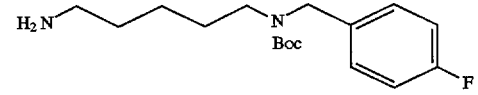

This compound was synthesized from p-fluorobenzaldehyde and 5-amino-1-pentanol according to the same process as in Preparation Example 23.

a) 5-(p-Fluorobenzylamino)pentanol

Rough yield=96%.

¹HNMR(CDCl₃)δ1.39–1.46(brm,2H), 1.50–1.62(brm, 4H), 2.63(t,J=7 Hz,2H), 3.64(t,J=6 Hz,2H), 3.75(s,2H), 7.00 (t,J=9 Hz,2H), 7.28(dd,J=5 Hz,9 Hz,2H)

b) tert-Butyl N-(5-hydroxypentyl)-N-(p-fluorobenzyl)carbamate

Yield=80%.

¹HNMR(CDCl₃)δ1.31–1.36(brm,2H), 1.46(s,9H), 1.46–1.58(brm,4H), 3.17(bs,2H), 3.59–3.64(brm,2H), 4.38 (s,2H), 6.99(t,J=9 Hz,2H), 7.17–7.21(brm,2H)

c) N-[7-(p-Fluorophenyl)-6-(tert-butoxycarbonyl)-6-azaheptyl]phthalimide

Yield=84%.

¹HNMR(CDCl₃/40° C.)δ1.26–1.33(brm,2H), 1.44(s,9H), 1.49–1.54(brm,2H), 1.63–1.69(brm,2H), 3.13(brm,2H), 3.66(t,J=7 Hz,2H), 4.37(s,2H), 6.98(t,J=9 Hz,2H), 7.16–7.20(brm,2H), 7.70(dd,J=3 Hz,5 Hz,2H), 7.83(dd,J=3 Hz, 5 Hz,2H)

d) tert-Butyl N-(5-aminopentyl)-N-(p-fluorobenzyl)carbamate

Yield=96%.

¹HNMR(CD₃OD)δ1.26–1.28(brm,2H), 1.42–1.52(brm, 13H), 2.58(t,J=7 Hz,2H), 3.18(bs,2H), 4.40(s,2H), 7.04(t, J=8 Hz,2H), 7.25(dd,J=6 Hz,8 Hz,2H)

PREPARATION EXAMPLE 27 tert-Butyl N-(2-methoxy-3-aminopropyl)-N-(p-fluorobenzyl)carbamate

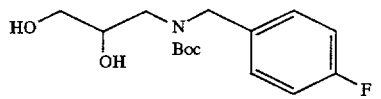

a) tert-Butyl N-(2,3-dihydroxypropyl)-N-(p-fluorobenzyl)carbamate

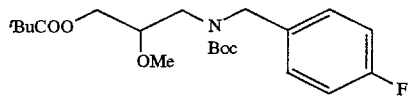

To a solution of p-fluorobenzaldehyde (12.2 g, 98.3 mmol) in methanol (120 ml) was added at room temperature 3-amino-1,2-propanediol (9.0 g, 98.3 mmol). Then, sodium borohydride (7.4 g, 0.197 mol) was added under ice-cooling and the mixture was stirred at room temperature for 3 days. The solvent was distilled off under reduced pressure. To the resulting white foamy substance (45.4 g) was added ethyl acetate (200 ml) and 20% aqueous sodium hydroxide (100 ml) and then di-tert-butyldicarbonate (25.8 g, 0.118 mol) under ice-cooling and the mixture was stirred at room temperature for 3 days. The aqueous layer was separated and extracted with ethyl acetate (100 ml). The combined organic layer was washed with saturated aqueous sodium chloride (100 ml), dried over anhydrous magnesium sulfate and the solvent was distilled off under reduced pressure. The resulting colorless oily substance was chromatographed using silica gel column to give 17.1 g of the title compound from the fraction from acetone-hexane as a colorless oily substance. Yield=58%.

¹HNMR(CDCl₃)δ1.47(s,9H), 4.38–4.49(m,2H), 7.01(2H, t,J=9 Hz), 7.17–7.20(m,2H)

b) tert-Butyl N-(2-hydroxy-3-pivaloyloxypropyl)-N-(p-fluorobenzyl)carbamate

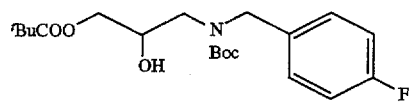

To a solution of tert-butyl N-(2,3-dihydroxypropyl)-N-(p-fluorobenzyl)carbamate (6.3 g, 20.9 mmol) in dichloromethane (20 ml) were added under ice-cooling pyridine (20 ml), pivaloyl chloride (2.5 g, 20.9 mmol) and then N, N-dimethylaminopyridine (0.03 g) and the mixture was stirred at room temperature for 4 days. The solvent was distilled off under reduced pressure and the resulting white emulsified substance was chromatographed using silica gel column to give 6.3 g of the title compound from the fraction from acetone-hexane as a colorless oily substance. Yield= 79%.

¹HNMR(CDCl₃)δ1.19(s,9H), 1.47(s,9H), 3.25–3.30(brm, 2H), 3.98–4.05(brm,2H), 4.48(bs,2H), 7.00(t,J=9 Hz,2H), 7.18–7.21(m,2H)

c) tert-Butyl N-(2-methoxy-3-pivaloyloxypropyl)-N-(p-fluorobenzyl)carbamate

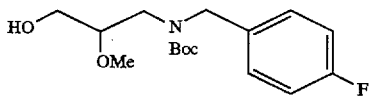

To a solution of tert-butyl N-(2-hydroxy-3-pivaloyloxypropyl)-N-(p-fluorobenzyl)carbamate (6.3 g, 16.5 mmol) in THF (60 ml) was added under ice-cooling sodium hydride (60% suspension in mineral oil: 1.0 g, 24.7 mmol) and then iodomethane (13.0 ml, 48.2 mmol) and the mixture was stirred for 3 days. The reaction mixture was washed with saturated aqueous sodium chloride, dried over anhydrous magnesium sulfate. The solvent was distilled off under reduced pressure and the resulting colorless oily substance was chromatographed using silica gel column to give 2.4 g of the title compound from the fraction from hexane-ethyl acetate as an oily substance. Yield=13%.

¹HNMR(CD₃OD/40° C.)δ1.18(s,9H), 1.47(bs,9H), 3.38 (s,3H), 3.60–3.64(m,1H), 3.94–3.99(m,1H), 4.22–4.27(m, 1H), 4.44–4.57(m,2H), 7.04(t,J=9 Hz,2H), 7.21–7.27(m,2H)

d) tert-Butyl N-(3-hydroxy-2-methoxypropyl)-N-(p-fluorobenzyl)carbamate

To a solution of tert-butyl N-(2-methoxy-3-pivaloyloxypropyl)-N-(p-fluorobenzyl)carbamate (2.3 g, 5.7 mmol) in methanol (45 ml) was added a 10% aqueous solution of tetrabutylammonium hydroxide (15 ml) and the mixture was stirred at room temperature overnight. The solvent was distilled off under reduced pressure and the resulting pale yellow oily substance was chromatographed using silica gel column to give 1.1 g of the title compound from the fraction from hexane-ethyl acetate as a pale yellow oily substance. Yield=62%.

¹HNMR(CD₃OD)δ1.46(bs,9H), 3.31(s,3H), 3.42–3.49 (m,2H), 3.50–3.64(m,1H), 4.44–4.56(m,2H), 7.04(t,J=8 Hz,2H), 7.25(dd,J=5 Hz,8 Hz,2H)

e) tert-Butyl N-(3-amino-2-methoxypropyl)-N-(p-fluorobenzyl)carbamate

This compound was synthesized from tert-butyl N-(3-hydroxy-2-methoxypropyl)-N-(p-fluorobenzyl)carbamate according to the same process as described in Preparation Examples 23c–23d.

N-[4-(tert-Butoxycarbonyl)-5-(p-fluorophenyl)-2-methoxy-4-azapentyl]phthalimide. Yield=99%.

¹HNMR(CDCl₃/40° C.)δ1.40(s,9H), 3.37(s,3H), 6.97(t, J=9 Hz,2H), 7.16–7.20(m,2H), 7.71(dd,J=3 Hz,5 Hz,2H), 7.84(dd,J=3 Hz,5 Hz, 2H)

tert-Butyl N-(3-amino-2-methoxypropyl)-N-(p-fluorobenzyl)carbamate. Yield=92%.

¹HNMR(CD₃OD/40° C.)δ1.44(bs,9H), 2.54–2.59(m,1H), 2.70–2.76(m,1H), 3.37(s,3H), 4.42–4.55(m,2H), 7.04(t,J=9 Hz,2H), 7.25(dd,J=5 Hz,9 Hz,2H)

PREPARATION EXAMPLE 28

5-(p-Fluorophenyl)-2-hydroxy-4-azapentylamine

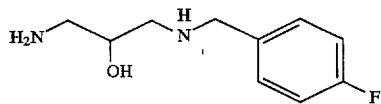

To a solution of p-fluorobenzaldehyde (12.2 g, 98.0 mmol) in methanol (120 ml) was added 1,3-diamino-2-propanol (8.8 g, 98.0 mmol) at room temperature. Then, sodium borohydride (7.4 g, 0.196 mol) was added under ice-cooling and the mixture was stirred at room temperature overnight. The solvent was distilled off under reduced pressure, a 40% aqueous solution of sodium hydroxide (100 ml) was added and extracted with chloroform (100 ml×3). The chloroform layer was dried over anhydrous magnesium sulfate, the solvent was distilled off under reduced pressure and the resulting colorless oily substance was chromatographed using silica gel column to give 6.8 g of the title compound as a colorless oil from the fraction from methylene chloride-methanol-aqueous ammonia. Yield=35%.

¹HNMR(CDCl₃)δ2.57(dd,J=8 Hz,12 Hz,1H), 2.64(dd, J=7 Hz,13 Hz, 1H), 2.71(dd,J=4 Hz,12 Hz,1H), 2.82(dd,J=4 Hz,13 Hz,1H), 3.61–3.66(m,1H), 3.76(d,J=19 Hz,1H), 3.79 (d,J=19 Hz,1H), 7.01(t,J=9 Hz,2H), 7.28(dd,J=5 Hz,9 Hz,2H)

PREPARATION EXAMPLE 29

N-(p-Fluorobenzyl)-N,N'-bis(2-methoxyethyl)-1,3-propanediamine

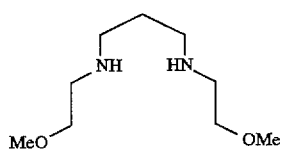

a) N,N'-Bis(methoxyacetyl)-1,3-propanediamine

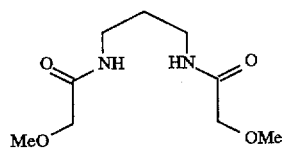

To a solution of methoxyacetic acid (10.0 g, 0.111 mol) in THF (100 ml) were added under ice-cooling N-hydroxysuccinimide (12.8 g, 0.111 mol) and then dicyclohexylcarbodiimide (25.2 g, 0.122 mol) and the mixture was stirred at room temperature for 30 minutes. After the separated materials were filtered off, to the filtrate were added 1,3-diaminopropane (4.19) and triethylamine (16 ml, 0.115 mol) and the mixture was stirred at room temperature overnight. After the solvent was distilled off under reduced pressure, the residue was dissolved in chloroform (200 ml) and washed with water (50 ml×2). After drying over anhydrous magnesium sulfate, the solvent was distilled off under reduced pressure and the resulting residue was chromatographed using silica gel column to give 5.19 of the title compound from the fraction from methylene chloride-methanol as an oily substance. Yield=42%.

¹HNMR(CDCl₃)δ1.71(quint,J=6 Hz,2H), 3.36(quint. J=6 Hz,4H), 3.44(s,6H), 3.91(s,4H), 6.99(bs,2H) MS m/z 218 (M⁺)

b) N,N'-Bis(methoxyethyl)-1,3-propanediamine

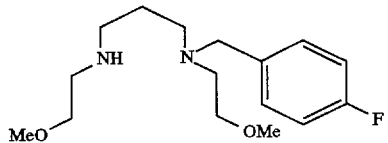

To a solution of N,N'-bis(methoxyacetyl)-1,3-propanediamine (5.1 g, 23.4 mmol) in THF (50 ml) was added a solution of 2N borane dimethyl sulfide complex/THF (50 ml, 0.100 mol) under ice-cooling. The mixture was heated under reflux for 2 hours and then ice-cooled. After 6N hydrochloric acid (30 ml) was added, the solvent was distilled off under reduced pressure. To the resulting residue were added a 40% aqueous solution of sodium hydroxide (100 ml) and a saturated aqueous solution of sodium chloride (100 ml) and then the resulting mixture was extracted with dichloromethane (200 ml×4). The dichloromethane layer was dried over anhydrous magnesium sulfate and the solvent was distilled off under reduced pressure to give 4.5 g of the title compound as a pale yellow oily substance. Yield=100%.

¹HNMR(CDCl₃-TMS)δ1.72(quint,J=7 Hz,2H), 2.12(bs, 2H), 2.72(t,J=7 Hz,4H), 2.79(t,J=5 Hz,4H), 3.36(s,6H), 3.50 (t,J=5 Hz,4H)

c) N-(p-Fluorobenzyl)-N,N'-bis(2-methoxyethyl)-1,3-propanediamine

To a solution of N,N'-bis(methoxyethyl)-1,3-propanediamine (4.5 g, 23.9 mmol) in ethanol (100 ml) was added under ice-cooling a solution of p-fluorobenzyl chloride (2.8 g, 19.1 mmol) in ethanol (50 ml) and the mixture was stirred at room temperature for 5 hours. The solvent was distilled off under reduced pressure and the resulting white oily substance was subjected to silica gel chromatography to obtain 2.3 g of the title compound as a colorless oily substance from the fraction from methylene chloride-methanol-aqueous ammonia. Yield=40%.

¹HNMR(CDCl₃)δ1.94(quint, J=6 Hz,2H), 2.63(t,J=6 Hz,2H), 2.70(t,J=5 Hz,2H), 2.86(t,J=6 Hz,2H), 2.94(t,J=5 Hz,2H), 3.36(s,3H), 3.40(s,3H), 3.53(t,J=5 Hz,2H), 3.62(s, 2H), 3.73(t,J=5 Hz,2H), 7.03(t,J=9 Hz,2H), 7.35(dd,J=5 Hz,9 Hz,2H)

PREPARATION EXAMPLE 30

4-(p-Fluorobenzyl)-4-aza-7-oxaoctylamine

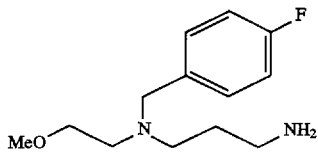

4-(p-Fluorobenzyl)-4-aza-7-oxaoctanol was obtained from methoxyacetic acid and 3-amino-1-propanol according to the same process as described in Preparation Example 29. Then, the title compound was obtained according to the same process as described in Preparation Examples 23c–23d.

a) N-(Methoxyacetyl)-3-amino-1-propanol

Yield=39%.

$^1$HNMR(CDCl$_3$)δ1.71(quint,J=6 Hz,2H), 3.19(t,J=6 Hz,2H), 3.43(s,3H), 3.47(quint,J=6 Hz,2H), 3.64(quint, J=6 Hz,2H), 3.92(s,2H), 6.83(brm,1H)

b) 4-Aza-7-oxaoctanol

Yield=97%.

$^1$HNMR(CDCl$_3$)δ1.70(quint,J=6 Hz,2H), 2.78(t,J=5 Hz,2H), 2.89(t,J=6 Hz,2H), 3.35(s,3H), 3.48(t,J=5 Hz,2H), 3.81(t,J=5 Hz,2H)

c) 4-(p-Fluorobenzyl)-4-aza-7-oxaoctanol

Yield=54%.

$^1$HNMR(CDCl$_3$)δ1.71(quint,J=5 Hz,2H), 2.65(t,J=6 Hz,2H), 2.70(t,J=6 Hz,2H), 3.32(s,3H), 3.49(t,J=6 Hz,2H), 3.59(s,2H), 3.72(t,J=5 Hz,2H), 7.01(t,J=9 Hz,2H), 7.29(dd, J=6 Hz,9 Hz,2H)

d) N-[4-(p-Fluorobenzyl)-4-aza-7-oxaoctyl]phthalimide

Yield=85%.

$^1$HNMR(CDCl$_3$)δ1.85(quint,J=7 Hz,2H), 2.56(t,J=7 Hz,2H), 2.65(t,J=6 Hz,2H), 3.28(s,3H), 3.44(t,J=6 Hz,2H), 3.58(s,2H), 3.71(t,J=7 Hz,2H), 6.93(t,J=9 Hz,2H), 7.28(dd, J=5 Hz,9 Hz,2H), 7.71(dd,J=3 Hz,5 Hz,2H), 7.83(dd,J=3 Hz,5 Hz,2H)

e) 4-(p-Fluorobenzyl)-4-aza-7-oxaoctylamine

Yield=91%.

$^1$HNMR(CDCl$_3$)δ1.60(quint,J=7 Hz,2H), 2.53(t,J=7 Hz,2H), 2.64(t,J=6 Hz,2H), 2.71(t,J=7 Hz,2H), 3.31(s,3H), 3.45(t,J=6 Hz,2H), 3.58(s,2H), 6.98(t,J=9 Hz,2H), 7.28(dd, J=6 Hz,9 Hz,2H)

PREPARATION EXAMPLE 31 tert-Butyl N-(3-aminopropyl)-N-(p-fluorobenzyl) carbamate

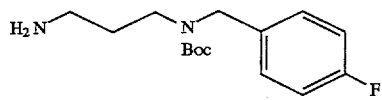

a) N-[4-(tert-Butoxycarbonyl)-5-(p-fluorophenyl)-4-azapentyl]phthalimide

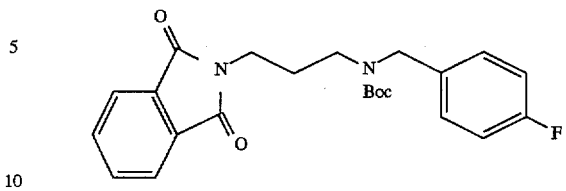

To a solution of p-fluorobenzylamine (2.0 g, 16.0 mmol) and N-(3-bromopropyl)phthalimide (4.3 g, 16.0 mmol) in acetonitrile (100 ml) was added 50% potassium fluoride-on-Celite (10 g) and the mixture was stirred at room temperature for 3 days. After insolubles were filtered off, the solvent was distilled off under reduced pressure to give a colorless oily substance.

To a solution of this compound in dichloromethane (150 ml) was added di-tert-butyldicarbonate (7.0 g) and the mixture was stirred at room temperature for 3 hours. The solvent was distilled off under reduced pressure and the resulting pale yellow oily substance was chromatographed using silica gel column to give 2.1 g of the title compound from the fraction from acetone-hexane as a colorless oily substance. Yield=31%.

$^1$HNMR(CDCl$_3$)δ1.43(s,9H), 1.87(bs,2H), 3.10–3.35 (brm,2H), 3.65(bs,2H), 4.41(s,2H), 6.95(t,J=8 Hz,2H), 7.17 (dd,J=5 Hz,8 Hz,2H), 7.72(dd,J=3 Hz,5 Hz,2H), 7.83(dd, J=3 Hz,5 Hz,2H)

b) tert-Butyl N-(3-aminopropyl)-N-(p-fluorobenzyl) carbamate

To a solution of N-[5-(p-fluorophenyl)-4-(tert-butoxycarbonyl)-4-azapentyl]phthalimide (2.1 g, 5.1 mmol) in methanol (20 ml) was added hydrazine monohydrate (0.4 ml) and the mixture was heated under reflux for 3 hours. After cooling, to the reaction mixture was added dichloromethane (50 ml) and then washed with aqueous ammonia (50 ml×2). The organic layer was dried over anhydrous potassium carbonate and the solvent was distilled off under reduced pressure to give 1.2 g of the title compound as a colorless oily substance. Yield=85%.

$^1$HNMR(CDCl$_3$)δ1.46(s,9H), 1.61(quint,J=7 Hz,2H), 2.67(t,J=7 Hz,2H), 3.25(brm,2H), 4.38(s,2H), 6.99(t,J=9 Hz,2H), 7.17–7.22(brm,2H)

PREPARATION EXAMPLE 32

Dicyclohexylmalonate

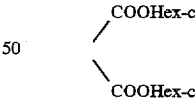

To a solution of dimethylmalonate (33 g, 0.25 mol) in toluene (300 ml) were added cyclohexanol (78 ml, 0.75 mol) and p-toluenesulfonic acid (1.43 g, 7.5 mmol) and the mixture was heated under reflux for 19 hours while methanol was removed using Dean-Stark device. The reaction mixture was diluted with diethyl ether (300 ml) and then washed successively with a saturated aqueous solution of sodium hydrogencarbonate (200 ml×2) and a saturated aqueous sodium chloride (200 ml). The organic layer was dried over anhydrous magnesium sulfate and the solvent was distilled off under reduced pressure. The residue was chromatographed using silica gel column to give 41.18 g of dicyclohexylmalonate from the fraction from ethyl acetate-hexane (1/6). Yield=62%.

¹HNMR(CDCl₃)δ1.18–1.60(m,12H), 1.62–1.78(m,2H), 1.80–1.94(m,2H), 3.33(s,2H), 4.73–4.89(m,2H)

PREPARATION EXAMPLE 33

Diphenylmalonate

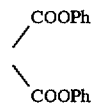

To a solution of Meldrum's acid (15 g, 0.10 mol) in toluene (200 ml) was added phenol (9.1 ml, 0.10 mol) and the mixture was heated under reflux for 2.5 hours. After cooling, phenol (9.1 ml, 0.10 mol) was added and then a solution of dicyclohexylcarbodiimide (23.62 g, 0.12 mol) in toluene (30 ml) was added dropwise under ice-cooling over 30 minutes and the mixture was stirred for 2 hours. The reaction mixture was filtered with Celite and the solvent was distilled off under reduced pressure from the filtrate. The residue was chromatographed using silica gel column to give 26.3 g of diphenylmalonate as a colorless oily substance from the fraction from ethyl acetate-hexane (1/10). Yield=99%.

¹HNMR(CDCl₃)δ3.84(s,2H), 7.15(d,J=9 Hz,4H), 7.20–7.30(m,2H), 7.39(t,J=7 Hz,4H)

PREPARATION EXAMPLE 34

3-Aminomethyl-4-(p-fluorobenzyl)morpholine

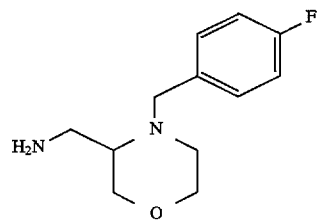

a) 4-(p-Fluorobenzyl)-3-oxomorpholine

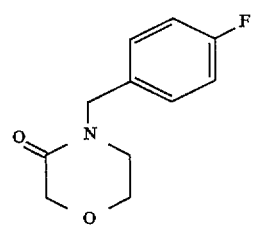

To a solution of 2-(p-fluorobenzylamino)ethanol (53.84 g, 0.318 mol) in chloroform (600 ml) was added triethylamine (95 g, 0.932 mol) and the mixture was stirred under ice-cooling. After chloroacetyl chloride (51 g, 452 mol) was added dropwise gradually, the temperature was allowed to rise to room temperature and the mixture was stirred for 3 hours. After washing with water (900 ml), the chloroform layer was dried over anhydrous magnesium sulfate. After the chloroform was distilled off, the residue was dissolved in methanol (350 ml). To a solution of 28% sodium methylate (135 ml) in methanol (1.2 liter) was added dropwise at room temperature the above-mentioned methanolic solution and the mixture was heated under reflux for 3 hours. After the methanol was distilled off, it was extracted with chloroform, the chloroform layer was dried over anhydrous magnesium sulfate. The chloroform was then distilled off to give a crude oily substance. The oily substance was chromatographed using silica gel column to give the desired product from the fraction from ethyl acetate-hexane. Recrystallization from ether-hexane gave crystals of 4-(p-fluorobenzyl)-3-oxomorpholine (32.53 g). Yield=49%.

¹HNMR(CDCl₃)δ3.27(t,J=5 Hz,2H), 3.84(t,J=5 Hz,2H), 4.24(s,2H), 4.59(s,2H), 7.02(d,J=9 Hz,1H), 7.04(d,J=9 Hz,1H), 7.25(d,J=9 Hz,1H), 7.26(d,J=9 Hz,1H)

b) 4-(p-Fluorobenzyl)-3-nitromethylidenemorpholine

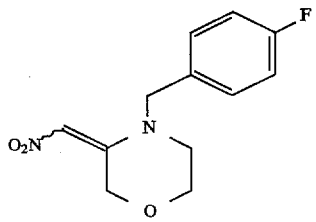

To a solution of 4-(p-fluorobenzyl)-3-oxomorpholine (7.48 g, 35.8 mmol) in methylene chloride (14 ml) was added methyl trifluoromethanesulfonate (5.87 g, 35.8 mmol) and the mixture was stirred at room temperature for 4 hours. To the reaction mixture was added dropwise a sodium methylate solution prepared by dissolving 60% sodium hydride (1.8 g, 45 mmol) in methanol (23 ml) and the mixture was stirred for 30 minutes. Then, nitromethane (3.30 g, 54 mmol) was added and the mixture was stirred for 3 hours. After completion of the reaction, the solvent was distilled off under reduced pressure and at a temperature below 40° C. to obtain the residue. The residue was dissolved in a small amount of ethyl acetate and chromatographed using silica gel column to obtain the desired product from the fraction from ethyl acetate. Crystallization from ethyl acetate-ether gave 2.42 g of 4-(p-fluorobenzyl)-3-nitromethylidenemorpholine as crystals. Yield=27%.

¹HNMR(CDCl₃)δ3.45(t,J=5 Hz,2H), 3.93(t,J=5 Hz,2H), 4.45(s,2H), 5.24(s,2H), 6.78(s,1H), 7.05–7.20(m,4H)

c) 3-Aminomethyl-4-(p-fluorobenzyl)morpholine

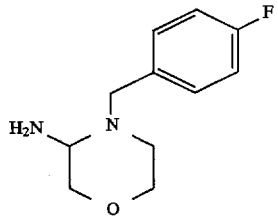

To THF (200 ml) was added a small amount of lithium aluminum hydride, the solvent was dried, lithium aluminum hydride (2.0 g, 53 mmol) was suspended and the mixture was stirred at room temperature. Crystals of 4-(p-fluorobenzyl)-3-nitromethylidenemorpholine (6.58 g, 26.1 mmol) was added gradually and the mixture was stirred at room temperature. A further amount of lithium aluminum hydride (1.3 g, 34 mmol) was added and the mixture was stirred for one hour. Water (3.3 ml), 40% aqueous NaOH (3.3 ml) and water (10 ml) were added in turn and then potassium carbonate (40 g) was added followed by stirring. The reaction mixture was filtered and distilled off. The residue was dissolved in chloroform, dried over potassium carbonate and then the chloroform was distilled off to give 5.44 g of 3-aminomethy-4-(p-fluorobenzyl)morpholine as an oily substance. Yield=93%.

¹HNMR(CDCl₃)δ1.40–1.60(br.2H), 2.20–2.26(m,1H), 2.39–2.44(m,1H), 2.64(td, J=3 Hz,12 Hz,1H), 2.80(dd, J=3 Hz,13 Hz, 1H), 3.05(dd, J=6 Hz,13 Hz,1H), 3.21(d,J=13 Hz,1H), 3.53–3.85(m,4H), 4.05(d,J=13 Hz,1H), 7.00(d,J=9 Hz,1H), 7.02(d,J=9 Hz,1H), 7.28(d,J=9 Hz, 1H), 7.30(d,J=9 Hz,1H)

EXAMPLE 1

5-Cyano-6-[endo-9-(p-fluorobenzyl)-3-oxa-9-azabicyclo-[3.3.1]non-7-ylamino]-4-imino-1,3-dimethyl-3,4-dihydro-(2(1H)-pyrimidinethione

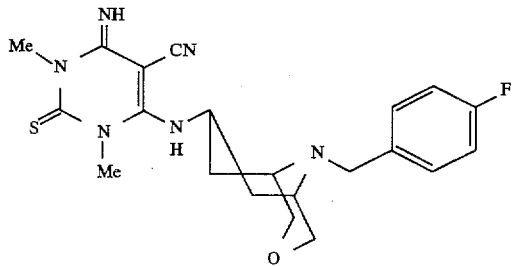

To a solution of endo-7-amino-9-(p-fluorobenzyl)-3-oxa-9-azabicyclo[3.3.1]nonane (0.50 g, 2.00 mmol) in acetonitrile (15 ml) was added 5-cyano-4-imino-1,3-dimethyl-6-methylthio-3,4-dihydro-2(1H)-pyrimidinethione (0.43 g, 1.90 mmol) and the mixture was stirred at room temperature for 5 hours. The reaction mixture was concentrated and purified by silica gel column chromatography to give the title compound (0.52 g) from the fraction from chloroform-methanol-aqueous ammonia (50/1/0.5). Yield=64%.
m.p. 184°–185° C. (recrystallized from ethanol)
¹HNMR(CDCl₃)δ1.58(d,J=16 Hz,2H), 2.51–2.58(m,2H), 2.77(bs,2H), 3.76(d,J=11 Hz,2H), 3.80(s,2H), 3.88(s,3H), 3.90(s,3H), 4.02(d,J=12 Hz,2H), 4.80–4.86(m,1H), 6.99–7.04(m,2H), 7.20(bs,1H), 7.29–7.34(m,2H), 8.23(d,J= 10 Hz,1H)
IR (KBr) 3252, 2938, 2218, 1672, 1600, 1537, 1334, 1126, 838cm⁻¹
MS m/z 428(M⁺)

Then, to a solution of the title compound (0.84 g) in chloroform (10 ml) was added under ice-cooling while stirring a 4N hydrochloric acid-ethyl acetate solution (0.6 ml). The crystal thus separated was recovered by filtration and then dried under reduced pressure to give the corresponding hydrochloride (0.80 g).
m.p. 229°–232° C.

EXAMPLE 2

5-Cyano-6-[endo-9-[3-(p-fluorophenoxy)propyl]-3-oxa-9-azabicyclo[3.3.1]non-7-ylamino]-4-imino-1,3-dimethyl-3,4-dihydro-2(1H)-pyrimidinethione

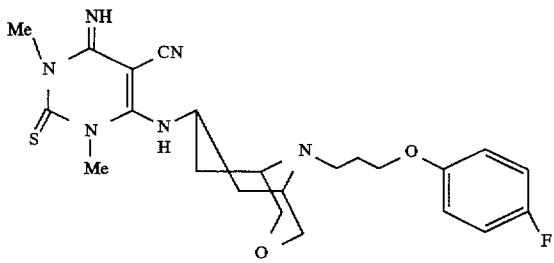

This compound was synthesized from 5-cyano-4-imino-1,3-dimethyl-6-methylthio-3,4-dihydro-2(1H)-pyrimidinethione and endo-7-amino-9-[3-(p-fluorophenoxy)propyl]-3-oxa-9-azabicyclo[3.3.1]nonane according to the same process as described in Example 1. Yield=35%.
m.p. 178°–179° C. (recrystallized from acetonitrile).
¹HNMR(CDCl₃)δ1.57(d,J=16 Hz,2H), 1.88(quint, J=6 Hz,7 Hz,2H), 2.48–2.54(m,2H), 2.80–2.84(m,4H), 3.77(d,J=11 Hz,2H), 3.87(s,3H), 3.90(s,3H), 3.97–4.01(m,4H), 4.74–4.79(m,1H), 6.81–6.86(m,2H), 6.94–7.00(m,2H), 7.20 (br, 1H), 8.21(d,J=10 Hz,1H)
IR(KBr) 3206, 2922, 2194, 1614, 1510, 1110, 757cm⁻¹
MS m/z 472(M⁺)

Then, crystals of the corresponding hydrochloride were obtained in a conventional manner.
m.p. 185°–188° C.

EXAMPLE 3

5-Cyano-4-imino-1,3-dimethyl-6-(endo-3,9-dimethyl-3,9-diazabicyclo[3.3.1]non-7-ylamino)-3,4-dihydro-2(1H)-pyrimidinethione

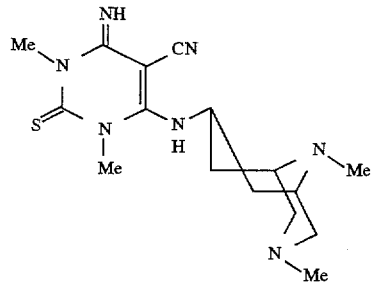

This compound was synthesized from 5-cyano-4-imino-1,3-dimethyl-6-methylthio-3,4-dihydro-2(1H)-pyrimidinethione and endo-7-amino-3,9-dimethyl- 3,9-diazabicyclo[3.3.1]nonane according to the same process as described in Example 1. Yield=46%.
m.p. 184°–185° C. (recrystallized from acetonitrile).
¹HNMR(CDCl₃)δ1.52(d,J=15 Hz,2H), 2.35(s,3H), 2.50(s, 3H), 2.50–2.60(m,4H), 2.69(d,J=12 Hz,2H), 2.92(bs,2H), 3.81(s,3H), 3.90(s,3H), 4.56–4.58(m,1H), 7.15(bs,1H), 10.54(d,J=10 Hz,1H)
MS m/z 347(M⁺)

Then, crystals of the corresponding hydrochloride were obtained in a conventional manner.
m.p. 224°–228° C.

EXAMPLE 4

5-Cyano-4-imino-1,3-dimethyl-6-[endo-9-methyl-3-oxa-9-azabicyclo[3.3.1]non-7-ylamino]-3,4-dihydro-2(1H)-pyrimidinethione

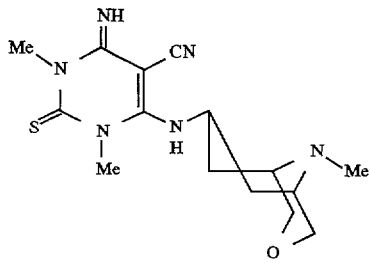

This compound was synthesized from 5-cyano-4-imino-1,3-dimethyl-6-methylthio-3,4-dihydro-2(1H)-pyrimidinethione and endo-7-amino-9-methyl-3-oxa-9- azabicyclo[3.3.1]nonane according to the same process as described in Example 1.

¹HNMR(CDCl₃)δ2.01(d,J=17 Hz,2H), 2.65–2.87(m,2H), 2.81(s,3H), 3.2–3.38(bs,2H), 3.94(s,3H), 3.96(s,3H), 4.10(d, J=13 Hz,2H), 4.20(d,J=13 Hz,2H), 4.70–4.98(m,2H)

IR(film) 3250, 1998, 1635, 1542cm⁻¹

Then, crystals of the corresponding hydrochloride were obtained in a conventional manner.

m.p. 245°–255° C.

EXAMPLE 5

5-Cyano-6-[exo-9-(p-fluorobenzyl)-3-oxa-9-azabicyclo[3.3.1]non-7-ylamino]-4-imino-1,3-dimethyl-3,4-dihydro-2(1H)-pyrimidinethione

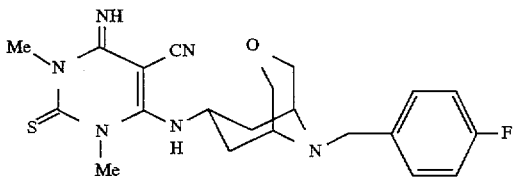

This compound was synthesized from 5-cyano-4-imino-1,3-dimethyl-6-methylthio-3,4-dihydro-2(1H)-pyrimidinethione and exo-7-amino-9-(p-fluorobenzyl)-3-oxa-9-azabicyclo[3.3.1]nonane according to the same process as described in Example 1. Yield=69%.

m.p. 222°–224° C.

¹HNMR(CDCl₃)δ1.02–1.32(m,2H), 1.70–2.14(m,2H), 2.70–2.83(br,2H), 3.65–4.42(m,6H), 3.85(s,3H), 3.88(s,3H), 5.09–5.29(br, 1H), 7.01(t,J=8 Hz,2H), 7.20–7.49(m,3H)

IR(film) 3340, 2498, 1635, 1302cm⁻¹

EXAMPLE 6

5-Cyano-6-[4-(p-fluorobenzyl)-2-morpholinylmethylamino]-4-imino-1,3-dimethyl-3,4-dihydro-2(1H)-pyrimidinethione

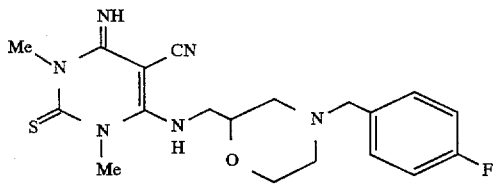

This compound was synthesized from 5-cyano-1,3-dimethyl-4-imino-6-methylthio-3,4-dihydro-2(1H)-pyrimidinethione and 2-aminomethyl-4-(p-fluorobenzyl)morpholine according to the same process as described in Example 1. Yield=75%.

m.p. 92°–96° C.

¹HNMR(CD₃OD)δ1.96(dd,J=10 Hz,11 Hz,1H), 2.20(dd, J=3 Hz,12 Hz, 1H), 2.68(dd, J=1 Hz,12 Hz, 1H), 2.95(d,J= 11 Hz,1H), 3.51(d,J=8 Hz,1H), 3.53(d,J=8 Hz,1H), 3.70(s, 3H), 3.81(s,3H), 3.60–3.92(m,5H), 7.02(d,J=9 Hz,1H), 7.05 (d,J=9 Hz,1H), 7.34(d,J=9 Hz,2H), 7.35(d,J=9 Hz,2H)

MS m/z 402(M⁺)

EXAMPLE 7

5-Cyano-6-[4-(p-fluorobenzyl)-2-morpholinylmethylamino]-4-imino-3-methyl-1-phenyl-3,4-dihydro-2(1H)-pyrimidinethione

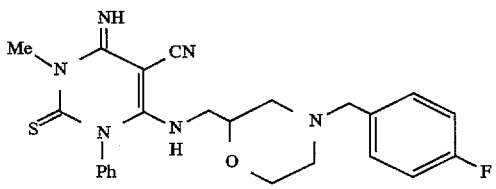

This compound was synthesized from 5-cyano-4-imino-3-methyl-6-methylthio-1-phenyl-3,4-dihydro-2(1H)-pyrimidinethione and 2-aminomethyl-4-(p-fluorobenzyl)morpholine according to the same process as described in Example 1, as a yellow oily substance. Yield=64%.

¹HNMR(CDCl₃)δ1.71(dd, J=10 Hz,11 Hz,1H), 1.89(td,J=11 Hz,3 Hz, 1H), 2.51(dd,J=1 Hz,10 Hz,1H), 2.60(d,J=11 Hz,1H), 3.36(d,J=13 Hz,1H), 3.42(d,J=13 Hz,1H), 3.37–3.52(m,4H), 3.73–3.79(m,1H), 3.91(s,3H), 4.81(bs, 1H), 6.98–7.03(m,2H), 7.20–7.23(m,4H), 7.36(bs,1H), 7.52–7.59(m,3H)

IR(film) 3338, 2200, 1615, 1532, 1510, 1453, 1402, 1257, 1113cm⁻¹

MS m/z 464(M⁺)

Then, crystals of the corresponding hydrochloride were obtained in a conventional manner.

m.p. 179°–181° C.

EXAMPLE 8

1-[5-Cyano-6-[4-(p-fluorobenzyl)-2-morpholinylmethylamino]-1-methyl-2-oxo-3-phenyl-1,2,3,4-tetrahydropyrimidin-4-ylidene]-3-phenylurea

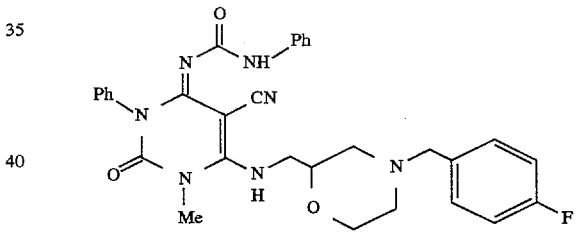

This compound was synthesized from 1-(5-cyano-1-methyl-6-methylthio-2-oxo-3-phenyl-1,2,3,4-tetrahydropyrimidin-4-ylidene)-3-phenylurea and 2-aminomethyl-4-(p-fluorobenzyl)morpholine according to the same process as described in Example 1. Yield=95%.

m.p. 140°–141° C. (recrystallized from ethyl acetate)

¹HNMR(CDCl₃)δ1.95(dd,J=10 Hz,11 Hz,1H), 2.19(dt, J=3 Hz,11 Hz, 1H), 2.68(d,J=11 Hz,1H), 2.76(d,J=11 Hz,1H), 3.46(s,3H), 3.47(s,2H), 3.63(ddd, J=3 Hz,9 Hz,13 Hz,1H), 3.71(dt,J=2 Hz,11 Hz, 1H), 3.78–3.82(m,1H), 3.93(d,J=12 Hz,1H), 3.99(td, J=3 Hz,13 Hz, 1H), 5.76(bs,1H), 6.81(bs, 1H), 6.96–7.50(m,14H)

IR(KBr)3312, 2208, 1703, 1642, 1575, 1508, 1408, 1170cm⁻¹

Then, crystals of the corresponding hydrochloride were obtained in a conventional manner.

m.p. 164°–167° C.

EXAMPLE 9

5-Cyano-6-[4-(p-fluorobenzyl)-2-morpholinylmethylamino]-1,3-dimethyl-2-thioxo-2,3-dihydro-4(1H)-pyrimidinone

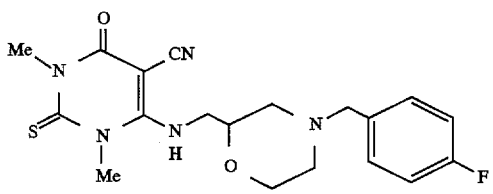

This compound was synthesized from 5-cyano-1,3-dimethyl-6-methylthio-2-thioxo-2,3-dihydro-4(1H)-pyrimidinone and 2-aminomethyl-4-(p-fluorobenzyl) morpholine according to the same process as described in Example 1. Yield=52%.

m.p. 119°–120° C. (recrystallized from hexane-ethyl acetate)

$^1$HNMR(CDCl$_3$)δ1.97(dd,J=10 Hz,11 Hz,1H), 2.21(dt,J=3 Hz,11 Hz, 1H), 2.69(dd,J=2 Hz,12 Hz,1H), 2.80(d,J=11 Hz,1H), 3.46(d,J=13 Hz,1H), 3.51(d,J=13 Hz,1H), 3.60–3.67(m,1H), 3.69–3.75(m,1H), 3.71(s,3H), 3.80–3.83 (m,1H), 3.91–3.95(m,1H), 3.98(s,3H), 4.00–4.06(m,1H), 5.76(bs,1H), 7.00–7.04(m,2H), 7.25–7.28(m,2H)

IR(KBr)2212, 1739, 1644, 1580, 1550, 1448, 1397, 1112, 758cm$^{-1}$

MS m/z 403(M$^+$)

Then, crystals of the corresponding hydrochloride were obtained in a conventional manner.

m.p. 206°–210° C.

EXAMPLE 10

5-Cyano-6-[4-(p-fluorobenzyl)-2-morpholinylmethylamino]-1,3-dimethyl-2,4(1H,3H)-pyrimidinedione

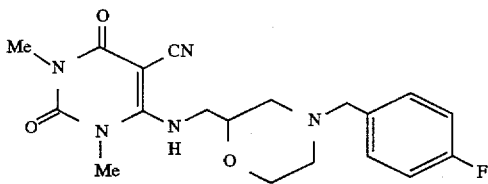

This compound was synthesized from 5-cyano-1,3-dimethyl-6-methylthio-2,4(1H,3H)-pyrimidinedione and 2-aminomethyl-4-(p-fluorobenzyl)morpholine according to the same process as described in Example 1. Yield=92%.

m.p. 127°–128° C. (recrystallized from hexane-ethyl acetate)

$^1$HNMR(CDCl$_3$)δ1.96(dd,J=10 Hz,11 Hz,1H), 2.19(dt,J=3 Hz,11 Hz, 1H), 2.68(dd,J=1 Hz,12 Hz,1H), 2.80(d,J=11 Hz,1H), 3.32(s,3H), 3.46(d,J=13 Hz,1H), 3.47(s,3H), 3.50 (d,J=13 Hz,1H), 3.59–3.66(m,1H), 3.71(dt,J=2 Hz,11 Hz,1H), 3.79–3.85(m,1H), 3.90–3.94(m,1H), 4.05(ddd,J=3 Hz,6 Hz,13 Hz,1H), 5.65(bs,1H), 6.99–7.04(m,2H), 7.25–7.28(m,2H)

IR(KBr) 3344, 2816, 2212, 1720, 1633, 1574, 1511, 1454, 1224, 1117, 1049, 750cm$^{-1}$

MS m/z 387(M$^+$)

Then, crystals of the corresponding hydrochloride were obtained in a conventional manner.

m.p. 205°–211° C.

EXAMPLE 11

5-Cyano-6-[4-(p-fluorobenzyl)-2-morpholinylmethylamino]-3-methyl-1-phenyl-2,4(1H,3H)-pyrimidinedione

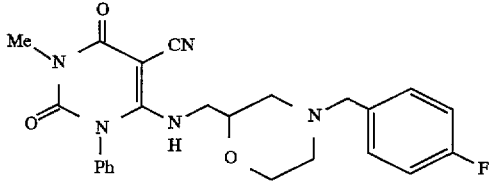

This compound was synthesized from 5-cyano-3-methyl-6-methylthio-1-phenyl-2,4(1H,3H)-pyrimidinedione and 2-aminomethyl-4-(p-fluorobenzyl)morpholine according to the same process as described in Example 1. Yield=88%.

m.p. 181°–184° C. (recrystallized from hexane-ethyl acetate)

$^1$HNMR(CDCl$_3$)δ1.74(dd,J=10 Hz,11 Hz,1H), 1.90(dt,J=3 Hz,11 Hz, 1H), 2.52(dd,J=1 Hz,10 Hz,1H), 2.65(d,J=11 Hz,1H), 3.35(s,3H), 3.36–3.43(m,1H), 3.38(d,J=9 Hz,1H), 3.41(d,J=9 Hz,1H), 3.47–3.58(m,5H), 3.86–3.91(m,1H), 5.10(bs,1H), 6.98–7.02(m,5H), 7.20–7.30(m,4H), 7.58–7.62 (m,3H)

MS m/z 449(M$^+$)

Then, crystals of the corresponding hydrochloride were obtained in a conventional manner.

m.p. 159°–161° C.

IR(KBr) 3352, 2206, 1721, 1562, 1210, 1118, 1044, 760cm$^{-1}$

EXAMPLE 12

6-[4-(3,4-Dichlorobenzyl)-2-morpholinylmethylamino]-5-cyano-1,3-dimethyl-2-thioxo-2,3-dihydro-4(1H)-pyrimidinone

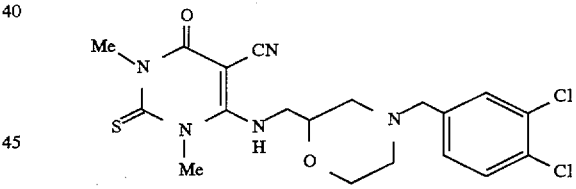

This compound was synthesized from 5-cyano-1,3-dimethyl-6-methylthio-2-thioxo-2,3-dihydro-4(1H)-pyrimidinone and 2-aminomethyl-4-(3,4-dichlorobenzyl) morpholine according to the same process as described in Example 1. Yield=18%.

m.p. 178°–182° C. (recrystallized from ethyl acetate).

$^1$HNMR(CDCl$_3$)δ1.99(t,J=11 Hz,1H), 2.22(dt,J=3 Hz,11 Hz, 1H), 2.68(dd,J=2 Hz,11 Hz,1H), 2.80(dd, J=2 Hz,11 Hz,1H), 3.47(s,2H), 3.60–3.66(m,1H), 3.71(s,3H), 3.70–3.73(m,1H), 3.81–3.89(m,1H), 3.92–3.96(m,1H), 3.98 (s,3H), 4.01–4.07(m,1H), 5.72(bs,1H), 7.15(dd,J=2 Hz,8 Hz,1H), 7.39–7.43(m,2H)

IR(KBr) 3286, 2212, 1657, 1586, 1552, 1469, 1398, 1115, 757cm$^{-1}$

MS m/z 453(M$^+$)

Then, crystals of the corresponding hydrochloride were obtained in a conventional manner.

m.p. 161°–168° C.

EXAMPLE 13

6-[4-(p-Fluorobenzyl)-2-morpholinylamino]-3-methyl-1-phenyl-5-(2-propoxycarbonyl)-2-thioxo-2,3-dihydro-4(1H)-pyrimidinone

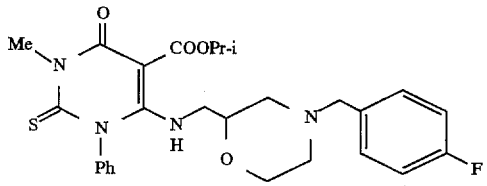

This compound was synthesized from 3-methyl-6-methylthio-1-phenyl-5-(2-propoxycarbonyl)-2-thioxo-2,3-dihydro-4(1H)-pyrimidinone and 2-aminomethyl-4-(p-fluorobenzyl)morpholine according to the same process as described in Example 1. Yield=53%.

$^1$HNMR(CDCl$_3$)δ1.35(d,J=6 Hz,3H), 1.36(d,J=6 Hz,3H), 1.66(t,J=11 Hz,1H), 1.94(dt, J=3 Hz,11 Hz,1H), 2.41(d,J=10 Hz,1H), 2.51(d,J=12 Hz,1H), 2.72–2.84(m,1H), 2.88(dt,J=4 Hz,1H), 3.25–3.45(m,4H), 3.53–3.62(m,1H), 3.73(s,3H), 5.19(quint,J=5 Hz,1H), 6.13–6.29(bs, 1H), 6.99(t,J=9 Hz,2H), 7.09–7.31(m,4H), 7.40–7.59(m,3H)

IR(KBr) 3355, 1668, 1335, 1220, 1105cm$^{-1}$

Then, crystals of the corresponding hydrochloride were obtained in a conventional manner.

m.p. 115°–118° C.

EXAMPLE 14

6-[4-(p-Fluorobenzyl)-2-morpholinylamino]-5-methoxycarbonyl-3-methyl-1-phenyl-2-thioxo-2,3-dihydro-4(1H)-pyrimidinone

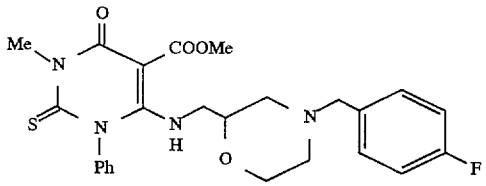

This compound was synthesized from 5-methoxycarbonyl-3-methyl-6-methylthio-1-phenyl-2-thioxo-2,3-dihydro-4(1H)-pyrimidinone and 2-aminomethyl-4-(p-fluorobenzyl)morpholine according to the same process as described in Example 1. Yield=67%.

$^1$HNMR(CDCl$_3$)δ1.65(t,J=11 Hz,1H), 2.00(dt, J=3 Hz,11 Hz,1H), 2.39(d,J=11 Hz,1H), 2.53(d,J=11 Hz,1H), 2.62(ddd, J=4 Hz,7 Hz, 11 Hz,1H), 2.71(dt,J=4 Hz,13 Hz,2H), 3.30–3.49(m,1H), 3.33(d,J=13 Hz,1H), 3.41(d,J=13 Hz,1H), 3.47(dd, J=2 Hz,11 Hz, 1H), 3.65(d,J=11 Hz,1H), 3.73(s, 3H), 3.88(s,3H), 7.00(t,J=9 Hz,2H), 7.06–7.19(m,4H), 7.22–7.38(m,3H)

Then, crystals of the corresponding hydrochloride were obtained in a conventional manner.

m.p. 105°–110° C.

EXAMPLE 15

6-[4-(p-Fluorobenzyl)-2-morpholinylamino]-5-cyclohexyloxycarbonyl-3-methyl-1-phenyl-2-thioxo-2,3-dihydro-4(1H)-pyrimidinone

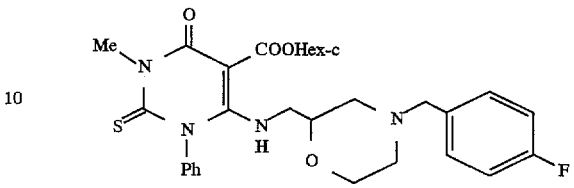

This compound was synthesized from 5-cyclohexyloxycarbonyl-3-methyl-6-methylthio-1-phenyl-2-thioxo-2,3-dihydro-4(1H)-pyrimidinone and 2-aminomethyl-4-(p-fluorobenzyl)morpholine according to the same process as described in Example 1. Yield=23%.

$^1$HNMR(CDCl$_3$)δ1.21–1.48(m,3H), 1.50–1.70(m,4H), 1.74–1.88(m,2H), 1.88–2.04(m,3H), 2.41(d=11 Hz,1H), 2.51(d,J=11 Hz,1H), 2.73–2.84(m,1H), 2.82–2.93(m,1H), 3.29–3.49(m,4H), 3.59(d,J=9 Hz,1H), 3.73(s,3H), 4.84–5.01 (m,1H), 6.10–6.28(br,1H), 6.99(t,J=9 Hz,2H), 7.12–7.38(m, 4H), 7.43–7.62(m,3H)

IR(KBr) 3370, 1668, 1610, 1220cm$^{-1}$

Then, crystals of the corresponding hydrochloride were obtained in a conventional manner.

m.p. 138°–144° C.

EXAMPLE 16

5-n-Butoxycarbonyl-6-[4-(p-fluorobenzyl)-2-morpholinylamino]-3-methyl-1-phenyl-2-thioxo-2,3-dihydro-4(1H)-pyrimidinone

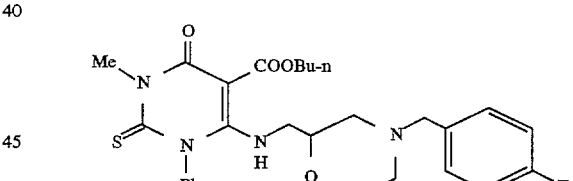

This compound was synthesized from 5-n-butoxycarbonyl-3-methyl-6-methylthio-1-phenyl-2-thioxo-2,3-dihydro-4(1H)-pyrimidinone and 2-aminomethyl-4-(p-fluorobenzyl)morpholine according to the same process as described in Example 1. Yield=35%.

$^1$HNMR(CDCl$_3$)δ0.94(t,J=7 Hz,3H), 1.45(dt,J=7 Hz,15 Hz,2H), 1.58–1.79(m,3H), 1.97(dt,J=3 Hz,11 Hz,1H), 2.40 (d,J=11 Hz,1H), 2.52(d,J=11 Hz,1H), 2.63–2.73(m,1H), 2.79(dt,J=4,13 Hz,1H), 3.25–3.50(m,4H), 3.61(d,J=11 Hz,1H), 3.73(s,3H), 4.27(t,J=7 Hz,2H), 6.02–6.79(br,1H), 6.99(t,J=5 Hz,2H), 7.20(d,J=5 Hz,1H), 7.20(d,J=8 Hz,1H), 7.23–7.32(m,2H), 7.41–7.59(m,3H)

IR(KBr) 3360, 1670, 1610cm$^{-1}$

Then, crystals of the corresponding hydrochloride were obtained in a conventional manner.

m.p. 118°–124° C.

EXAMPLE 17

5-Benzyloxycarbonyl-6-[4-(p-fluorobenzyl)-2-morpholinylamino]-3-methyl-1-phenyl-2-thioxo-2,3-dihydro-4(1H)-pyrimidinone

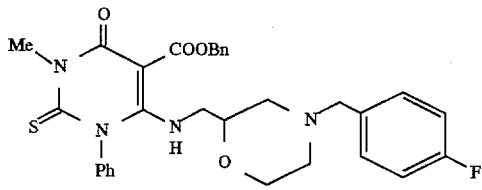

This compound was synthesized from 5-benzyloxycarbonyl-3-methyl-6-methylthio-1-phenyl-2-thioxo-2,3-dihydro-4(1H)-pyrimidinone and 2-aminomethyl-4-(p-fluorobenzyl)morpholine according to the same process as described in Example 1. Yield=55%.

¹HNMR(CDCl₃)δ1.45(t,J=11 Hz,1H), 1.92(dt,J=3 Hz,11 Hz,1H), 2.19(d,J=5 Hz,1H), 2.40–2.50(m,2H), 2.54(dt,J=4 Hz,15 Hz,1H), 3.18–3.25(m,1H), 3.25–3.45(m,3H), 3.54(d, J=11 Hz,1H), 3.74(s,3H), 5.32(d,J=13 Hz,1H), 5.35(d,J=13 Hz,1H), 6.25–6.41(br, 1H), 7.02(t,J=5 Hz,2H), 7.15–7.32 (m,7H), 7.45–7.57(m,5H)

Then, crystals of the corresponding hydrochloride were obtained in a conventional manner.

m.p. 122°–126° C.

EXAMPLE 18

5-Methoxycarbonyl-6-[4-(3,4-dichlorobenzyl)-2-morpholinylamino]-3-methyl-1-phenyl-2-thioxo-2,3-dihydro-4(1H)-pyrimidinone

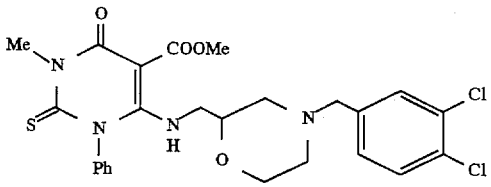

This compound was synthesized from 5-methoxycarbonyl-3-methyl-6-methylthio-1-phenyl-2-thioxo-2,3-dihydro-4(1H)-pyrimidinone and 2-aminomethyl-4-(3,4-dichlorobenzyl)morpholine according to the same process as described in Example 1. Yield=37%.

¹HNMR(CDCl₃)δ1.55(br,d,J=12 Hz,1H), 1.67(br,t,J=10 Hz,1H), 2.38(d,J=11 Hz,1H), 2.53(d,J=11 Hz,1H), 2.58–2.79(m,2H), 3.22–5.55(m,4H), 3.67(d,J=11 Hz,1H), 3.74(s,3H), 3.88(s,3H), 7.09(d,J=8 Hz,1H), 7.19–7.62(m, 7H)

Then, crystals of the corresponding hydrochloride were obtained in a conventional manner.

m.p. 150°–155° C.

EXAMPLE 19

6-[4-(3,4-Dichlorobenzyl)-2-morpholinylamino]-3-methyl-1-phenyl-5-(2-propoxycarbonyl)-2-thioxo-2,3-dihydro-4(1H)-pyrimidinone

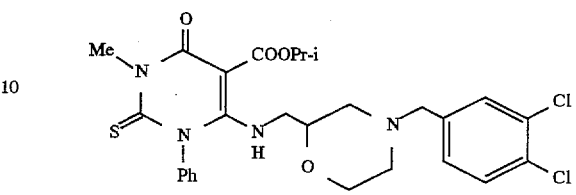

This compound was synthesized from 3-methyl-6-methylthio-1-phenyl-5-(2-propoxycarbonyl)-2-thioxo-2,3-dihydro-4(1H)-pyrimidinone and 2-aminomethyl-4-(3,4-dichlorobenzyl)morpholine according to the same process as described in Example 1. Yield=31%.

¹HNMR(CDCl₃)δ1.46(d,J=6 Hz,3H), 1.47(d,J=6 Hz,3H), 1.62–1.75(m,1H), 1.78(t,J=10 Hz,1H), 2.07(dt,J=3 Hz,15 Hz,1H), 2.50(d,J=11 Hz,1H), 2.60(d,J=11 Hz,1H), 2.80–3.04(m,2H), 3.35–3.62(m,4H), 3.74(d,J=11 Hz,1H), 3.83(s,3H), 5.23–5.39(m,1H), 6.38–6.58(br, 1H), 7.17(d,J=1 Hz,1H), 7.30–7.74(m,7H)

Then, crystals of the corresponding hydrochloride were obtained in a conventional manner.

m.p. 124°–128° C.

EXAMPLE 20

5-Benzyloxycarbonyl-6-[4-(3,4-dichlorobenzyl)-2-morpholinylamino]-3-methyl-1-phenyl-2-thioxo-2,3-dihydro-4(1H)-pyrimidinone

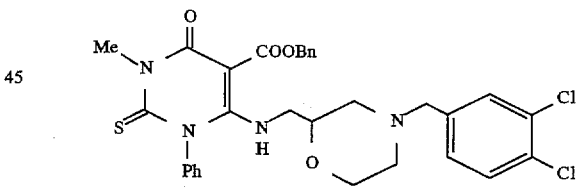

This compound was synthesized from 5-benzyloxycarbonyl-3-methyl-6-methylthio-1-phenyl-2-thioxo-2,3-dihydro-4(1H)-pyrimidinone and 2-aminomethyl-4-(3,4-dichlorobenzyl)morpholine according to the same process as described in Example 1. Yield=55%.

¹HNMR(CDCl₃)δ1.42–1.62(m,4H), 1.88–2.05(m,1H), 2.21 (d,J=11 Hz,1H), 2.42–2.69(m,3H), 3.17–3.48(m,4H), 6.59 (d,J=10 Hz,1H), 5.21–5.41(m,2H), 6.65–6.88(br,1H), 7.04–7.60(m,13H)

Then, crystals of the corresponding hydrochloride were obtained in a conventional manner.

m.p. 155°–159° C.

EXAMPLE 21

6-[4-(p-Trifluoromethylbenzyl)-2-morpholinylamino]-3-methyl-1-phenyl-5-(2-propoxycarbonyl)-2-thioxo-2,3-dihydro-4(1H)-pyrimidinone

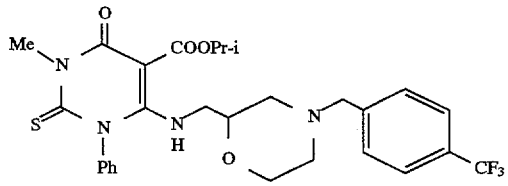

This compound was synthesized from 3-methyl-6-methylthio-1-phenyl-5-(2-propoxycarbonyl)-2-thioxo-2,3-dihydro-4(1H)-pyrimidinone and 2-aminomethyl-4-(p-trifluoromethylbenzyl)morpholine according to the same process as described in Example 1. Yield=40%.

¹HNMR(CDCl₃)δ1.35(d,J=6 Hz,3H), 1.36(d,J=6 Hz,3H), 1.71(t,J=10 Hz,1H), 1.99(dt,J=3 Hz,14 Hz,1H), 2.42(d,J=11 Hz,1H), 2.54(d,J=11 Hz,1H), 2.71–2.92(m,2H), 3.32–3.51 (m,4H), 3.61(d,J=11 Hz,1H), 3.73(s,3H), 5.18(quint,J=6 Hz,1H), 6.22–6.41(br, 1H), 7.18–7.65(m,9H)

IR(film) 3355, 1605, 1320cm⁻¹

Then, crystals of the corresponding hydrochloride were obtained in a conventional manner.

m.p. 89°–93° C.

EXAMPLE 22

6-[4-(p-Trifluoromethylbenzyl)-2-morpholinylamino]-5-methoxycarbonyl-3-methyl-1-phenyl-2-thioxo-2,3-dihydro-4(1H)-pyrimidinone

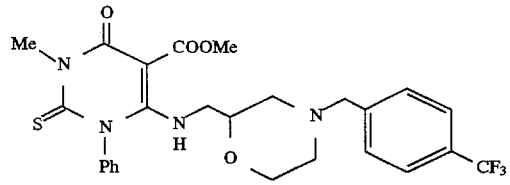

This compound was synthesized from 5-methoxycarbonyl-3-methyl-6-methylthio-1-phenyl-2-thioxo-2,3-dihydro-4(1H)-pyrimidinone and 2-aminomethyl-4-(p-trifluoromethylbenzyl)morpholine according to the same process as described in Example 1. Yield=55%.

¹HNMR(CDCl₃)δ1.60(bs,1H), 1.68(t,J=13 Hz,1H), 2.04(dt, J=3 Hz, 14 Hz,1H), 2.39(d,J=11 Hz,1H), 2.54(d,J=11 Hz,1H), 2.58–2.74(m,2H), 3.31–3.57(m,4H), 3.60–3.78(m, 1H), 3.73(s,3H), 3.87(s,3H), 4.50–4.82(br, 1H), 7.13–7.65 (m,9H)

IR(film) 3360, 1730, 1760cm⁻¹

Then, crystals of the corresponding hydrochloride were obtained in a conventional manner.

m.p. 110°–115° C.

EXAMPLE 23

6-(4-Benzyl-2-morpholinylmethylamino)-5-cyano-4-imino-1,3-dimethyl-3,4-dihydro-2(1H)-pyrimidinethione

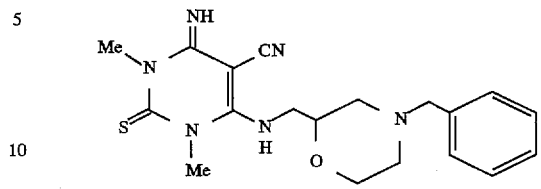

This compound was synthesized from 5-cyano-4-imino-1,3-dimethyl-6-methylthio-3,4-dihydro-2(1H)-pyrimidinethione and 2-aminomethyl-4-benzylmorpholine according to the same process as described in Example 1. Yield=100%.

¹HNMR(CDCl₃)δ2.01(brt, J=10 Hz,1H), 2.09–2.29(brm, 1H), 2.67(brd,J=13 Hz,1H), 2.72–2.93(brm,2H), 3.40–4.00 (m,7H), 3.88(s,6H), 5.18–5.28(br, 1H), 7.05–7.41(m,5H)

Then, crystals of the corresponding hydrochloride were obtained in a conventional manner.

m.p. 202°–209° C.

EXAMPLE 24

6-[4-(3,4-Dichlorobenzyl)-2-morpholinylmethylamino]-5-cyano-4-imino-1,3-dimethyl-3,4-dihydro-2(1H)-pyrimidinethione

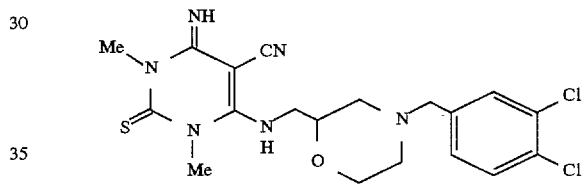

This compound was synthesized from 5-cyano-4-imino-1,3-dimethyl-6-methylthio-3,4-dihydro-2(1H)-pyrimidinethione and 2-aminomethyl-4-(3,4-dichlorobenzyl)-morpholine according to the same process as described in Example 1. Yield=43%.

¹HNMR(CDCl₃)δ1.93–2.10(brm,1H), 2.12–2.28(brm,1H), 2.57–2.89(brm,2H), 3.38–4.00(brm,7H), 3.88(s,6H), 5.30–5.60(brm,1H), 7.09–7.23(brm,1H), 7.35–7.50(brm, 2H)

IR(film) 3330, 2198, 1640, 1500, 1322cm⁻¹

Then, crystals of the corresponding hydrochloride were obtained in a conventional manner.

m.p. 190°–200° C.

EXAMPLE 25

5-Cyano-6-[4-(p-trifluoromethylbenzyl)-2-morpholinylmethylamino]-4-imino-1,3-dimethyl-3,4-dihydro-2(1H)-pyrimidinethione

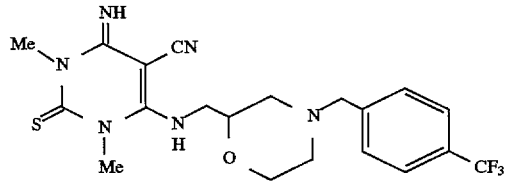

This compound was synthesized from 5-cyano-4-imino-1,3-dimethyl-6-methylthio-3,4-dihydro-2(1H)-pyrimidinethione and 2-aminomethyl-4-(p- trifluoromethylbenzyl)morpholine according to the same process as described in Example 1. Yield=61%.

¹HNMR(CDCl₃)δ1.49–1.70(brm,1H), 1.93–2.09(brm,1H), 2.13–2.29(brm,1H), 2.57–2.75(brm,1H), 2.75–2.93(br, 1H), 3.42–4.02(brm,7H), 3.82(s,3H), 3.88(s,3H), 7.38–7.69(brm, 4H)

Then, crystals of the corresponding hydrochloride were obtained in a conventional manner.

m.p. 206°–209° C. (dec.)

EXAMPLE 26

5-Cyano-4-imino-1,3-dimethyl-6-[4-(4-pyridylmethyl)-2-morpholinylmethylamino]-3,4-dihydro-2(1H)-pyrimidinethione

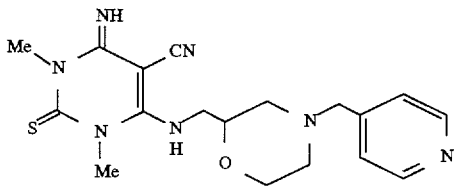

This compound was synthesized from 5-cyano-4-imino-1,3-dimethyl-6-methylthio-3,4-dihydro-2(1H)-pyrimidinethione and 2-aminomethyl-4-(4-pyridylmethyl)morpholine according to the same process as described in Example 1. Yield=53%.

¹HNMR(DMSO-d₆)δ1.86(brt,J=9 Hz,1H), 2.10(brt,J=9 Hz,1H), 2.40–2.63(brm,1H), 2.89(brd, J=11 Hz,1H), 3.18–3.93(brm,7H), 3.70(s,3H), 3.81(s,3H), 7.45–8.38(brm, 4H)

Then, crystals of the corresponding hydrochloride were obtained in a conventional manner.

m.p. 198°–205° C.

EXAMPLE 27

1-[5-Cyano-6-[4-(p-fluorobenzyl)-2-morpholinylmethylamino]-3-methyl-1-phenyl-2-thioxo-1,2,3,4-tetrahydropyrimidin-4-ylidene]-3-phenylurea

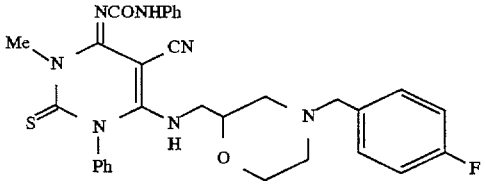

This compound was synthesized from 1-(5-cyano-3-methyl-6-methylthio-1-phenyl-2-thioxo-1,2,3,4-tetrahydropyrimidin-4-ylidene)-3-phenylurea (1.2 g) and 2-aminomethyl-4-(p-fluorobenzyl)morpholine (0.7 g) according to the same process as described in Example 1. Yield=64%.

¹HNMR(CD₃OD/40° C.)δ1.73(dd,J=10 Hz,11 Hz,1H), 1.93 (dt,J=3 Hz, 11 Hz,1H), 2.51(brd,J=11 Hz,1H), 2.60(brd, J=11 Hz,1H), 3.35–3.55(m,6H), 3.66–3.71(m,1H), 3.86(s, 3H), 6.99–7.05(m,3H), 7.24–7.33(m,6H), 7.50–7.56(m,5H)

Then, crystals of the corresponding hydrochloride were obtained in a conventional manner.

m.p. 159°–162° C.

IR(KBr) 3400, 2900, 2600, 2214, 1590, 1542, 1324, 1228, 1117, 692cm⁻¹

EXAMPLE 28

1-[6-[4-(p-chlorobenzyl)-2-morpholinylmethylamino]-5-cyano-3-methyl-1-phenyl-2-thioxo-1,2,3,4-tetrahydropyrimidin-4-ylidene]-3-phenylurea

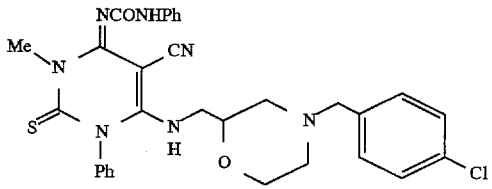

This compound was synthesized from 1-(5-cyano-3-methyl-6-methylthio-1-phenyl-2-thioxo-1,2,3,4-tetrahydropyrimidin-4-ylidene)-3-phenylurea (1.0 g) and 2-aminomethyl-4-(p-chlorobenzyl)morpholine (0.9 g) according to the same process as described in Example 1. Yield=66%.

¹HNMR(CD₃OD/40° C.)δ1.74(dd, J=10 Hz,11 Hz,1H), 1.94 (dt,J=3 Hz, 11 Hz,1H), 2.51(brd, 13 Hz,1H), 2.59(brd,11 Hz,1H), 3.32–3.70(m,7H), 3.86(s,3H), 7.00–7.56(m,14H)

Then, crystals of the corresponding hydrochloride were obtained in a conventional manner. Yield=96%.

m.p. 180°–184° C. (dec.)

IR(KBr) 3400, 2860, 2570, 2214, 1538, 1323, 1120, 1092 692 cm⁻¹

EXAMPLE 29

1-[5-Cyano-6-[4-(p-fluorobenzyl)-2-morpholinylmethylamino]-1,3-dimethyl-2-thioxo-1,2,3,4-tetrahydropyrimidin-4-ylidene]-3-methylurea

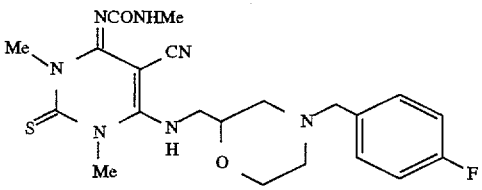

This compound was synthesized from 1-(5-cyano-1,3-dimethyl-6-methylthio-2-thioxo-1,2,3,4-tetrahydropyrimidin-4-ylidene)-3-methylurea and 2-aminomethyl-4-(p-fluorobenzyl)morpholine according to the same process as described in Example 1. Yield=75%.

¹HNMR(CD₃OD/40° C.)δ1.94(dd,J=9 Hz,11 Hz,1H), 2.20 (dt,J=3 Hz, 11 Hz,1H), 2.63–2.67(m,1H), 2.77(s,3H), 2.77–2.82(m,1H), 3.51(s,2H), 3.56(dd, J=8 Hz,14 Hz,1H), 3.66(dt,J=2 Hz,11 Hz,1H), 3.70–3.90(m,3H), 3.77(s,3H), 3.84(s,3H), 7.02(t,J=9 Hz,2H), 7.33(dd,J=6 Hz,9 Hz,2H)

MS m/z 459(M⁺)

Then, crystals of the corresponding hydrochloride were obtained in a conventional manner.

m.p. 145°–155° C.

IR(KBr) 3400, 2950, 1719, 1649, 1515, 1305, 1099, 789cm⁻¹

EXAMPLE 30

1-[5-Cyano-1,3-dimethyl-6-[4-(p-fluorobenzyl)-2-morpholinylmethylamino]-2-thioxo-1,2,3,4-tetrahydropyrimidin-4-ylidene]-3-phenylurea

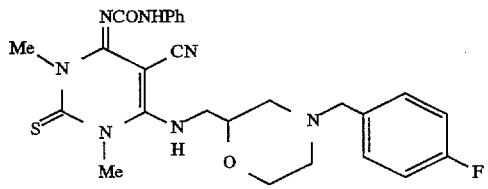

This compound was synthesized from 1-(5-cyano-1,3-dimethyl-6-methylthio-2-thioxo-1,2,3,4-tetrahydropyrimidin-4-ylidene)-3-phenylurea and 2-aminomethyl-4-(p-fluorobenzyl)morpholine according to the same process as described in Example 1. Yield=96%.

$^1$HNMR(CD$_3$OD)δ1.93(dd,J=10 Hz,11 Hz,1H), 2.20(dt,J=3 Hz,11 Hz, 1H), 2.64(brd,J=12 Hz,1H), 2.79(brd,J=11 Hz,1H), 3.50(s,3H), 3.58(dd,J=8 Hz,14 Hz,1H), 3.65(dt,J=2 Hz,11 Hz,1H), 3.74(dd,J=9 Hz,12 Hz,1H), 3.77–3.88(m, 2H), 3.84(s,3H), 3.86(s,3H), 6.98–7.03(m,3H), 7.25(t,J=8 Hz,2H), 7.32(dd, J=5 Hz,9 Hz,2H), 7.53(bs,2H)

MS m/z 521(M$^+$)

Then, crystals of the corresponding hydrochloride were obtained in a conventional manner.

m.p. 152°–155° C.

IR(KBr) 3400, 2920, 2212, 1585, 1401, 1228, 1120cm$^{-1}$

EXAMPLE 31

1-[5-Cyano-6-[4-(p-fluorobenzyl)-2-morpholinylmethylamino]-3-methyl-1-phenyl-2-thioxo-1,2,3,4-tetrahydropyrimidin-4-ylidene]-3-isopropylurea

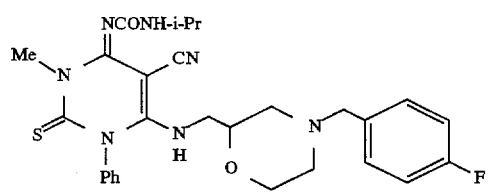

This compound was synthesized from 1-(5-cyano-3-methyl-6-methylthio-1-phenyl-2-thioxo-1,2,3,4-tetrahydropyrimidin-4-ylidene)-3-isopropylurea and 2-aminomethyl-4-(p-fluorobenzyl)morpholine according to the same process as described in Example 1. Yield=56%.

$^1$HNMR(CD$_3$OD)δ1.19(d,J=7 Hz,6H), 1.73(t,J=11 Hz,1H), 1.93(dt,J=3 Hz,11 Hz,1H), 2.52(brd,J=12 Hz,1H), 2.60(brd, J=11 Hz,1H), 3.35–3.55(m,6H), 3.67(dd,J=3 Hz,13 Hz,1H), 3.79(s,3H), 3.93(heptet,J=7 Hz,1H), 7.03(t,J=9 Hz,2H), 7.27–7.32(m,4H), 7.52–7.57(m,3H)

Then, crystals of the corresponding hydrochloride were obtained in a conventional manner.

m.p. 152°–155° C.

IR(KBr) 3400, 1630, 1562, 1514, 1227, 1114cm$^{-1}$

EXAMPLE 32

4-Acetylimino-5-cyano-3-methyl-6-[4-(p-fluorobenzyl)-2-morpholinylmethylamino]-1-phenyl-3,4-dihydro-2(1H)-pyrimidinethione

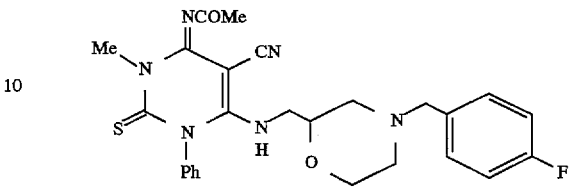

This compound was synthesized from 4-acetylimino-5-cyano-3-methyl-6-methylthio-1-phenyl-3,4-dihydro-2(1H)-pyrimidinethione and 2-aminomethyl-4-(p-fluorobenzyl)morpholine according to the same process as described in Example 1. Yield=47%.

$^1$HNMR(CDCl$_3$/40° C.)δ1.68(dd, J=9 Hz,11 Hz,1H), 1.85 (dt,J=3 Hz, 11 Hz,1H), 2.33(s,3H), 2.48(brd,J=10 Hz,1H), 2.56(brd,J=11 Hz, 1H), 8.80–8.48(m,6H), 3.72–3.80(m,1H), 3.80(s,3H), 6.99(t,J=8 Hz,2H), 7.18–7.22(m,4H), 7.52–7.60 (m,3H)

Then, crystals of the corresponding hydrochloride were obtained in a conventional manner.

m.p. 170°–175° C.

IR(KBr) 3400, 2930, 2216, 1650, 1593, 1531, 1323, 1227, 1123cm$^{-1}$

EXAMPLE 33

6-[4-(p-Chlorobenzyl)-2-morpholinylmethylamino]-5-cyano-4-imino-1,3-dimethyl-3,4-dihydro-2(1H)-pyrimidinethione

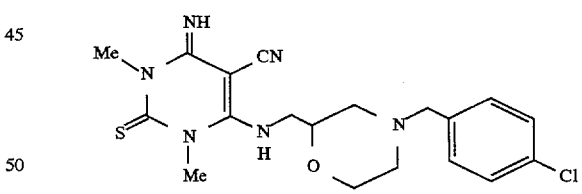

This compound was synthesized from 5-cyano-1,3-dimethyl-4-imino-6-methylthio-3,4-dihydro-2(1H)-pyrimidinethione and 2-aminomethyl-4-(p-chlorobenzyl)morpholine according to the same process as described in Example 1. Yield=60%.

m.p. 94°–97° C.

$^1$HNMR(DMSO-d$_6$)δ1.85(t,J=10 Hz,1H), 2.07(t,J=10 Hz,1H), 2.58(d,J=12 Hz,1H), 2.90(d,J=11 Hz,1H), 3.37–3.86(m,7H), 3.60(s,3H), 3.72(s,3H), 7.32(s,4H), 7.50–7.75(br, 1H), 8.10–8.27(br, 1H)

MS m/z 418(M$^+$)

EXAMPLE 34

6-[4-(Biphenyl-4-ylmethyl)-2-morpholinylmethylamino]-5-cyano-4-imino-1,3-dimethyl-3,4-dihydro-2(1H)-pyrimidinethione

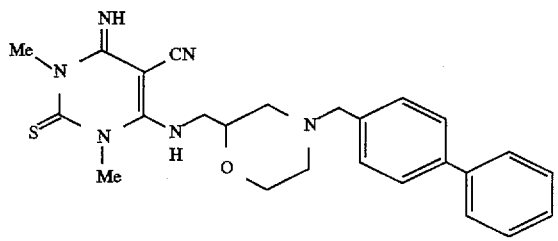

This compound was synthesized from 5-cyano-1,3-dimethyl-4-imino-6-methylthio-3,4-dihydro-2(1H)-pyrimidinethione and 2-aminomethyl-4-(biphenyl-4-ylmethyl)morpholine according to the same process as described in Example 1. Yield=56%.
m.p. 122°–125° C.
$^1$HNMR(CD$_3$OD)δ2.00(t,J=11 Hz,1H), 2.24(dt,J=3 Hz,11 Hz,1H), 2.85(d,J=11 Hz,1H), 3.00(d,J=11 Hz,1H), 3.58(d, J=13 Hz,1H), 3.60(d,J=13 Hz,1H), 3.61–3.80(m,7H), 9.80 (s,3H), 3.83–3.90(m,1H), 7.31(t,J=7 Hz,1H), 7.36–7.45(m, 4H), 7.54–7.62(m,4H)
MS m/z 460 (M$^+$)

Then, crystals of the corresponding hydrochloride were obtained in a conventional manner.
m.p. 202°–204° C.
$^1$HNMR(D$_2$O)δ3.04(t,J=12 Hz,1H), 3.25(dt,J=4 Hz,12 Hz,1H), 3.50(d,J=12 Hz,1H), 3.55(d,J=12 Hz,1H), 3.77–3.95(m,2H), 3.90(s,3H), 3.92(s,3H), 4.08(dd, J=3 Hz,15 Hz,1H), 4.13–4.25(m,2H), 4.43(d,J=13 Hz,1H), 4.47 (d,J=13 Hz,1H), 7.48(t,J=7 Hz,1H), 7.56(t,J=7 Hz,2H), 7.61 (d,J=8 Hz,2H), 7.75(d,J=7 Hz,2H), 7.81(d,J=8 Hz,1H)

EXAMPLE 35

5-Cyano-4-imino-6-[4-(p-methoxybenzyl)-2-morpholinylmethylamino]-1,3-dimethyl-3,4-dihydro-2(1H)-pyrimidinethione

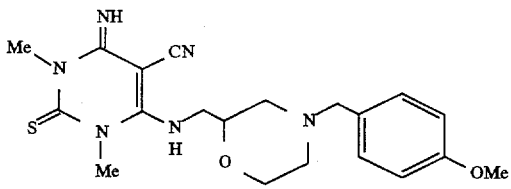

This compound was synthesized from 5-cyano-1,3-dimethyl-4-imino-6-methylthio-3,4-dihydro-2(1H)-pyrimidinethione and 2-aminomethyl-4-(p-methoxybenzyl)morpholine according to the same process as described in Example 1. Yield=25%.
m.p. 93°–96° C.
$^1$HNMR(CDCl$_3$)δ1.90–2.05 (m,1H), 2.10–2.25 (m,1H), 2.60–2.73(m,1H), 2.75–2.90(m,1H), 3.39–3.96(m,7H), 3.81 (s,3H), 3.89(s,3H), 3.90(s,3H), 6.82–6.89(m,2H), 7.17–7.24 (m,2H)
MS m/z 414(M$^+$)

Then, crystals of the corresponding hydrochloride were obtained in a conventional manner.
m.p. 212°–214° C.
$^1$HNMR(D$_2$O)δ3.01(t,J=12 Hz,1H), 3.20(dt,J=3 Hz,12 Hz,1H), 3.45(d,J=12 Hz,1H), 3.52(d,J=12 Hz,1H), 3.72–3.97(m,2H), 3.87(s, 3H), 3.945(s,3H), 3.949(s,3H), 4.08(dd, J=3 Hz,15 Hz,1H), 4.11–4.22(m,2H), 4.30–4.40(m, 2H), 7.09(d,J=9 Hz,2H), 7.46(d,J=9 Hz,2H)

EXAMPLE 36

5-Cyano-6-[1-(p-fluorobenzyl)-3-piperidylmethylamino]-4-imino-1,3-dimethyl-3,4-dihydro-2(1H)-pyrimidinethione

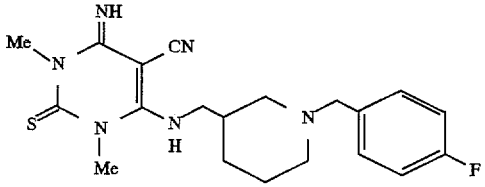

This compound was synthesized from 5-cyano-1,3-dimethyl-4-imino-6-methylthio-3,4-dihydro-2(1H)-pyrimidinethione and 3-aminomethyl-1-(p-fluorobenzyl)piperidine according to the same process as described in Example 1. Yield=42%.

$^1$HNMR(CD$_3$OD)δ1.00–1.15(m,1H), 1.50–2.10(m,6H), 2.75–2.89(m,1H), 2.90–3.03(m,1H), 3.50(s,3H), 3.30–3.60 (m,2H), 3.69(s,2H), 3.81(s,3H), 7.00(d,J=9 Hz,1H), 7.02(d, J=9 Hz,1H), 7.31(d,J=9 Hz,1H), 7.32(d,J=9 Hz,1H)

MS m/z 400(M$^+$)

EXAMPLE 37

5-Cyano-4-imino-6-[1-(p-methoxybenzyl)-3-piperidylmethylamino]-1,3-dimethyl-3,4-dihydro-2(1H)-pyrimidinethione

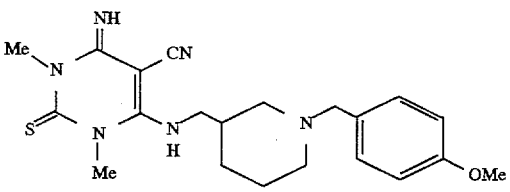

This compound was synthesized from 5-cyano-1,3-dimethyl-4-imino-6-methylthio-3,4-dihydro-2(1H)-pyrimidinethione and 3-aminomethyl-1-(p-methoxybenzyl)piperidine according to the same process as described in Example 1.

Yield=23%.

m.p. 161°–164° C.

$^1$HNMR(CD$_3$OD)δ0.99–1.15(m,1H), 1.55–1.69(m,1H), 1.69–1.77(m,1H), 1.77–1.87(m,2H), 1.82–2.00(m,1H), 2.00–2.13(m,1H), 2.82–2.94(m,1H), 2.94–3.06(m,1H), 3.38–3.60(m,2H), 3.52(s,2H), 3.66(s,3H), 3.79(s,3H), 3.92 (s,3H), 6.86(d,J=9 Hz,2H), 7.23(d,J=9 Hz,2H)

MS m/z 412(M$^+$)

EXAMPLE 38

5-Cyano-4-imino-6-[1-(3,4-dimethoxybenzyl)-3-piperidylmethylamino]-1,3-dimethyl-3,4-dihydro-2(1H)-pyrimidinethione

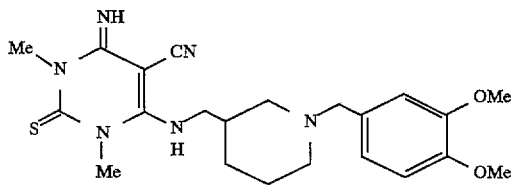

This compound was synthesized from 5-cyano-1,3-dimethyl-4-imino-6-methylthio-3,4-dihydro-2(1H)-pyrimidinethione and 3-aminomethyl-1-(3,4-dimethoxybenzyl)piperidine according to the same process as described in Example 1.

$^1$HNMR(CDCl$_3$)δ1.20–3.00(m,11H), 3.40(d,J=13 Hz,1H), 3.53(d,J=13 Hz,1H), 3.77(s,3H), 3.87(s,3H), 3.88(s,3H), 3.89(s,3H), 6.71–6.87(m,3H)

Then, the corresponding amorphous hydrochloride was obtained in a conventional manner. Yield=23%.

$^1$HNMR(D$_2$O)δ1.23–1.40(m,1H), 1.65–1.84(m,1H), 1.98–2.11(m,2H), 2.25–2.38(m,1H), 2.77(t,J=12 Hz,1H), 2.98(t,J=12 Hz,1H), 3.43(d,J=12 Hz,1H), 3.58(d,J=12 Hz,1H), 3.70–3.87(m,2H), 3.88(s,3H), 3.896(s,3H), 3.900 (s,3H), 3.95(s,3H), 4.25(d,J=13 Hz,1H), 4.36(d,J=13 Hz,1H), 7.07–7.16(m,3H)

MS m/z 442(M$^+$)

EXAMPLE 39

5-Cyano-1,3-dimethyl-6-[1-(p-methoxycarbonylbenzyl)-3-piperidylmethylamino]-4-imino-3,4-dihydro-2(1H)-pyrimidinethione

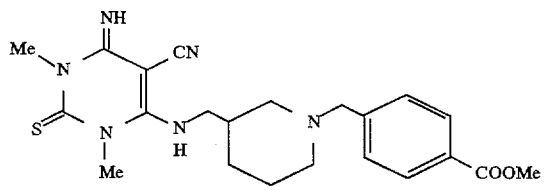

This compound was synthesized from 5-cyano-1,3-dimethyl-4-imino-6-methylthio-3,4-dihydro-2(1H)-pyrimidinethione and 3-aminomethyl-1-(p-methoxycarbonylbenzyl)piperidine according to the same process as described in Example 1. Yield=11%.

m.p. 81°–82° C.

$^1$HNMR(CD$_3$OD)δ1.40–3.00(m,11H), 3.52(d,J=13 Hz,1H), 3.62(d,J=13 Hz,1H), 3.73(s,3H), 3.89(s,3H), 3.92(s,3H), 7.26–7.44(m,2H), 7.99(d,J=8 Hz,2H)

MS m/z 440(M$^+$)

Then, the corresponding hydrochloride was obtained as crystals in a conventional manner.

m.p. 189°–192° C.

$^1$HNMR(D$_2$O)δ1.25–1.41(m,1H), 1.66–1.84(m,1H), 1.98–2.10(m,2H), 2.25–2.40(m,1H), 2.77–2.94(m,1H), 2.94–3.12(m,1H), 3.37–3.50(m,1H), 3.50–3.65(m,3H), 3.65–3.97(m,5H), 3.95(s,3H), 3.96(s,3H), 4.42(d,J=13 Hz,1H), 4.47(d,J=13 Hz,1H), 7.63(d,J=8 Hz,2H), 8.10(d,J=8 Hz,2H)

EXAMPLE 40

5-Cyano-4-imino-1,3-dimethyl-6-[1-(4-piperidylmethyl)-3-piperidylmethylamino]-3,4-dihydro-2(1H)-pyrimidinethione

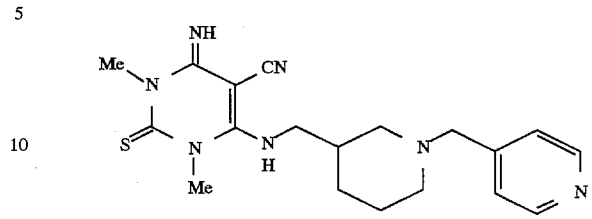

This compound was synthesized from 5-cyano-4-imino-1,3-dimethyl-6-methylthio-3,4-dihydro-2(1H)-pyrimidinethione and 3-aminomethyl-1-(4-pyridylmethyl)piperidine according to the same process as described in Example 1. Yield=50%.

$^1$HNMR(CDCl$_3$)δ1.00–1.19(m,1H), 1.52–2.13(m,6H), 2.65–2.98(brm,2H), 3.25–3.88(m,4H), 3.72(s,3H), 4.00(s,3H), 7.25–7.41(m,3H), 8.26–8.59(br,2H)

Then, the corresponding hydrochloride was obtained as crystals in a conventional manner.

m.p. 215°–218° C. (dec.)

EXAMPLE 41

5-Cyano-6-[1-(p-trifluoromethylbenzyl)-3-piperidylmethylamino]-4-imino-1,3-dimethyl-3,4-dihydro-2(1H)-pyrimidinethione

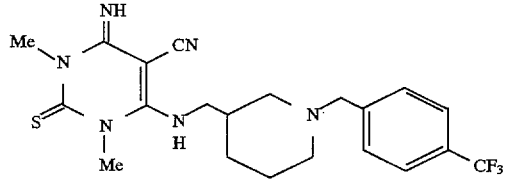

This compound was synthesized from 5-cyano-4-imino-1,3-dimethyl-6-methylthio-3,4-dihydro-2(1H)-pyrimidine thione and 3-aminomethyl-1-(p-trifluoromethylbenzyl)piperidine according to the same process as described in Example 1. Yield=40%.

m.p. 200°–210° C.

$^1$HNMR(CDCl$_3$)δ0.93–1.32(brm,1H), 1.47–2.09(brm,4H), 2.32–3.00(brm,4H), 3.38–3.95(brm,4H), 3.73(s,3H), 3.84(s,3H), 7.44(d,J=7 Hz,2H), 7.57(d,J=8 Hz,2H)

EXAMPLE 42

5-Cyano-6-[1-(p-chlorobenzyl)-3-piperidylmethylamino]-4-imino-1,3-dimethyl-3,4-dihydro-2(1H)-pyrimidinethione

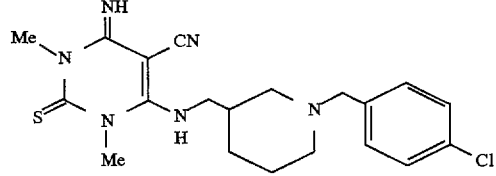

This compound was synthesized from 5-cyano-4-imino-1,3-dimethyl-6-methylthio-3,4-dihydro-2(1H)-pyrimidinethione and 3-aminomethyl-1-(p-chlorobenzyl)piperidine according to the same process as described in Example 1. Yield=86%.

Then, the corresponding hydrochloride was obtained as crystals in a conventional manner.

m.p. 205°–209° C.

¹HNMR(D₂O)δ0.92–1.09(brm,1H), 1.31–1.52(brm,1H), 1.60–1.82 (brm,2H), 1.92–2.13(brm,1H), 2.52(t,J=12 Hz,1H), 2.68(t,J=12 Hz,1H), 2.93–3.70(brm,4H), 3.60(s, 3H), 3.63(s,3H), 3.90–4.12(m,2H), 7.05–7.32(m,4H)

EXAMPLE 43

5-Cyano-6-[1-(3,4-dichlorobenzyl)-3-piperidylmethylamino]-4-imino-1,3-dimethyl-3,4-dihydro-2(1H)-pyrimidinethione

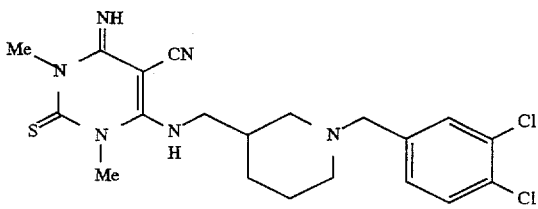

This compound was synthesized from 5-cyano-4-imino-1,3-dimethyl-6-methylthio-3,4-dihydro-2(1H)-pyrimidinethione and 3-aminomethyl-1-(3,4-dichlorobenzyl)piperidine according to the same process as described in Example 1. Yield=52%.

¹HNMR(D₂O)δ0.78–0.90(brm,1H), 1.19–1.38(brm,1H), 1.56–1.62 (brm,2H), 2.38(t,J=11 Hz,1H), 2.50(t,J=12 Hz,1H), 2.97–3.35(m,5H), 3.43(s,3H), 3.49(s,3H), 3.78–3.98(m,2H), 6.92(d,J=5 Hz,1H), 7.16(d,J=5 Hz,1H), 7.22(s, 1H)

IR(KBr) 3350, 2194, 1549, 1495, 1321, 1103, 1030cm⁻¹

Then, the corresponding hydrochloride was obtained as crystals in a conventional manner.

m.p. 215°–218° C.

EXAMPLE 44

5-Cyano-6-[1-(p-fluorobenzyl)-3-azetidinylamino]-4-imino-1,3-dimethyl-3,4-dihydro-2(1H)-pyrimidinethione

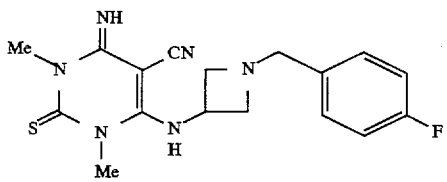

This compound was synthesized from 5-cyano-4-imino-1,3-dimethyl-6-methylthio-3,4-dihydro-2(1H)-pyrimidinethione and 3-amino-1-(p-fluorobenzyl)azetidine according to the same process as described in Example 1. Yield=42%.

¹HNMR(CD₃OD)δ3.23(dd, J=6 Hz,6 Hz,2H), 3.69(s,2H), 3.79(dd, J=6 Hz,6 Hz,2H), 3.79(s,3H), 3.81(s,3H), 4.67 (quint, J=6 Hz,1H), 7.05(t,J=9 Hz,2H), 7.33(dd, J=5 Hz,9 Hz,2H)

Then, the corresponding hydrochloride was obtained as crystals in a conventional manner.

m.p. 150°–155° C.

¹HNMR(D₂O)δ3.94(s,3H), 3.99(s,3H), 4.53(s,2H), 4.52–4.60(m,4H), 5.24(quint,J=7 Hz,1H), 7.25(t,J=9 Hz,2H), 7.54(dd, J=5 Hz,9 Hz,2H)

IR(KBr) 3400, 2950, 2214, 1657, 1573, 1510, 1423, 1331, 1225, 1128, 832, 546, 499cm⁻¹

EXAMPLE 45

5-Cyano-6-[1-(p-fluorobenzyl)-4-piperidinylamino]-4-imino-1,3-dimethyl-3,4-dihydro-2(1H)-pyrimidinethione

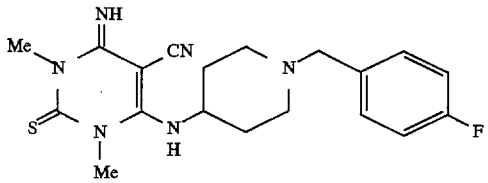

This compound was synthesized from 5-cyano-4-imino-1,3-dimethyl-6-methylthio-3,4-dihydro-2(1H)-pyrimidinethione and 4-amino-1-(p-fluorobenzyl)piperidine according to the same process as described in Example 1. Yield=50%.

¹HNMR(CD₃OD)δ1.62–1.70(brm,2H), 1.84–1.85(brm,2H), 2.19–2.25(brm,2H), 2.85–2.88(brm,2H), 3.53(s,2H), 3.74(s, 3H), 3.80(s,3H),4.06–4.20(m,1H), 7.05(t,J=9 Hz,2H), 7.35 (dd,J=5 Hz,9 Hz,2H)

Then, the corresponding hydrochloride was obtained as crystals in a conventional manner. Yield=94%.

m.p. 250°–252° C.

¹HNMR(D₂O)δ2.06–2.13(brm,2H), 2.39–2.43(brm,2H), 3.18–3.25 (brm,2H), 3.65–3.69(brm,2H), 3.94(s,6H), 4.36 (s,2H), 4.60–4.66(m,1H), 7.25(t,J=9 Hz,2H), 7.54(dd,J=5 Hz,9 Hz,2H)

IR(KBr) 3288, 2926, 2214, 1666, 1565, 1515, 1336, 1127, 731cm⁻¹

EXAMPLE 46

5-Cyano-6-[4-(p-fluorobenzyl)-3-piperazinyl]-4-imino-1,3-dimethyl-3,4-dihydro-2(1H)-pyrimidinethione

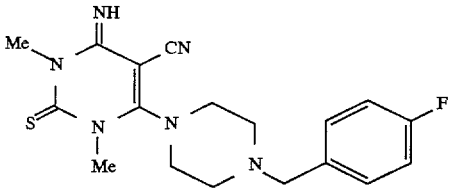

This compound was synthesized from 5-cyano-4-imino-1,3-dimethyl-6-methylthio-3,4-dihydro-2(1H)-pyrimidinethione and 1-(p-fluorobenzyl)piperazine according to the same process as described in Example 1. Yield= 43%.

¹HNMR(CD₃OD)δ2.61(bs,4H), 3.41–3.44(m,4H), 3.58(s, 2H), 3.68(s,3H), 3.77(s,3H), 7.05(t,J=9 Hz,2H), 7.37(dd, J=5 Hz, 9 Hz,2H)

Then, the corresponding hydrochloride was obtained as crystals in a conventional manner.

¹HNMR(D₂O)δ3.59(bs,4H), 3.80(s,3H), 3.91(bs,4H), 3.94 (s,3H), 4.48(s,2H), 7.27(t,J=9 Hz,2H), 7.57(dd, J=5 Hz,9 Hz, 2H)

IR(KBr) 3400, 2996, 2222, 1657, 1543, 1303, 1271, 1132, 1117, 963cm⁻¹ m.p. 203°–205° C.

EXAMPLE 47

5-Cyano-6-[2-[4-(p-fluorobenzyl)-1-piperazinyl]ethylamino]-4-imino-1,3-dimethyl-3,4-dihydro-2(1H)-pyrimidinethione

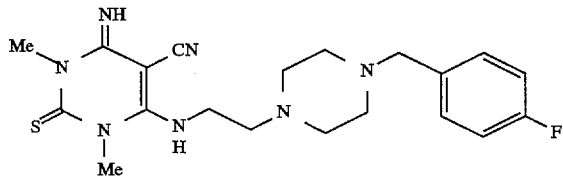

This compound was synthesized from 5-cyano-4-imino-1,3-dimethyl-6-methylthio-3,4-dihydro-2(1H)-pyrimidinethione and 1-(p-fluorobenzyl)-4-(2-aminoethyl)piperazine according to the same process as described in Example 1. Yield=84%.

¹HNMR(CDCl₃/40° C.)δ2.45(bs,4H), 2.54(bs,4H), 2.69(t, J=6 Hz, 2H), 3.47(s,2H), 3.75(t,J=6 Hz,2H), 3.90(s,3H), 3.91(s,3H), 7.00(t,J=9 Hz,2H), 7.26(dd, J=4 Hz,9 Hz,2H)

Then, the corresponding hydrochloride was obtained as crystals in a conventional manner.

m.p. 188°–190° C.

¹HNMR(D₂O)δ3.47(t,J=7 Hz,2H), 3.49(bs,4H), 3.60(bs,4H), 3.95(s,3H), 3.98(s,3H), 4.21(t,J=7 Hz,2H), 4.46(s,2H), 7.26(t, J=9 Hz,2H), 7.55(dd, J=5 Hz,9 Hz,2H)

IR(KBr) 3400, 3.32, 2216, 1652, 1583, 1511, 1459, 1427, 1344, 1329, 1124cm⁻¹

EXAMPLE 48

5-Cyano-6-[N-[2-[1-(p-fluorobenzyl)-2-piperidyl]ethyl]N-methylamino]-4-imino-1,3-dimethyl-3,4-dihydro-2(1H)-pyrimidinethione

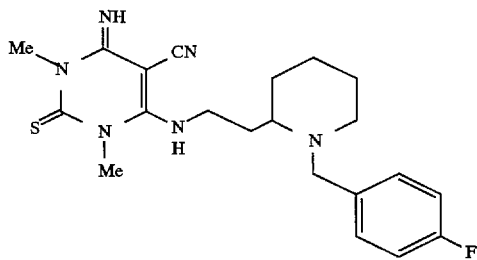

This compound was synthesized from 5-cyano-4-imino-1,3-dimethyl-6-methylthio-3,4-dihydro-2(1H)-pyrimidinethione and 2-(2-methylaminoethyl)-1-(p-fluorobenzyl)piperidine according to the same process as described in Example 1. Yield=70%.

¹HNMR(CDCl₃)δ1.31–1.72(m,6H), 1.73–1.96(m,2H), 2.12–2.24(m,1H), 2.42–2.54(brm,1H), 2.70–2.80(m,1H), 2.95(s,3H), 3.20–3.40(m,3H), 3.58(s,3H), 3.74–3.91(m,1H), 3.84(s,3H), 6.98(t,J=9 Hz,2H), 7.15–7.31(m,2H), 7.37–7.52(brm,1H)

IR(film) 3305, 2205, 1618, 1485, 1405cm⁻¹

EXAMPLE 49

5-Cyano-6-[1-(p-fluorobenzyl)-4-piperidylmethylamino]-4-imino-1,3-dimethyl-3,4-dihydro-2(1H)-pyrimidinethione

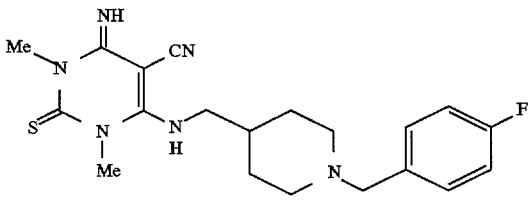

This compound was synthesized from 5-cyano-1,3-dimethyl-4-imino-6-methylthio-3,4-dihydro-2(1H)-pyrimidinethione and 4-aminomethyl-1-(p-fluorobenzyl)piperidine according to the same process as described in Example 1. Yield=22%.

m.p. 186°–190° C.

¹HNMR(CDCl₃)δ1.25–1.45(m,2H), 1.45–1.67(m,1H), 1.70–1.83(m,2H), 1.92–2.07(m,2H), 2.85–2.95(m,2H), 3.45–3.55(m,2H,), 3.69(s,3H), 3.73–3.90(m,2H), 3.92(s, 3H), 6.98(d,J=9 Hz,2H), 7.00(d,J=9 Hz,2H), 7.22–7.32(m, 2H)

MS m/z 400(M⁺)

EXAMPLE 50

5-Cyano-6-[1-(p-fluorobenzyl)-2-piperidylmethylamino]-4-imino-1,3-dimethyl-3,4-dihydro-2(1H)-pyrimidinethione

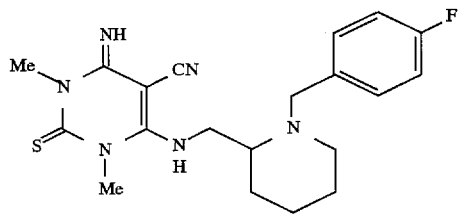

This compound was synthesized from 5-cyano-1,3-dimethyl-4-imino-6-methylthio-3,4-dihydro-2(1H)-pyrimidinethione and 2-aminomethyl-1-(p-fluorobenzyl)piperidine according to the same process as described in Example 1.

¹HNMR(CDCl₃)δ1.30–1.85(m,6H), 2.26–2.36(m,1H), 2.69–2.82(m,1H), 2.85–2.96(m,1H), 3.42(d,J=13 Hz,1H), 3.62–3.72(m,1H), 3.84(s,3H), 3.88(d,J=13 Hz,1H), 3.89(s, 3H), 3.90–4.10(m,1H), 7.02(d,J=8 Hz,1H), 7.04(d,J=8 Hz,1H), 7.18(d,J=8 Hz,1H), 7.19(d,J=8 Hz,1H)

EXAMPLE 51

5-Cyano-4-imino-1,3-dimethyl-6-[4-[2-oxo-2-(1-pyrrolidinyl)-ethyl]-1-piperazinyl]-3,4-dihydro-2(1H)-pyrimidinethione

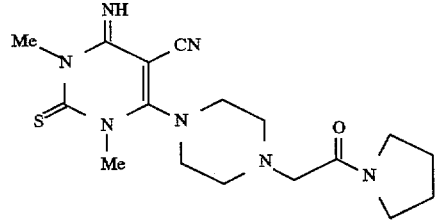

This compound was synthesized from 5-cyano-4-imino-1,3-dimethyl-6-methylthio-3,4-dihydro-2(1H)-pyrimidinethione and 1-[2-oxo-2-(1-pyrrolidinyl)ethyl]- piperazine according to the same process as described in Example 1. Yield=65%.
m.p. 184°–185° C.
¹HNMR(CDCl₃)δ1.84–1.91(m,2H), 1.95–2.01(m,2H), 2.78–2.80(m,4H), 3.24(s,2H), 3.42–3.50(m,8H), 3.69(s,3H), 3.84(s,3H), 7.53(bs, 1H)
IR(KBr) 3450, 2956, 2798, 2202, 1646, 1612, 1454, 1401, 1349, 1115, 797cm⁻¹
MS m/z 375(M⁺)

Then, the corresponding hydrochloride was obtained as crystals in a conventional manner.
m.p. 172°–174° C.

EXAMPLE 52

5-Cyano-6-[4-benzyloxy-3-(p-fluorobenzylamino)butylamino]-4-imino-1,3-dimethyl-3,4-dihydro-2(1H)-pyrimidinethione

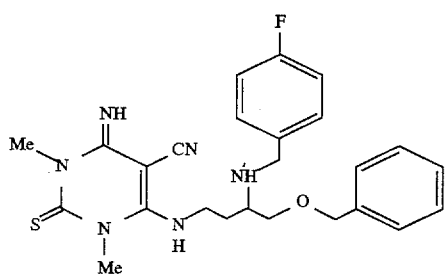

This compound was synthesized from 5-cyano-4-imino-1,3-dimethyl-6-methylthio-3,4-dihydro-2(1H)-pyrimidinethione and 3-(p-fluorobenzylamino)-6-phenyl-5-oxahexylamine according to the same process as described in Example 1. Yield=91%.
¹HNMR(CDCl₃)δ1.72–1.96(m,2H), 2.94–3.05(m,1H), 3.36–3.52(m,1H), 3.47(s,3H), 3.57–3.80(m,2H), 3.81–3.92 (m,3H), 3.85(s,3H), 4.51(d,J=12 Hz,1H), 4.55(d,J=12 Hz,1H), 7.02(t,J=9 Hz,2H), 7.15(d,J=5 Hz,1H), 7.17(d,J=5 Hz,1H), 7.20–7.41(m,6H)
IR(film) 2198, 1605, 1110cm⁻¹

EXAMPLE 53

6-[2-(p-Fluorobenzyl)-3aβ,5α,6aβ-octahydrocyclopenta-[c]pyrrol-5-amino]-5-cyano-4-imino-1,3-dimethyl-3,4-dihydro-2(1H)-pyrimidinethione

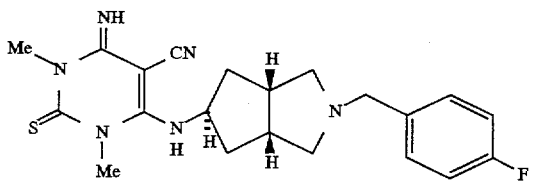

This compound was synthesized from 5-cyano-4-imino-1,3-dimethyl-6-methylthio-3,4-dihydro-2(1H)-pyrimidinethione and 2-(p-fluorobenzyl)-3aβ,5α,6aβ-octahydrocyclopenta[c]pyrrol-5-amine according to the same process as described in Example 1. Yield=81%.
¹HNMR(CDCl₃)δ1.63–1.83(brm,2H), 2.10–2.32(brm,1H), 2.62–2.94(brm,4H), 2.90(s,6H), 3.36–3.42(brm,1H), 3.50–3.59(brm,2H), 3.70–3.90(brm,5H), 4.53–4.72(brm, 1H), 7.00(t,J=9 Hz,2H), 7.22–7.38(m,2H)
IR(film) 3340, 3220, 1995, 1640, 1320, 1110cm⁻¹

Then, the corresponding hydrochloride was obtained as crystals in a conventional manner.
m.p. 236°–241° C.

EXAMPLE 54

6-[2-(p-Fluorobenzyl)-3aα,5α,6aβ-octahydrocyclopenta-[c]pyrrol-5-amino]-5-cyano-4-imino-3-methyl-1-pheny-3,4-dihydro-2(1H)-pyrimidinethione

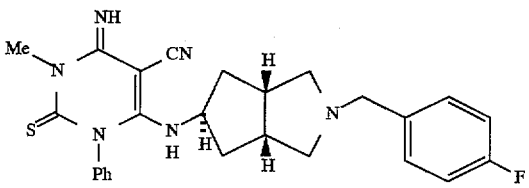

This compound was synthesized from 5-cyano-4-imino-3-methyl-6-methylthio-1-phenyl-3,4-dihydro-2(1H)-pyrimidinethione and 2-(p-fluorobenzyl)-3aβ,5α,6aβ-octahydrocyclopenta[c]pyrrol-5-amine according to the same process as described in Example 1. Yield=26%.
¹HNMR(CDCl₃)δ1.40–1.52(m,2H), 1.78–1.90(m,2H), 2.25–2.42(m,5H), 3.15–3.22(m,1H), 3.41–3.50(m,1H), 3.91 (s,3H), 4.19(d,J=7 Hz,1H), 4.23(d,J=7 Hz,1H), 4.65–4.78 (m,1H), 6.28–6.59(brm,2H), 6.98(t,J=8 Hz,2H), 7.12–7.33 (m,5H), 7.49–7.62(m,2H)
IR(film) 3380, 2260, 1619cm⁻¹

Then, the corresponding hydrochloride was obtained as crystals in a conventional manner.
m.p. 208°–210° C.

EXAMPLE 55

5-Cyano-6-[5-(p-fluorophenyl)-2-hydroxy-4-azapentylamino]-4-imino-1,3-dimethyl-3,4-dihydro-2(1H)-pyrimidinethione

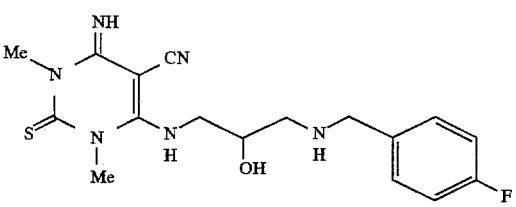

This compound was synthesized from 5-cyano-4-imino-1,3-dimethyl-6-methylthio-3,4-dihydro-2(1H)-pyrimidinethione and 5-(p-fluorophenyl)-1-amino-4-aza-2-pentanol according to the same process as described in Example 1. Yield=84%.
¹HNMR(CD₃OD/40° C.)δ2.65(dd, J=7 Hz,12 Hz,1H), 2.79 (dd,J=4 Hz, 12 Hz, 1H), 3.67–3.70(m,1H), 3.71(s,3H), 3.75–3.77(m,1H), 3.80(s,3H), 3.88–3.93(m,1H), 7.02(t,J=9 Hz,2H), 7.34(dd, J=5 Hz,9 Hz,2H)

Then, the corresponding hydrochloride was obtained as crystals in a conventional manner. Yield=92%.
m.p. 200° C.
¹HNMR(D₂O/40° C.)δ3.13(dd,J=11 Hz,13 Hz,1H), 3.30(dd, J=2 Hz, 13 Hz,1H), 3.82(dd,J=8 Hz,15 Hz,1H), 3.96(s,3H), 3.97(s,3H), 4.04(dd,J=3 Hz,15 Hz,1H), 4.29–4.34(brm,1H), 4.33(s,2H), 7.23(t,J=9 Hz,2H), 7.53(dd,J=5 Hz, 9 Hz,2H)
IR(KBr) 3340, 2950, 2214, 1657, 1600, 1514, 1331, 1161cm⁻¹

EXAMPLE 56

5-Cyano-6-[N-[5-p-fluorophenyl-4-(2-methoxyethyl)-4-azapentyl]-N-(2-methoxyethyl)amino]-4-imino-1,3-dimethyl- 3,4-dihydro-2(1H)-pyrimidinethione

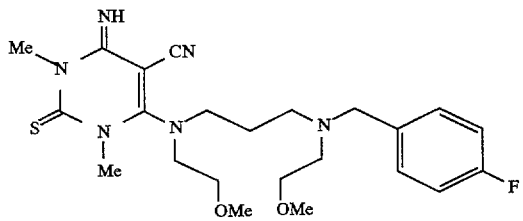

This compound was synthesized from 5-cyano-1,3-dimethyl-4-imino-6-methylthio-3,4-dihydro-2(1H)-pyrimidinethione and N-(p-fluorobenzyl)-N,N'-bis(2-methoxyethyl)-1,3-propanediamine according to the same process as described in Example 1. Yield=25%.

$^1$HNMR(CDCl$_3$)δ1.68(quint,J=7 Hz,2H), 2.50(t,J=6 Hz,2H), 2.63(t,J=6 Hz,2H), 3.25(t,J=7 Hz,2H), 3.30(s,3H), 3.32(s,3H), 3.42(t,J=6 Hz,4H), 3.45–3.49(m,2H), 3.55(s,2H), 3.58(s,3H), 3.85(s,3H), 6.98(t,J=9 Hz,2H), 7.23(dd,J=6 Hz,9 Hz,2H)

Then, the corresponding hydrochloride was obtained as crystals in a conventional manner.

m.p. 150°–160° C.

IR(KBr) 3400, 2930, 2220, 1655, 1575, 1520, 1340, 1228, 1120cm$^{-1}$

MS m/z 476(M$^+$)

EXAMPLE 57

5-Cyano-1,3-dimethyl-6-[4-(p-fluorobenzyl)-4-aza-7-oxaoctylamino]-4-imino-3,4-dihydro-2(1H)-pyrimidinethione

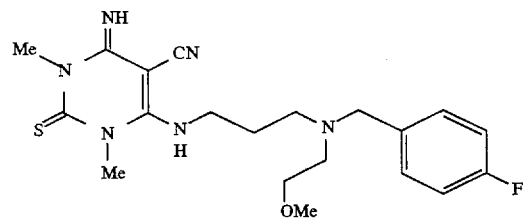

This compound was synthesized from 5-cyano-4-imino-1,3-dimethyl-6-methylthio-3,4-dihydro-2(1H)-pyrimidinethione and 4-(p-fluorobenzyl)-4-aza-7-oxaoctylamine according to the same process as described in Example 1. Yield=87%.

$^1$HNMR(CDCl$_3$)δ1.84–1.88(brm,2H), 2.69(t,J=5 Hz,4H), 3.27(s,3H), 3.41(t,J=5 Hz,2H), 3.69(s,2H), 3.77(s,3H), 3.83 (brm,2H), 3.90(s,3H), 7.03(t,J=9 Hz,2H), 7.19(dd,J=5 Hz, 9 Hz,2H)

Then, the corresponding hydrochloride was obtained as crystals in a conventional manner.

m.p. 135°–138° C.

$^1$HNMR(D$_2$O/40° C.)δ2.21(bs,2H), 3.31(t,J=7 Hz,2H), 3.38 (s,3H), 3.48(t,J=5 Hz,2H), 3.79(bs,2H), 3.85(t,J=7 Hz,2H), 3.92(s,3H), 3.97(s,3H), 4.46(bs,2H), 7.24(t,J=9 Hz,2H), 7.53–7.58(m,2H)

IR(KBr) 3400, 2214, 1651, 1591, 1512, 1451, 1422, 1353, 1331, 1227, 1127cm$^{-1}$

EXAMPLE 58

5-Cyano-6-[7-(p-fluorophenyl)-3,6-diaza-1-heptylamino]-4-imino-1,3-dimethyl-3,4-dihydro-2(1H)-pyrimidinethione

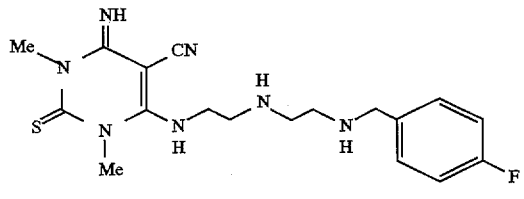

a) 5-Cyano-6-[7-(p-fluorophenyl)-3,6-di(tert-butoxycarbonyl)-3,6-diaza-1-heptylamino]-4-imino-1,3-dimethyl-3,4-dihydro-2(1H)-pyrimidinethione

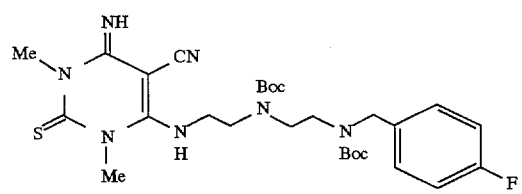

To a solution of tert-butyl N-(5-amino-3-tert-butoxycarbonyl-3-azapentyl)-N-(p-fluorobenzyl)carbamate (2.7 g) in acetonitrile (9 ml) was added 5-cyano-4-imino-1,3-dimethyl-6-methylthio-3,4-dihydro-2(1H)-pyrimidinethione (1.5 g) and the mixture was stirred at room temperature overnight. The product thus separated out was recovered by filtration, washed with acetonitrile, dried under reduced pressure to give 3.5 g of the title compound as a white powder. Yield=90%.

$^1$HNMR(CDCl$_3$/40° C.)δ1.46(bs,18H), 3.30(bs,4H), 3.54 (bs,2H), 3.80–3.95(m,8H), 4.40(bs,2H), 7.03(t,J=9 Hz,2H), 7.18(bs,2H)

b) 5-Cyano-6-[7-(p-fluorophenyl)-3,6-diaza-1-heptylamino]-4-imino-1,3-dimethyl-3,4-dihydro-2(1H)-pyrimidinethione To a solution of 5-cyano-6-[7-(p-fluorophenyl)-3,6-di(tert-butoxycarbonyl)-3,6-diaza-1-heptylamino]-4-imino-1,3-dimethyl-3,4-dihydro-2(1H)-pyrimidinethione (1.4 g) in chloroform (20 ml) and methanol (20 ml) was added a solution of 4N hydrochloric acid in ethyl acetate (7 ml) and the mixture was stirred at 45° C. for 5 hours. The product thus separated out was recovered by filtration, washed with ethyl acetate, dried under reduced pressure to give 2.8 g of the hydrochloride of the title compound as a white powder. Yield=100%.

m.p. 152°–156° C.

$^1$HNMR(D$_2$O/40° C.)δ3.55(bs,4H), 3.58(t,J=6 Hz,2H), 3.96 (s,3H), 4.00(s,3H), 4.24(t,J=6 Hz,2H), 4.33(s,2H), 7.24(t, J=9 Hz,2H), 7.53(m,2H)

IR(KBr) 3410, 3000, 2760, 2214, 1650, 1571, 1513, 1423, 1333, 1227, 1164cm$^{-1}$

EXAMPLE 59

5-Cyano-6-[7-(p-fluorophenyl)-6-aza-3-oxaheptylamino]-4-imino-1,3-dimethyl-3,4-dihydro-2(1H)-pyrimidinethione

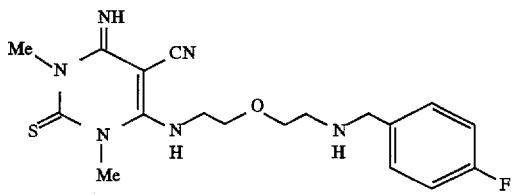

5-Cyano-6-[7-(p-fluorophenyl)-6-aza-6-(tert-butoxycarbonyl)-3-oxaheptylamino]-4-imino-1,3-dimethyl-3,4-dihydro-2(1H)-pyrimidinethione was obtained from tert-butyl N-(5-amino-3-oxapentyl)-N-(p-fluorobenzyl)carbamate and 5-cyano-4-imino-1,3-dimethyl-6-methylthio-3,4-dihydro-2(1H)-pyrimidinethione according to the same process as in Example 58a. Yield=80%.

$^1$HNMR(CDCl$_3$/40° C.)61.44(brm,9H), 3.41(brm,2H), 3.59 (brm,2H), 3.66(brm,2H), 3.82(t,J=5 Hz,2H), 3.88(s,6H), 4.43(brm,2H), 7.00(t,J=8 Hz,2H), 7.19(brm,2H)

Then, the hydrochloride of the title compound was obtained as crystals according to the same process as described in Example 58b. Yield=91%.

m.p. 204°–206° C.

$^1$HNMR(D$_2$O/40° C.)δ3.33(t,J=4 Hz,2H), 3.85(m,4H), 3.93 (s,6H), 4.07(t,J=5 Hz,2H), 4.28(s,2H), 7.23(t,J=9 Hz,2H), 7.48–7.53(m,2H)

IR(KBr) 3288, 2914, 2218, 1673, 1587, 1543, 1518, 1451, 1356, 1344, 1130, 699cm$^{-1}$

EXAMPLE 60

5-Cyano-6-[5-(p-fluorophenyl)-4-azapentylamino]-4-imino-3,4-dihydro-1,3-dimethyl-2(1H)-pyrimidinethione

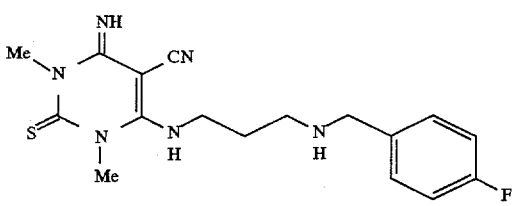

5-Cyano-1,3-dimethyl-6-[5-(p-fluorophenyl)-4-(tert-butoxycarbonyl)-4-azapentylamino]-4-imino-3,4-dihydro-2 (1H)-pyrimidinethione was obtained from tert-butyl N-(3-aminopropyl)-N-(p-fluorobenzyl)carbamate and 5-cyano-1,3-dimethyl-4-imino-6-methylthio-3,4-dihydro-2(1H)-pyrimidinethione according to the same process as described in Example 58a. Yield=91%.

$^1$HNMR(CD$_3$OD)δ1.46(bs,9H), 1.84(bs,9H), 3.31(s,3H), 3.31(s,3H), 3.60(bs,2H), 3.74(bs,2H), 4.43(s,2H), 7.02(t,J=9 Hz,2H), 7.25(dd,J=5 Hz,9 Hz,2H)

Then, the hydrochloride of the title compound was obtained as crystals according to the same process as described in Example 58b. Yield=84%.

m.p. 266°–269° C.

$^1$HNMR(D$_2$O)δ2.19(quint,J=8 Hz,2H), 3.20(t,J=8 Hz,2H), 3.90(t,J=8 Hz,2H), 3.95(s,3H), 3.96(s,3H), 4.28(s,2H), 7.22 (t,J=9 Hz,2H), 7.51(dd,J=5 Hz,9 Hz,2H)

IR(KBr) 3028, 2212, 1651, 1592, 1549, 1511, 1459, 1433, 1351, 1333, 1223, 1127cm$^{-1}$

EXAMPLE 61

5-Cyano-6-[6-(p-fluorophenyl)-5-azahexylamino]-4-imino-1,3-dimethyl-3,4-dihydro-2(1H)-pyrimidinethione

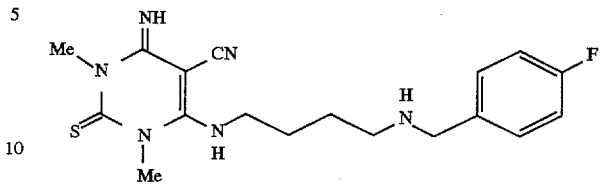

5-Cyano-6-[6-(p-fluorophenyl)-5-(tert-butoxycarbonyl)-5-azahexylamino]-4-imino-1,3-dimethyl-3,4-dihydro-2(1H)-pyrimidinethione was obtained from tert-butyl N-(4-aminobutyl)-N-(p-fluorobenzyl)carbamate and 5-cyano-4-imino-1,3-dimethyl-6-methylthio-3,4-dihydro-2(1H)-pyrimidinethione according to the same process as described in Example 58a. Yield=98%.

$^1$HNMR(CDCl$_3$/40° C.)δ1.45(bs,9H), 1.61(bs,4H), 3.23(bs,2H), 3.62–4.04(bs,2H), 3.89(s,6H), 4.38(s,2H), 6.99–7.02 (bs,2H), 7.18(bs,2H)

Then, the hydrochloride of the title compound was obtained as crystals according to the same process as described in Example 58b. Yield=79%.

m.p. 239°–241° C.

$^1$HNMR(D$_2$O/40° C.)δ1.83(bs,4H), 3.13(t,J=7 Hz,2H), 3.83 (t,J=7 Hz,2H), 3.95(s,3H), 3.95(s,3H), 4.25(s,2H), 7.23(t, J=8 Hz,2H), 7.55(dd, J=5 Hz,8 Hz,2H)

IR(KBr) 3348, 3038, 2208, 1666, 1593, 1564, 1543, 1351, 1332, 1130, 698cm$^{-1}$

EXAMPLE 62

5-Cyano-6-[7-(p-fluorophenyl)-6-azaheptylamino]-4-imino-1,3-dimethyl-3,4-dihydro-2(1H)-pyrimidinethione

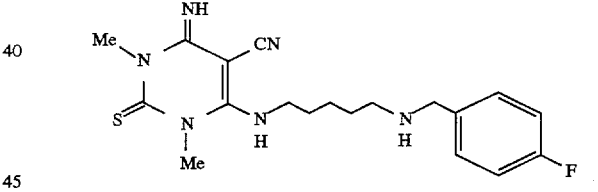

5-Cyano-6-[7-(p-fluorophenyl)-6-(tert-butoxycarbonyl)-6-azaheptylamino]-4-imino-1,3-dimethyl-3,4-dihydro-2 (1H)-pyrimidinethione was obtained from tert-butyl N-(5-aminopentyl)-N-(p-fluorobenzyl)carbamate and 5-cyano-4-imino-1,3-dimethyl-6-methylthio-3,4-dihydro-2(1H)-pyrimidinethione according to the same process as described in Example 58a. Yield=94%.

$^1$HNMR(CD$_3$OD/40° C.)δ1.33–1.39(brm,2H), 1.44(s,9H), 1.50–1.56(brm,2H), 1.61–1.66(brm,2H), 3.61(t,J=7 Hz,2H), 3.77(s,3H), 3.80(s,3H), 4.40(s,2H), 7.03(t,J=9 Hz,2H), 7.22–7.27(brm,2H)

Then, the hydrochloride of the title compound was obtained as crystals according to the same process as described in Example 58b. Yield=85%.

m.p. 149°–151° C.

$^1$HNMR(D$_2$O/50° C.)δ1.45–1.51(brm,2H), 1.71–1.81(brm, 4H), 3.09(t,J=8 Hz,2H), 3.80(t,J=8 Hz,2H), 3.95(s,6H), 4.24 (s,2H), 7.23(t,J=9 Hz,2H), 7.48–7.53(brm,2H)

IR(KBr) 3418, 1665, 1589, 1561, 1542, 1510cm$^{-1}$

MS m/z 388(M$^+$)

EXAMPLE 63

5-Cyano-6-[5-(p-fluorophenyl)-2-methoxy-4-azapentylamino]-4-imino-1,3-dimethyl-3,4-dihydro-2(1H)-pyrimidinethione

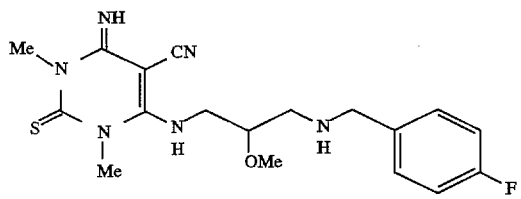

5-Cyano-6-[4-(tert-butoxycarbonyl)-5-(p-fluorophenyl)-2-methoxy-4-azapentylamino]-4-imino-1,3-dimethyl-3,4-dihydro-2(1H)-pyrimidinethione was obtained from tert-butyl N-(3-amino-2-methoxypropyl)-N-(p-fluorobenzyl) carbamate and 5-cyano-4-imino-1,3-dimethyl-6-methylthio-3,4-dihydro-2(1H)-pyrimidinethione according to the same process as described in Example 58a. Yield=74%.
m.p. 150°–154° C.
$^1$HNMR(CD$_3$OD/40° C.)δ1.45(bs,9H), 3.40(s,3H), 3.72(bs,3H), 3.80(s,3H), 4.44–4.56(m,2H), 7.02(t,J=9 Hz,2H), 7.32 (dd, J=5 Hz,9 Hz,2H)

Then, the hydrochloride of the title compound was obtained as crystals according to the same process as described in Example 58b. Yield=98%.
$^1$HNMR(D$_2$O/50° C.)δ3.15–3.20(brm,1H), 3.31–3.35(brm,1H), 3.49(s,3H), 3.96(s,6H), 4.04(bs,3H), 4.34(s,2H), 7.24 (t,J=9 Hz,2H), 7.54(bs,2H)
IR(KBr) 2214, 1731, 1652, 1543, 1509, 1423, 1329, 1224, 1163, 826, 737, 703cm$^{-1}$
MS m/z 390(M$^+$)

EXAMPLE 64

5-Cyano-6-[7-(p-fluorophenyl)-6-aza-3-oxaheptylamino]-1,3-dimethyl-2-thioxo-2,3-dihydro-4(1H)-pyrimidinone

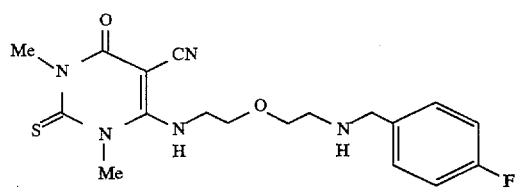

6-[6-(tert-Butoxycarbonyl)-7-(p-fluorophenyl)-6-aza-3-oxaheptylamino]-5-cyano-1,3-dimethyl-2-thioxo-2,3-dihydro-4(1H)-pyrimidinone was obtained from tert-butyl N-(p-fluorobenzyl)-N-(5-amino-3-oxapentyl)carbamate and 5-cyano-1,3-dimethyl-6-methylthio-2-thioxo-2,3-dihydro-4(1H)-pyrimidinone according to the same process as described in Example 58a. Yield=79%.
$^1$HNMR(CDCl$_3$)δ1.43(bs,9H), 3.42(bs,2H), 3.59(t,J=5 Hz,2H), 3.72(s,3H), 3.65–3.74(m,2H), 3.89–4.00(m,5H), 6.20(bs,1H), 7.00–7.04(m,2H), 7.17–7.20(m,2H)
IR(film) 3298, 2972, 2212, 1647, 1509, 757cm$^{-1}$ Then, the hydrochloride of the title compound was obtained as crystals according to the same process as described in Example 58b. Yield=82%.
m.p. 211°–213° C.
$^1$HNMR(DMSO-d$_6$)δ3.08(d,J=5 Hz,2H), 3.55(s,3H), 3.71–3.77(m,4H), 3.86–3.89(m,2H), 3.89(s,3H), 4.16(s,2H), 7.24–7.28(m,2H), 7.59–7.63(m,2H), 9.25(b,1H)
IR(KBr) 3266, 2928, 2206, 1650, 1580, 1520, 1440, 1402, 1342, 1237, 1130, 1112, 833, 752cm$^{-1}$

EXAMPLE 65

5-Ethoxycarbonyl-6-[7-(p-fluorophenyl)-6-aza-3-oxaheptylamino]-1,3-dimethyl-2-thioxo-2,3-dihydro-4(1H)-pyrimidinone

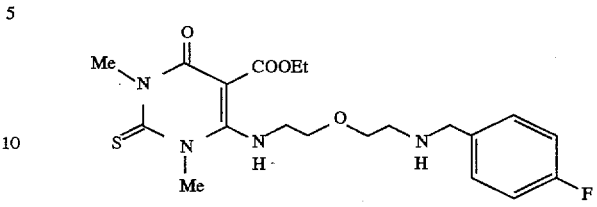

The hydrochloride of the title compound was obtained from 5-ethoxycarbonyl-1,3-dimethyl-6-methylthio-2-thioxo-2,3-dihydro-4(1H)-pyrimidinone and tert-butyl N-(p-fluorobenzyl)-N-(5-amino-3-oxapentyl)carbamate according to the same process as described in Example 58. After neutralizing the hydrochloride, extraction was carried out to give the free base as crystals. Yield=69%.
m.p. 103°–108° C.
$^1$HNMR(CDCl$_3$)δ1.33(t,J=7 Hz,3H), 2.78(t,J=5 Hz,2H), 3.46(q,J=5 Hz,2H), 3.59–3.62(m,4H), 3.70(s,3H), 3.78(s,2H), 3.80(s,13H), 4.20(q,J=7 Hz,2H), 6.97–7.03(m,2H), 7.28–7.32(m,2H), 9.61(bs,1H)
MS m/z 439(M$^+$+1)

Then, the hydrochloride of the title compound was obtained as crystals in a conventional manner.
m.p. 53°–57° C.

EXAMPLE 66

5-Cyano-6-[cis-6-[N-(p-fluorobenzyl)-N-methylaminomethyl]-2-tetrahydropyranylmethylamino]-4-imino-1,3-dimethyl-3,4-dihydro-2(1H)-pyrimidinethione

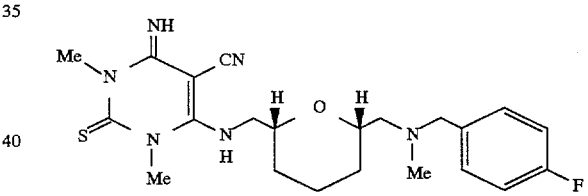

To a suspension of lithium aluminum hydride (720 mg, 19.0 mmol) in THF (7 ml) was added dropwise under ice-cooling a solution of crude cis-2-aminomethyl-6-[N-ethoxycarbonyl-N-(p-fluorobenzyl)aminomethyl]tetrahydropyrane (1.23 g, 4.62 mmol) in THF (10 ml). After stirring for 10 minutes, the mixture was heated under reflux for 1.5 hours. To the reaction mixture was added under ice-cooling aqueous ammonia (20 ml). After stirring for 2 hours, it was filtered with Celite. The filtrate was extracted with ethyl acetate (50 ml×3) and the combined organic layer was washed with a saturated aqueous solution of sodium chloride (30 ml), dried over potassium carbonate and the solvent was distilled off under reduced pressure. The residue was dissolved in acetonitrile-chloroform (5/1, 12 ml) and 5-cyano-4-imino-1,3-dimethyl-6-methylthio-3,4-dihydro-2 (1H)-pyrimidinethione (981 mg, 4.34 mmol) was added and the mixture was stirred at room temperature for 6.5 hours and then heated under reflux for 1.5 hours. The solvent was distilled off under reduced pressure and the residue was chromatographed using silica gel column to give the title compound (1.12 g) from the fraction from methanol-chloroform (3/97). Yield=55%.
$^1$HNMR(CDCl$_3$)δ1.1–1.29(m,2H), 1.51–1.66(m,2H), 1.76 (brd, J=13 Hz,1H), 1.92(brd,J=14 Hz,1H), 2.23(s,3H), 2.61

(brt,J=12 Hz,1H), 3.20(s,3H), 3.34–3.50(m,2H), 3.53–3.73 (m,3H), 3.77–4.00(m,5H), 7.03(brt,J=8 Hz,2H), 7.14–7.30 (m,2H)

Then, the hydrochloride of the title compound was obtained as crystals in a conventional manner.

m.p. 172°–178° C.

EXAMPLE 67

5-Cyano-6-[trans-6-[N-(p-fluorobenzyl)-N-methylaminomethyl]-2-tetrahydropyranylmethylamino]-4-imino-1,3-dimethyl-3,4-dihydro-2(1H)-pyrimidinethione

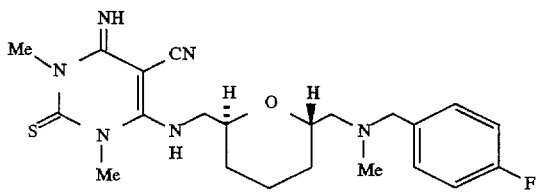

This compound was synthesized from trans-2-aminomethyl-6-[N-ethoxycarbonyl-N-(p-fluorobenzyl) aminomethyl]tetrahydropyrane according to the same process as described in Example 66. Yield=55%.

$^1$HNMR(CDCl$_3$)δ1.33–1.79(m,4H), 2.18–2.35(m,1H), 2.27 (s,3H), 2.75(dd,J=9 Hz,13 Hz,1H), 3.28–4.19(m,7H), 3.67 (s,3H), 3.93(s,3H), 6.92–7.08(m,1H), 7.00(brt,J=8 Hz,2H), 7.18–7.34(m,3H)

Then, the corresponding hydrochloride was obtained as crystals in a conventional manner.

m.p. 150°–155° C.

EXAMPLE 68

5-Cyano-6-[trans-5-[N-(p-fluorobenzyl)-N-methylaminomethyl]-2-tetrahydrofuranylmethylamino]-4-imino-1,3-dimethyl- 3,4-dihydro-2(1H)-pyrimidinethione

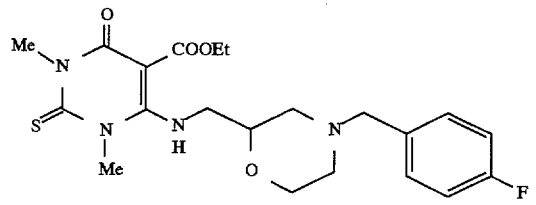

This compound was synthesized from trans-2-aminomethyl-5-[N-methoxycarbonyl-N-(p-fluorobenzyl) aminomethyl]tetrahydrofuran according to the same process as described in Example 66. Yield=83%.

$^1$HNMR(CDCl$_3$)δ1.54–1.75(brm,2H), 1.98–2.18(brm,1H), 2.28(s,3H), 2.43(dd, J=4 Hz,12.7 Hz,1H), 2.53(dd, J=7 Hz,13 Hz, 1H), 3.42–3.65(m,3H), 3.70–4.00(brm,9H), 4.18–4.30(brm,2H), 5.19–5.61(brm,1H), 7.18–7.39(m,5H)

Then, the corresponding hydrochloride was obtained as crystals in a conventional manner.

m.p. 110°–115° C.

EXAMPLE 69

5-Cyano-6-[cis-5-[N-(p-fluorobenzyl)-N-methylaminomethyl]-2-tetrahydrofuranylmethylamino]-4-imino-1,3-dimethyl-3,4-dihydro-2(1H)-pyrimidinethione

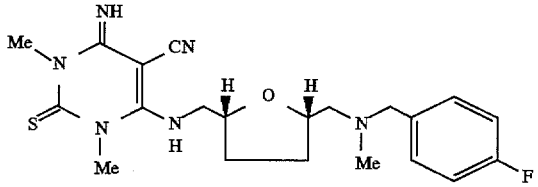

This compound was synthesized from cis-2-aminomethyl-5-[N-methoxycarbonyl-N-(p-fluorobenzyl) aminomethyl]tetrahydrofuran according to the same process as described in Example 66. Yield=27%.

$^1$HNMR(CDCl$_3$)δ1.50–1.68(m,2H), 1.92–2.18(m,2H), 2.29 (s,3H), 2.43(dd,J=5 Hz,13 Hz,1H), 2.44–2.58(m,1H), 3.38–3.62(m,3H), 3.68–4.02(m,1H), 3.77(s,3H), 3.87(s,3H), 4.08–4.17(m,1H), 5.38–5.79(br. 1H), 7.01–7.39(m,5H)

Then, the corresponding hydrochloride was obtained as crystals in a conventional manner.

m.p. 50°–55° C.

EXAMPLE 70

5-Ethoxycarbonyl-6-[4-(p-fluorobenzyl)-2-morpholinylmethylamino]-1,3-dimethyl-2-thioxo-2,3-dihydro-4(1H)-pyrimidinone

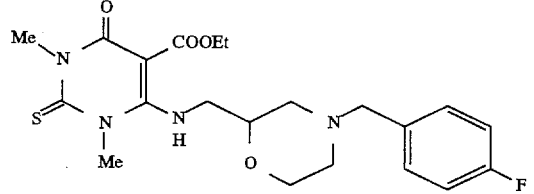

To a solution of diethyl malonate (11.2 g, 70.0 mmol) in DMF (100 ml) was added under ice-cooling sodium hydride (3.08 9, 70.0 mmol) and the mixture was stirred for 30 minutes. To the reaction mixture was added dropwise a solution (10 ml) of methyl isothiocyanate (10.2 g, 0.14 mol) in DMF and the mixture was stirred under ice-cooling for 30 minutes. Then, a solution (10 ml) of methyl iodide (9.94 g, 70.0 mmol) in DMF was added dropwise and the mixture was stirred under ice-cooling for 30 minutes and at room temperature for 2 hours. The reaction mixture was poured into water (500 ml) and extracted with ethyl acetate (500 ml ×3). The organic layer was washed with a saturated aqueous solution of sodium chloride, dried over sodium sulfate, concentrated under reduced pressure to give a yellow oil (22.46 g). To a solution of the oil (2.36 g, 8.60 mmol) in acetonitrile (15 ml) was added 2-aminomethyl-4-(p-fluorobenzyl)morpholine (1.88 g, 8.43 mmol) and the mixture was stirred at room temperature for 1.5 hours. The reaction mixture was concentrated and purified by silica gel column chromatography to give the title compound (2.33 g) as a white crystal from the fraction from hexane-ethyl acetate (2/1→0/1). Yield=61%.

m.p. 108°–109° C. (recrystallized from ethanol)

$^1$HNMR(CDCl$_3$)δ1.39(t,J=7 Hz,3H), 1.89(dd, J=10 Hz,11 Hz,1H), 2.20(ddd, J=3 Hz,10 Hz,11 Hz,1H), 2.62–2.66(m, 2H), 3.22–3.31(m,2H), 3.40(d,J=13 Hz,1H), 3.50(d,J=13 Hz,1H), 3.63–3.69(m,2H), 3.70(s,3H), 3.77(s,3H), 3.89–3.93(m,1H), 4.35(q,J=7 Hz,2H), 6.98–7.06(m,2H), 7.24–7.28(m,2H), 9.31(t,J=5 Hz,1H)

EXAMPLE 71

1,3-Diisobutyl-5-cyano-6-[4-(p-fluorobenzyl)-2-morpholinylmethylamino]-4-imino-3,4-dihydro-2(1H)-pyrimidinethione

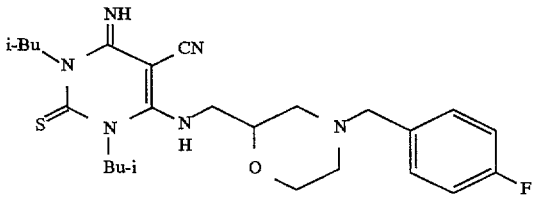

To a solution of malononitrile (1.50 g, 22.7 mmol) in DMF (30 ml) was added under ice-cooling sodium hydride (0.95 g, 23.8 mmol) and the mixture was stirred for one hour. To the reaction mixture was added dropwise isobutyl isothiocyanate (5.23 g, 45.4 mmol) and the mixture was stirred at room temperature for 1.5 hours. Then, methyl iodide (3.22 g, 22.7 mmol) was added dropwise and the mixture was stirred at room temperature for one hour. To the reaction mixture was added water (50 ml), which was then extracted with ethyl acetate (200 ml). The organic layer was dried over magnesium sulfate, concentrated under reduced pressure to give a brown crystal (5.24 g). To a solution of the crystal (1.00 g) in acetonitrile (5 ml) was added 2-aminomethyl-4-(p-fluorobenzyl)morpholine (1.00 g) and the mixture was stirred for 2.5 hours. Insolubles were filtered off, the filtrate was concentrated under reduced pressure and the residue was purified by silica gel column chromatography to give the title compound as a yellow oily substance from the fraction from hexane-ethyl acetate (1/2). Yield=16%.

$^1$HNMR(CDCl$_3$)δ0.79–0.83(m,2H), 0.92–0.98(m,12H), 1.95–2.89(m,8H), 3.42–4.61(m,7H), 6.98–7.04(m,2H), 7.31–7.25(m,2H)

MS m/z 486(M$^+$)

Then, the title compound (0.33 g) was dissolved in a mixed solvent of ethyl acetate (5 ml) and methanol (1 ml) and a 4N hydrochloric acid-ethyl acetate solution (0.5 ml) was added under ice-cooling while stirring. The reaction mixture was concentrated to give the hydrochloride as crystals (0.37 g).

m.p. 159°–162° C.

IR(KBr) 2960, 2214, 1657, 1563, 1511, 1350, 1229, 1136, 741cm$^{-1}$

EXAMPLE 72

5-Cyano-6-[4-(p-fluorobenzyl)-2-morpholinylmethylamino]-1-methyl-3-phenyl-2,4(1H,3H)-pyrimidinedione

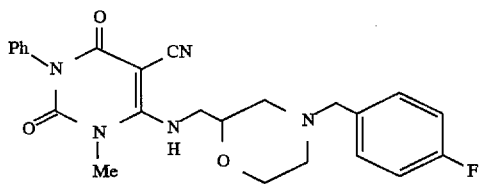

To a solution of ethyl 3-methylamino-3-methylthio-2-cyanoacrylate (1.45 g, 7.25 mmol) in toluene (20 ml) were added at room temperature while stirring triethylamine (0.2 ml) and phenyl isocyanate (1.76 g, 13.0 mmol) and the mixture was heated under reflux for 2 hours. After cooling, the solvent was distilled off and the residue was dissolved in acetonitrile (30 ml), 2-aminomethyl-4-(p-fluorobenzyl)morpholine (2.26 g, 9.82 mmol) was added and the mixture was stirred at room temperature for one hour. The reaction mixture was concentrated and the residue was purified by silica gel column chromatography to give the title compound (0.84 g) from the fraction from hexane-ethyl acetate (1/1→0/1). Yield=26%.

m.p. 96°–98° C. (recrystallized from hexane-ethyl acetate)

$^1$HNMR(CDCl$_3$)δ1.98(dd, J=10 Hz,11 Hz,1H), 2.20(dt,J=3 Hz,11 Hz, 1H), 2.69(dd, J=2 Hz,11 Hz,1H), 2.82(d,J=11 Hz,1H), 3.47(s,3H), 3.49(s,3H), 3.63–3.69(m,1H), 3.73(dd, J=2 Hz,11 Hz,1H), 3.82–3.88(m,1H), 3.91–3.95(m,1H), 4.05–4.09(m,1H), 5.86(bs,1H), 7.00–7.05(m,2H), 7.16–7.19 (m,2H), 7.26–7.29(m, 2H), 7.39–7.49(m,3H)

IR(KBr) 2210, 1719, 1656, 1574, 1562, 1421, 1218, 1119, 763cm$^{-1}$

MS m/z 449(M$^+$)

Then, the title compound (0.80 g) was dissolved in ethyl acetate (20 ml) and a 4N hydrochloric acid-ethyl acetate solution (1 ml) was added under ice-cooling while stirring. The crystal thus separated out was recovered by filtration and dried under reduced pressure to give the hydrochloride as a crystal (0.77 g).

m.p. 169°–171° C.

EXAMPLE 73

5-Cyano-6-[4-(p-fluorobenzyl)-2-morpholinylmethylamino]-4-imino-1,3-dimethyl-3,4-dihydro-2(1H)-pyrimidinone

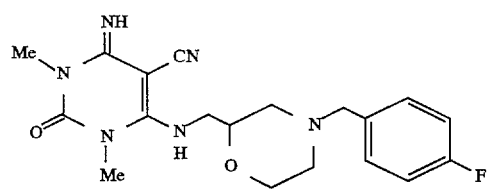

This compound was synthesized from 2-aminomethyl-4-(p-fluorobenzyl)morpholine and 2-methylamino-2-methylthio-1,1-ethylenedicarbonitrile and methyl isocyanate according to the same process as described in Example 72. Yield=59%.

m.p. 177°–178° C. (recrystallized from ethyl acetate)

$^1$HNMR(DMSO-d$_6$)δ1.76(dd, J=10 Hz,11 Hz,1H), 2.04(dt, J=3 Hz,11 Hz, 1H), 2.58(d,J=12 Hz,1H), 2.92(d,J=11 Hz,1H), 3.05(s,3H), 3.25(s,3H), 3.40–3.57(m,5H), 3.65(dd, J=5 Hz,14 Hz,1H), 3.76(d,J=11 Hz,1H), 7.09–7.14(m,2H), 7.31–7.35(m,2H), 7.49(bs,2H)

IR(KBr) 3344, 2212, 1720, 1633, 1561, 1511, 1454, 1224, 1117, 1049, 750cm$^{-1}$

MS m/z 386(M$^+$)

Then, the corresponding hydrochloride was obtained as crystals in a conventional manner.

m.p. 202°–206° C.

EXAMPLE 74

5-Cyano-6-[4-(p-fluorobenzyl)-2-morpholinylmethylamino]-3-methyl-1-phenyl-2-thioxo-2,3-dihydro-4(1H)-pyrimidinone

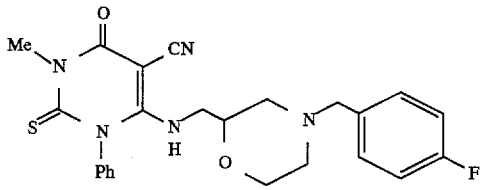

This compound was synthesized from 2-aminomethyl-4-(p-fluorobenzyl)morpholine and ethyl 3-methylthio-3-phenylamino-2-cyanoacrylate and methyl isocyanate according to the same process as described in Example 72. Yield=6%.

m.p. 63°–72° C. (a yellow foamy solid)

$^1$HNMR(CDCl$_3$)δ1.70(t,J=10 Hz,1H), 1.89(dt,J=3 Hz,11 Hz,1H), 2.51(d,J=11 Hz,1H), 2.62(d,J=11 Hz,1H), 3.84–3.44(m,3H), 3.49–8.54(m,3H), 3.72(s,3H), 3.83–3.90 (m,1H), 5.12(br, 1H), 6.98–7.02(m,2H), 7.19–7.27(m,4H), 7.55–7.63(m,3H)

IR(KBr) 8314, 2214, 1672, 1591, 1543, 1333, 1114, 754cm$^{-1}$

MS m/z 465(M$^+$)

Then, the corresponding hydrochloride was obtained as crystals in a conventional manner.

m.p. 165°–170° C.

EXAMPLE 75

5-Cyano-6-[4-(p-fluorobenzyl)-2-morpholinylmethylamino]-4-imino-1,3-dimethyl-3,4-dihydro-2(1H)-pyrimidinethione To a solution of 2-[4-(p-fluorobenzyl)-2-morpholinylmethylamino]-2-methylamino-1,1-ethylenedicarbonitrile (0.20 g, 0.61 mmol) in DMF (2 ml) was added under ice-cooling sodium hydride (24 mg, 0.61 mmol) and the mixture was stirred for one hour. To the reaction mixture was added dropwise a solution of methyl isothiocyanate (45 mg, 0.61 mmol) in DMF (0.5 ml) and stirred under ice-cooling for 3.5 hours. The reaction mixture was poured into water (20 ml) and extracted with chloroform (20 ml×3). The organic layer was washed with a saturated aqueous solution of sodium chloride, dried over sodium sulfate and concentrated under reduced pressure. The residue was purified by silica gel column chromatography to give the title compound from the fraction from ethyl acetate. Yield=81%.

EXAMPLE 76

5-Cyano-6-[4-(p-fluorobenzyl)-2-morpholinylmethylamino]-1,3-dimethyl-2-thioxo-2,3-dihydro-4(1H)-pyrimidinone To a solution of ethyl 3-[4-(p-fluorobenzyl)-2-morpholinylmethylamino]-3-methylamino-2-cyanoacrylate (1.00 g, 2.66 mmol) in DMF (10 ml) was added under ice-cooling sodium hydride (0.11 g, 2.66 mmol) and the mixture was stirred for one hour. To the reaction mixture was added dropwise a solution of methyl isothiocyanate (0.19 g, 2.66 mmol) in DMF (1 ml) and the mixture was stirred under ice-cooling for 8.5 hours. Then, the reaction mixture was poured into water (30 ml) and extracted with chloroform (50 ml×4). The organic layer was washed with a saturated aqueous solution of sodium chloride, dried over sodium sulfate, concentrated under reduced pressure. The residue was purified by silica gel column chromatography to give the title compound from the fraction from ethyl acetate. Yield=90%.

EXAMPLE 77

5-Cyano-6-[4-(p-fluorobenzyl)-2-morpholinylmethylamino]-4-imino-1-methyl-3-phenyl-3,4-dihydro-2(1H)-pyrimidinethione

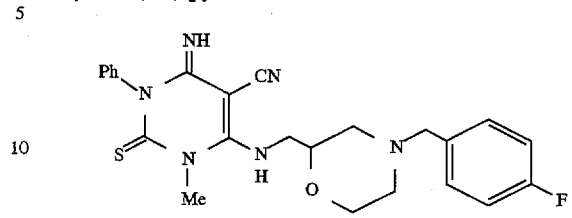

To a solution of 2-[4-(p-fluorobenzyl)-2-morpholinylmethylamino]-2-methylamino-1,1-ethylenedicarbonitrile (0.84 g, 2.55 mmol) in DMF (10 ml) was added under ice-cooling sodium hydride (0.11 g, 2.66 mmol) and the mixture was stirred for one hour. To the reaction mixture was added dropwise phenyl isothiocyanate (0.34 g, 2.55 mmol) and the mixture was stirred under ice-cooling for 2.5 hours and then at room temperature for 4.5 hours. Then, to the reaction mixture was added several drops of a saturated aqueous solution of ammonium chloride and the mixture was stirred for 5 minutes and concentrated under reduced pressure. The residue was purified by silica gel column chromatography to give the title compound as a yellow oil from the fraction from hexane-ethyl acetate (1/1). Yield=10%.

$^1$HNMR(DMSO-d$_6$)δ1.83(t,J=11 Hz,1H), 2.07–2.12(m,1H), 2.58–2.66(m,2H), 3.26–3.32(m,3H), 3.32(s,3H), 3.42(d,J= 13 Hz,1H), 3.47(d,J=13 Hz,1H), 3.52–3.59(m,1H), 3.84(d, J=11 Hz,1H), 7.07–7.19(m,5H), 7.30–7.34(m,4H)

IR(film) 3270, 2184cm$^{-1}$

EXAMPLE 78

1-Benzyl-5-cyano-6-[4-(p-fluorobenzyl)-1-piperazinyl]-4-imino-3-methyl-3,4-dihydro-2(1H)-pyrimidinethione

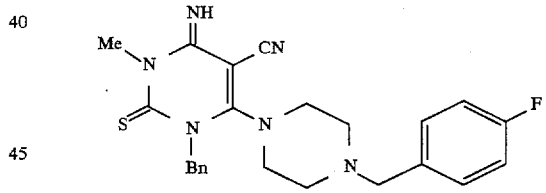

To a solution of 2-benzylamino-2-[4-(p-fluorobenzyl)-1-piperazinyl]-1,1-ethylenedicarbonitrile (0.70 g, 1.86 mmol) in acetone (5 ml) were added methyl isothiocyanate (0.41 g, 5.59 mmol) and potassium carbonate (0.25 g, 1.86 mmol) and the mixture was stirred at room temperature for 2.5 hours. Then, insolubles were filtered off and the filtrate was concentrated under reduced pressure. The residue was purified by silica gel column chromatography to give the title compound as a white crystal from the fraction from hexane-ethyl acetate (1/1). Yield=44%.

m.p. 167°–169° C. (recrystallized from ethyl acetate)

$^1$HNMR(CDCl$_3$)δ2.59(bs,4H), 3.39(bs,4H), 3.54(s,2H), 3.66(s,3H), 5.86(s,2H), 7.00–7.04(m,2H), 7.22–7.31(m,5H), 7.39(d,J=7 Hz,2H), 7.60(bs,1H)

IR(KBr) 2202, 1608, 1569, 1477, 1469, 1409, 1150, 799cm$^{-1}$

MS m/z 449(M$^+$+1)

Then, the corresponding hydrochloride was obtained as crystals in a conventional manner.

m.p. 169°–174° C.

EXAMPLE 79

5-Cyano-6-[endo-9-(p-fluorobenzyl)-9-aza-3-oxabicyclo-[3.3.1]non-7-ylamino]-1,3-dimethyl-4-methylimino-3,4-dihydro-2(1H)-pyrimidinethione

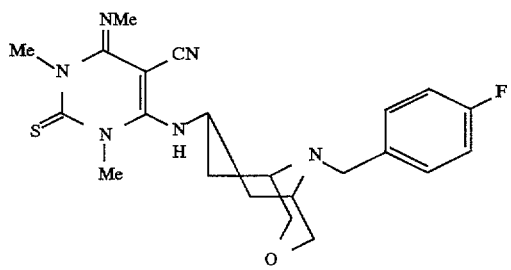

To a solution (10 ml) of 5-cyano-6-[endo-9-(p-fluorobenzyl)-9-aza-3-oxabicyclo[3.3.1]non-7-ylamino]-4-imino-1,3-dimethyl-3,4-dihydro-2(1H)-pyrimidinethione (0.35 g, 0.82 mmol) in DNF was added potassium carbonate (0.12 g, 0.87 mmol) and the mixture was stirred at room temperature for 2 hours. Then, methyl iodide ( 0.12 g, 0. 82 mmol) was added and the mixture was stirred for 2.5 hours. Insolubles were filtered off from the reaction mixture, the mother liquor was concentrated and purified by silica gel column chromatography to give the title compound (0.10 g) from the fraction from hexane-ethyl acetate (1/1) as a yellow oil. Yield=28%.

$^1$HNMR(CDCl$_3$)δ1.62(d,J=15 Hz,2H), 2.53–2.64(m,2H), 2.76(bs,2H), 3.36(s,3H), 3.71(s,3H), 3.75(s,3H), 3.79(s,2H), 3.79–3.82(m,2H), 4.01(d,J=11 Hz,2H), 4.55(bs,1H), 6.99–7.03(m,2H), 7.28–7.35(m,2H), 8.11(d,J=11 Hz,1H)

IR(film) 3238, 2910, 2188, 2060, 1709, 1639, 1215, 1107, 996, 843cm$^{-1}$

MS m/z 442(M$^+$)

Then, the corresponding hydrochloride was obtained as crystals in a conventional manner.

m.p. 162°–169° C.

EXAMPLE 80

5-Cyano-4-imino-6-[2-(3-indolyl)ethylamino]-1,3-dimethyl-3,4-dihydro-2(1H)-pyrimidinethione

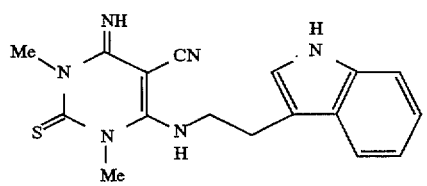

To a solution of tryptamine (500 mg, 3.12 mmol) in acetonitrile (5 ml) was added at room temperature 5-cyano-4-imino-1,3-dimethyl-6-methylthio-3,4-dihydro-2(1H)-pyrimidinethione (755 mg, 3.43 mmol) and the mixture was stirred for 5 hours. The crystal thus separated out was recovered by filtration to give the title compound (570 mg). Yield=54%.

m.p. 218°–219° C.

IR(film) 2200, 1620, 1595, 1555, 1670, 1622cm$^{-1}$ $^1$HNMR(DMSO-d$_6$)δ2.99(t,J=7 Hz,1H), 3.19(d,J=5 Hz,1H), 3.37(s,6H), 3.83(t,J=7 Hz,2H), 6.99(t,J=8 Hz,1H), 7.01(t,J=7 Hz,1H), 7.17(d,J=1 Hz,1H), 7.35(d,J=8 Hz,1H), 7.58(d,J=8 Hz,1H), 7.59–7.75(br,2H), 10.74–10.95(br, 1H)

EXAMPLE 81

5-Cyano-4-imino-1,3-dimethyl-6-isopropylamino-3,4-dihydro-2(1H)-pyrimidinethione

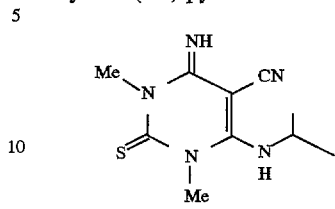

This compound was synthesized from 5-cyano-4-imino-1,3-dimethyl-6-methylthio-3,4-dihydro-2(1H)-pyrimidinethione and isopropylamine according to the same process as described in Example 80. Yield=97%.

m.p. 114°–115° C. (recrystallized from hexane-ethyl acetate)

$^1$HNMR(CDCl$_3$)δ1.19(d,J=6 Hz,6H), 3.71(s,3H), 3.72(s, 3H), 4.26(sept,J=6 Hz,1H), 5.71(bs,2H)

IR(KBr) 3320, 3226, 2964, 2198, 1640, 1574, 1493, 1410, 1316, 1102cm$^{-1}$

MS m/z 237(M$^+$)

Then, the corresponding hydrochloride was obtained as crystals in a conventional manner.

m.p. 211°–213° C.

EXAMPLE 82

5-Cyano-6-(p-fluorobenzylamino)-4-imino-1,3-dimethyl-3,4-dihydro-2(1H)-pyrimidinethione

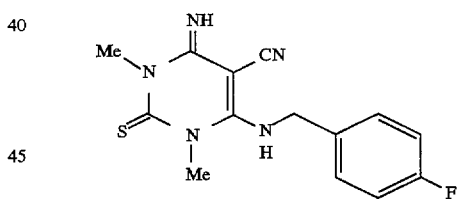

This compound was synthesized from 5-cyano-4-imino-1,3-dimethyl-6-methylthio-3,4-dihydro-2(1H)-pyrimidinethione and p-fluorobenzylamine according to the same process as described in Example 80. Yield=95%.

m.p. 202°–204° C. (recrystallized from acetonitrile)

$^1$HNMR(DMSO-d$_6$)δ3.30(s,1H), 3.71(s,3H), 3.72(s,3H), 4.75(s,2H), 7.10–7.14(m,2H), 7.36–7.40(m,2H), 7.75(bs, 1H)

IR(KBr) 3466, 3352, 2190, 1634, 1563, 1558, 1500, 1422, 1319, 1092, 811cm$^{-1}$

MS m/z 303(M$^+$)

Then, the corresponding hydrochloride was obtained as crystals in a conventional manner.

m.p. 223°–225° C.

EXAMPLE 83

6-(p-Fluorobenzyl)amino-5-cyano-1,3-dimethyl-4-benzylimino-3,4-dihydro-2(1H)-pyrimidinethione

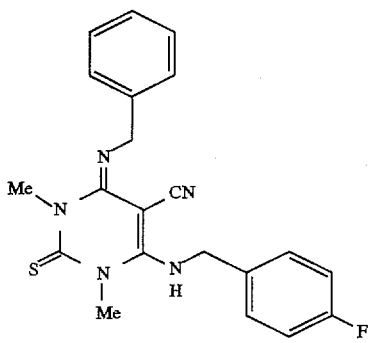

This compound was synthesized from 6-(p-fluorobenzyl)amino-5-cyano-1,3-dimethy-1,4-imino-3,4-dihydro-2(1H)-pyrimidinethione and benzyl bromide according to the same process as described in Example 79. Yield=10%.
m.p. 130°–132° C. (recrystallized from hexane-ethyl acetate)
$^1$HNMR(CDCl$_3$)δ3.75(s,3H), 3.84(s,3H), 4.64(d,J=5 Hz,2H), 4.75(s,2H), 7.00–7.14(m,2H), 7.32–7.45(m,7H)
IR(KBr) 3300, 2196, 1612, 1577, 1543, 1396, 1347, 1114, 725, 701cm$^{-1}$
MS m/z 393(M$^+$)

Then, the corresponding hydrochloride was obtained as crystals in a conventional manner.
m.p. 193°–197° C.

EXAMPLE 84

5-Cyano-4-imino-1,3-dimethyl-6-methylthio-3,4-dihydro-2(1H)-pyrimidinethione

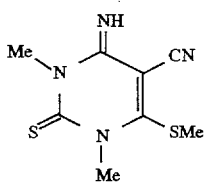

To a solution of malononitrile (11.4 g, 0.173 mol) in DMF (150 ml) was added under ice-cooling sodium hydride (7.27 g, 0.182 mol) and the mixture was stirred for 30 minutes. To the reaction mixture was added dropwise a solution (30 ml) of methyl isothiocyanate (25.2 g, 0.345 mol) in DMF and the mixture was stirred under ice-cooling for 30 minutes and then at room temperature for 90 minutes. Then, a solution (20 ml) of methyl iodide (24.5 g, 0.173 mol) in DMF was added dropwise and the mixture was stirred at room temperature for 90 minutes. The reaction mixture was poured into ice-water (600 ml) and stirred for 30 minutes in an ice bath. The crystal thus separated out was recovered by filtration and recrystallized from ethanol to give the title compound (29.8 g). Yield=76%.
m.p. 121°–122° C.
$^1$HNMR(CDCl$_3$)δ2.73(s,3H), 3.89(s,3H), 4.04(s,3H), 7.64 (bs,1H)
IR(KBr) 3300, 2218, 1607, 1353, 1074, 808cm$^{-1}$
MS m/z 226(M$^+$)
Calc'd for C$_8$H$_{10}$N$_4$S$_2$: C 42.46; H 4.45; N 24.75; S 28.34
Found: C 42.45; H 4.41; N 24.68; S 28.33

EXAMPLE 85

5-Cyano-1,3-dimethyl-6-methylthio-2-thioxo-2,3-dihydro-4(1H)-pyrimidinone

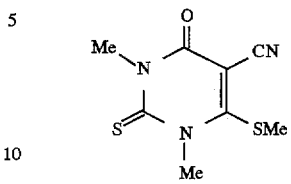

This compound was synthesized from ethyl cyanoacetate, methyl isothiocyanate and methyl iodide according to the same process as described in Example 84. Yield=40%.
m.p. 99°–100° C. (recrystallized from hexane-ethyl acetate)
$^1$HNMR(CDCl$_3$)δ2.90(s,3H), 3.73(s,3H), 4.11(s,3H)
IR(KBr) 2222, 1648, 1541, 1393, 1344, 1120, 756cm$^{-1}$
MS m/z 227 (M$^+$)

EXAMPLE 86

5-Methoxycarbonyl-3-methyl-6-methylthio-1-phenyl-2-thioxo-2,3-dihydro-4(1H)-pyrimidinone

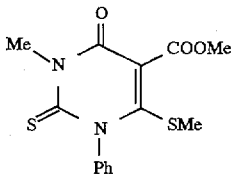

To a suspension of sodium hydride (5.0 g, 0.125 mol) in DMF (100 ml) was added dropwise under ice-cooling a solution of dimethyl melonate (15 g, 0.114 mol) in DMF (50 ml) and the mixture was stirred for 20 minutes. Then, phenyl isothiocyanate (13.6 ml, 0.114 mol) was added and stirred for 15 minutes and then methyl isothiocyanate (7.8 ml, 0.114 mol) was added and stirred for 20 minutes. To the reaction mixture was added methyl iodide (7.4 ml, 0.120 mol), the mixture was allowed to rise to room temperature and stirred for 25 minutes. To the reaction mixture was added purified water (150 ml) and extracted with ethyl acetate (150 ml×3). The combined organic layer was washed in turn with purified water (100 ml) and a saturated aqueous solution of sodium chloride (100 ml), dried over magnesium sulfate and the solvent was distilled off under reduced pressure. The residue was column-chromatographed to give 10.2 g of the title compound from the fraction from ethyl acetate-hexane (1/4) as a pale yellow oily substance. Yield=25%.
$^1$HNMR(CDCl$_3$)δ2.29(s,3H), 3.75(s,3H), 3.93(s,3H), 7.22 (d,J=6 Hz,1H), 7.23(d,J=7 Hz,1H), 7.42–7.60(m,3H)

EXAMPLE 87

5-Cyano-4-imino-3-methyl-6-methylthio-1-phenyl-3,4-dihydro-2(1H)-pyrimidinethione

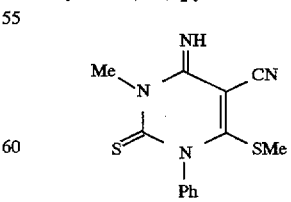

This compound was synthesized from malononitrile, phenyl isothiocyanate, methyl isothiocyanate and methyl iodide according to the same process as described in Example 86. Yield=64%.

m.p. 148°–150° C. (recrystallized from ethanol)
¹HNMR(CDCl₃)δ2.67(s,3H), 3.90(s,3H), 7.19–7.16(m,2H), 7.52–7.47(m,2H), 7.75(bs,1H)
IR(KBr) 2208, 1610, 1593, 1536, 1445, 1405, 1346, 1236, 1124, 807, 697cm⁻¹
MS m/z 288(M⁺)

EXAMPLE 88

3-Methyl-6-methylthio-1-phenyl-5-(2-propoxycarbonyl)-2-thioxo-2,3-dihydro-4(1H)-pyrimidinone

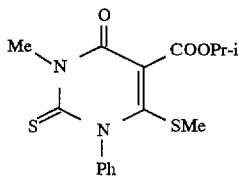

This compound was synthesized from diisopropyl malonate, phenyl isothiocyanate, methyl isothiocyanate and methyl iodide according to the same process as described in Example 86. Yield=35%.
¹HNMR(CDCl₃)δ1.39(d,J=6 Hz,6H), 2.30(s,3H), 3.75(s,3H), 5.21–5.32(m,1H), 7.24–7.60(m,2H), 7.45–7.59(m,3H)
IR(KBr) 1735, 1665, 1388cm⁻¹

EXAMPLE 89

5-Benzyloxycarbonyl-3-methyl-6-methylthio-1-phenyl-2-thioxo-2,3-dihydro-4(1H)-pyrimidinone

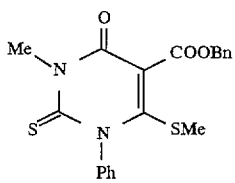

This compound was synthesized from dibenzyl melonate, phenyl isothiocyanate, methyl isothiocyanate and methyl iodide according to the same process as described in Example 86. Yield=35%.
¹HNMR(CDCl₃)δ2.12(s,3H), 3.74(s,3H), 5.36(s,2H), 7.19–7.55(m,10H)

EXAMPLE 90

5-n-Butoxycarbonyl-3-methyl-6-methylthio-1-phenyl-2-thioxo-2,3-dihydro-4(1H)-pyrimidinone

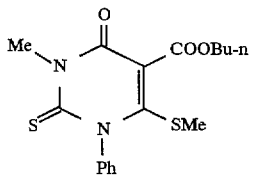

This compound was synthesized from di-n-butyl melonate, phenyl isothiocyanate, methyl isothiocyanate and methyl iodide according to the same process as described in Example 86. Yield=44%.
¹HNMR(CDCl₃)δ0.96(t,J=7 Hz,3H), 1.37(m,2H), 1.38–1.79(m,2H), 2.12(s,3H), 3.75(s,3H), 4.32(t,J=7 Hz,2H), 7.15–7.29(m,3H), 7.42–7.58(m,2H)

EXAMPLE 91

5-Cyclohexyloxycarbonyl-3-methyl-6-methylthio-1-phenyl-2-thioxo-2,3-dihydro-4(1H)-pyrimidinone

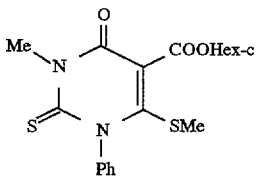

This compound was synthesized from dicyclohexyl malonate, phenyl isothiocyanate, methyl isothiocyanate and methyl iodide according to the same process as described in Example 86. Yield=7%.
¹HNMR(CDCl₃)δ1.17–1.65(m,6H), 1.66–1.85(m,2H), 1.90–2.05(m,2H), 2.61(s,3H), 3.75(s,3H), 4.79–4.88(m,1H), 7.08–7.30(m,2H), 7.39–7.58(m,3H)

EXAMPLE 92

5-Cyano-1,3-dimethyl-6-methylthio-2,4(1H,3H)-pyrimidinedione

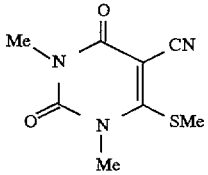

a) Ethyl 2-cyano-3-methylamino-3-methylthioacrylate

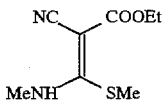

To a suspension of sodium hydride (3.90 g, 97.2 mmol) in DMF (100 ml) was added under ice-cooling ethyl cyanoacetate (4.7 ml, 44.2 mmol) and after stirring for 10 minutes methyl isothiocyanate (3.3 ml, 48.6 mmol) was added and the mixture was stirred for 30 minutes. Then, methyl iodide (6.1 ml, 97.2 mmol) was added and the mixture was stirred for one hour. To the reaction mixture was added water (100 ml) and extracted with chloroform (100 ml×3). The organic layer was dried over magnesium sulfate, and concentrated under reduced pressure. The residue was purified by silica gel column chromatography to give the title compound (9.13 g) from the fraction from hexane-ethyl acetate (2/1). Yield=98%.
m.p. 87°–88° C. (recrystallized from hexane-ethyl acetate)
¹HNMR(CDCl₃)δ1.32(t,J=7 Hz,3H), 2.68(s,3H), 3.20(d,J=5 Hz,3H), 4.21(q,J=7 Hz,2H), 10.00(bs,1H)
IR(KBr) 2200, 1656, 1587, 1382, 1266, 1031, 775cm⁻¹
MS m/z 200(M⁺)

b) 5-Cyano-1,3-dimethyl-6-methylthio-2,4(1H,3H)-pyrimidinedione

To a solution of ethyl 2-cyano-3-methylamino-3-methylthioacrylate (1.30 g, 6.50 mmol) in toluene (10 ml) were added triethylamine (0.66 g, 6.50 mmol) and methyl isocyanate (3.70 g, 65.0 mmol) and the mixture was heated under reflux for 3 hours. The reaction mixture was concentrated and the residue was recrystallized from hexane-ethyl acetate to give the title compound (0.91 g) as a white crystal. Yield=66%.

m.p. 118°–120° C.
¹HNMR(CDCl₃)δ2.91(s,3H), 3.37(s,3H), 3.66(s,3H)
IR(KBr) 2222, 1721, 1655, 1541, 1432, 1064, 764cm⁻¹
MS m/z 211(M⁺)

EXAMPLE 93
5-Cyano-3-methyl-6-methylthio-1-phenyl-2,4(1H,3H)-pyrimidinedione

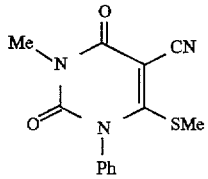

a) Ethyl 2-cyano-3-methylthio-3-phenylaminoacrylate

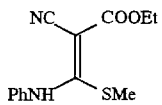

This compound was synthesized from ethyl cyanoacetate, phenyl isothiocyanate and methyl iodide according to the same process as described in Example 92a. Yield=68%.
m.p. 70°–71° C. (recrystallized from hexane-ethyl acetate)
¹HNMR(CDCl₃)δ1.35(t,J=7 Hz,3H), 2.23(s,3H), 4.26(q,J=7 Hz,2H), 7.29–7.32(m,3H), 7.38–7.43(m,2H), 11.51(bs,1H)
IR(KBr) 2204, 1656, 1561, 1377, 1265, 1027, 767cm⁻¹
MS m/z 263(M⁺)

b) 5-Cyano-3-methyl-6-methylthio-1-phenyl-2,4(1H,3H)-pyrimidinedione

This compound was synthesized from ethyl 2-cyano-3-methylthio-3-phenylaminoacrylate and methyl isocyanate according to the same process as described in Example 92b. Yield=27%.
m.p. 217°–219° C. (recrystallized from hexane-ethyl acetate)
¹HNMR(CDCl₃) δ2.76(s,3H), 3.40(s,3H), 7.26–7.23(m,2H), 7.56–7.53(m,3H)
IR(KBr) 2226, 1735, 1658, 1552, 1438, 1387, 1340, 764, 731cm⁻¹
MS m/z 273(M⁺)

EXAMPLE 94
1-(5-Cyano-3-methyl-6-methylthio-1-phenyl-2-thioxo-1,2,3,4-tetrahydropyrimidin-4-ylidene)-3-phenylurea

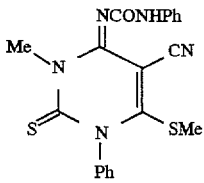

To a suspension of 5-cyano-4-imino-3-methyl-6-methylthio-1-phenyl-3,4-dihydro-2(1H)-pyrimidinethione (5.0 g) in toluene (50 ml) were added phenyl isocyanate (2.8 ml) and triethylamine (0.2 ml) and the mixture was heated under reflux for 3 hours. After the solvent was distilled off under reduced pressure, the residue was crystallized in diethyl ether. The crystal was recovered by filtration, dried under reduced pressure to give the title compound (5.9 g). Yield=84%.

¹HNMR(CDCl₃)δ2.75(s,3H), 3.88(s,3H), 7.08–7.60(m,10H)
MS m/z 405(M⁺)

EXAMPLE 95
1-(5-Cyano-1,3-dimethyl-6-methylthio-2-thioxo-1,2,3,4-tetrahydropyrimidin-4-ylidene)-3-phenylurea

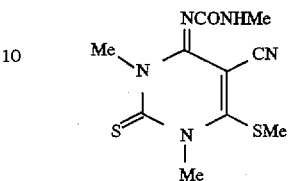

This compound was synthesized from 5-cyano-4-imino-1,3-dimethyl-6-methylthio-3,4-dihydro-2(1H)-pyrimidinethione and methyl isocyanate (14 ml) according to the same process as described in Example 94. Yield=12%.
¹HNMR(CDCl₃)δ2.81(s,3H), 2.93(d,J=5 Hz, 3H), 3.79(s, 3H), 4.06(s,3H), 5.22–5.24(brm,1H)
MS m/z 283(M⁺)

EXAMPLE 96
1-(5-Cyano-1,3-dimethyl-6-methylthio-2-thioxo-1,2,3,4-tetrahydropyrimidin-4-ylidene)-3-phenylurea

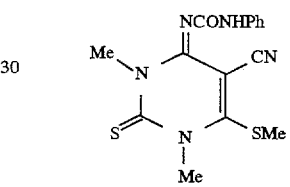

This compound was synthesized from 5-cyano-4-imino-1,3-dimethyl-6-methylthio-3,4-dihydro-2(1H)-pyrimidinethione and phenyl isocyanate according to the same process as described in Example 94. Yield=47%.
¹HNMR(DMSO-d₆)δ2.70(s,3H), 3.76(s,3H), 3.99(s,3H), 6.99(t,J=7 Hz,1H), 7.27(t,J=8 Hz, 1H), 7.57(d,J=8 Hz,2H), 9.63(s,1H)
¹³CNMR(DMSO-d₆)δ18.84, 38.73, 43.73, 91.93, 113.62, 118.96, 122.45, 128.45, 139.48, 145.53, 156.89, 161.85, 176.70
MS m/z 345(M⁺)

EXAMPLE 97
1-(5-Cyano-3-methyl-6-methylthio-1-phenyl-2-thioxo-1,2,3,4-tetrahydropyrimidin-4-ylidene)-3-isopropylurea

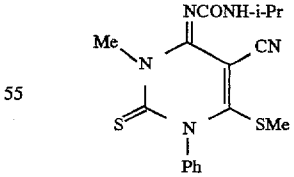

This compound was synthesized from 5-cyano-4-imino-3-methyl-6-methylthio-1-phenyl-3,4-dihydro-2(1H)-pyrimidinethione and isopropyl isocyanate according to the same process as described in Example 94. Yield=19%.
¹HNMR(CDCl₃)δ1.14(d,J=6 Hz,6H), 2.72(s,3H), 3.82(s, 3H), 5.17(brd,J=7 Hz,1H), 7.14–7.17(m,2H), 7.50–7.53(m, 3H)
MS m/z 373(M⁺)

EXAMPLE 98
4-Acetylimino-5-cyano-3-methyl-6-methylthio-1-phenyl-3,4-dihydro-2(1H)-pyrimidinethione

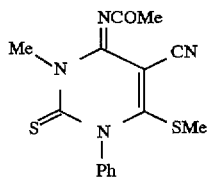

To a suspension of 5-cyano-3-methyl-4-imino-6-methylthio-1-phenyl-3,4-dihydro-2(1H)-pyrimidinethione (5.0 g) in toluene (50 ml) were added acetic anhydride (1.6 ml), pyridine (1.4 ml) and dimethylaminopyridine (0.2 g) and the mixture was heated under reflux for 12 hours. The solvent was distilled off under reduced pressure and the residue thus obtained was silica gel-chromatographed to give 1.2 g of the title compound from the fraction from hexane-ethyl acetate. Yield=21%.
$^1$HNMR(CDCl$_3$)δ2.38(s,3H), 2.71(s,3H), 3.80(s,3H), 7.13–7.16(m,2H), 7.51–7.54(m,3H)
MS m/z 330(M$^+$), 315

EXAMPLE 99
1-(5-Cyano-6-methylthio-2-oxo-1,3-diphenyl-1,2,3,4-tetrahydropyrimidin-4-ylidene)-3-phenylurea

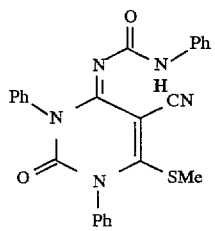

a) 2-phenylamino-2-methylthio-1,1-ethylenecarbonitrile

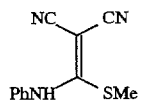

This compound was synthesized from malononitrile, phenyl isothiocyanate and methyl iodide according to the same process as described in Example 92a. Yield=66%.
m.p. 170°–176° C. (recrystallized from ethanol)
$^1$HNMR(CDCl$_3$)δ2.29(s,3H), 7.26–7.29(m,2H), 7.31–7.36 (m,1H), 7.41–7.46(m,2H), 7.86(bs,1H)
IR(KBr) 3292, 2208, 2198, 2184, 1597, 1526, 1494, 1451, 1265, 968, 761, 701cm$^{-1}$
MS m/z 215(M$^+$)
b) 1-(5-Cyano-6-methylthio-2-oxo-1,3-diphenyl-1,2,3,4-tetrahydropyrimidin-4-ylidene)-3-phenylurea To a suspension of 2-phenylamino-2-methylthio-1,1-ethylenedicarbonitrile (0.56 g, 2.32 mmol) in toluene (20 ml) were added phenyl isocyanate (0.31 g, 2.32 mmol) and triethylamine (0.05 ml) and the mixture was heated under reflux for 15 minutes. The reaction mixture was concentrated and the residue was purified by silica gel column chromatography to give the title compound (0.36 g) as a white crystal from the fraction from hexane-ethyl acetate (1/1). Yield=34%.
$^1$HNMR(CDCl$_3$)δ2.76(s,3H), 6.84(bs,1H), 7.02–7.06(m,1H), 7.26–7.53(m,14H)
IR(KBr) 2216, 1733, 1625, 1526, 1402, 755, 691cm$^{-1}$

EXAMPLE 100
1-(5-Cyano-1-methyl-6-methylthio-2-oxo-3-phenyl-1,2,3,4-tetrahydropyrimidin-4-ylidene)-3-phenylurea

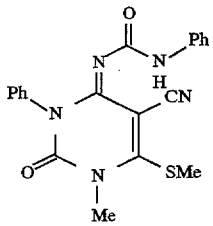

a) 2-Methylamino-2-methylthio-1,1-ethylenecarbonitrile

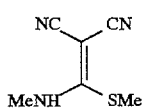

This compound was synthesized from malononitrile, methyl isothiocyanate and methyl iodide according to the same process as described in Example 92a. Yield=43%.
m.p. 118°–121° C. (recrystallized from hexane-ethyl acetate)
$^1$HNMR(CDCl$_3$)δ2.68(s,3H), 3.22(d,J=5 Hz,3H), 6.28(bs, 1H)
IR(KBr) 3318, 2208, 2186, 1548, 1403, 1285cm$^{-1}$
MS m/z 153(M$^+$)
b) 1-[5-Cyano-1-methyl-6-methylthio-2-oxo-3-phenyl-1,2,3,4-tetrahydropyrimidin-4-ylidene]-3-phenylurea This compound was synthesized from 2-methylamino-2-methylthio-1,1-ethylenedicarbonitrile and methyl isocyanate according to the same process as described in Example 99b. Yield=32%.
$^1$HNMR(CDCl$_3$)δ2.76(s,3H), 3.34(s,3H), 6.93(t,J=7 Hz,1H), 7.18–7.22(m,2H), 7.27–7.29(m,2H), 7.36–7.48(m, 5H), 9.23(bs,1H)
IR(KBr) 3400, 2360, 2222, 1722, 1666, 1586, 1508, 1418, 1315, 1070cm$^{-1}$

EXAMPLE 101
5-Cyano-6-[4-(p-fluorobenzyl)-3-morpholinylmethylamino]-4-imino-1,3-dimethyl-3,4-dihydro-2(1H)-pyrimidinethione

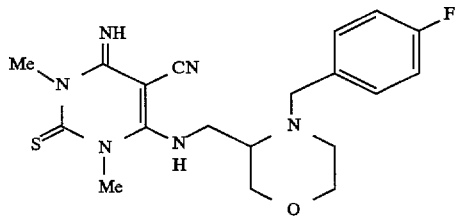

This compound was synthesized from 5-cyano-1,3-dimethyl-4-imino-6-methylthio-3,4-dihydro-2(1H)-pyrimidinethione and 3-aminomethyl-4-(p-fluorobenzyl) morpholine according to the same process as described in Example 1. Yield=79%.
$^1$HNMR(CDCl$_3$)δ2.25–2.90(m,3H), 3.30–4.10(m,14H), 5.15–5.25(br,1H), 6.25–6.32(br,1H), 6.87–7.36(m,4H)
Then, the hydrochloride of the compound was obtained as crystals in a conventional manner.

EXAMPLE 102

Acetylcholine-release accelerating action of the present compounds in gastrointestinal tract was investigated according to the following procedure. That is to say, a longitudinal muscle sample (including myenteric plexus) was prepared from the ileum excised from guinea pig and suspended in Magnus' tube. This sample was perfused in a physiological salt solution and stimulated by the electric current via platinum electrodes. Acetylcholine was released from the myenteric plexus of the sample by this stimulation and the longitudinal muscle was observed to contract. This contraction was isometrically recorded. Accordingly, the drug capable of accelerating the release of acetylcholine could enhance the contraction caused by electric stimulation only. Evaluation of the compounds was represented in terms of increase ratio in contraction by electrical stimulation.

| Example No. | Contraction increase ratio (%) $10^{-7}$M | $10^{-5}$M |
|---|---|---|
| 1 | 15.6 | Base line raised |
| 3 | 2.1 | |
| 6 | 17.0 | Base line raised |
| 7 | 20.4 | |
| 8 | 8.1 | |
| 9 | 6.9 | |
| 10 | 2.5 | |
| 11 | 0.2 | 2.9 |
| 13 | 6.3 | |
| 15 | 11.3 | |
| 16 | 5.7 | |
| 17 | 6.4 | 11.5 |
| 18 | 7.6 | |
| 19 | 9.6 | |
| 20 | 5.1 | |
| 21 | 8.0 | |
| 22 | 19.0 | Base line raised |
| 23 | 16.3 | 92.0 |
| 24 | 14.7 | 23.2 |
| 25 | 8.3 | |
| 26 | 26.9 | 48.6 |
| 27 | 5.1 | |
| 28 | 12.8 | 48.4 |
| 29 | 7.4 | |
| 30 | 5.9 | 50.7 |
| 31 | 11.2 | |
| 32 | 2.3 | 12.4 |
| 33 | 38.4 | |
| 34 | 27.7 | 70.9 |
| 35 | 10.2 | 80.1 |
| 36 | 30.3 | 35.0 |
| 37 | 6.2 | 30.4 |
| 38 | 13.2 | 115.3 |
| 39 | 2.6 | 59.6 (Base line raised) |
| 40 | 1.1 | 38.7 |
| 41 | 4.7 | |
| 42 | 1.5 | 54.0 (Base line raised) |
| 43 | 5.0 | 17.2 (Base line raised) |
| 44 | 8.1 | |
| 45 | 3.8 | |
| 46 | 3.4 | |
| 47 | 12.5 | 79.6 |
| 48 | 5.0 | 77.8 |
| 49 | 3.0 | |
| 51 | 1.1 | |
| 52 | 4.1 | 26.8 |
| 53 | 0.9 | 18.5 |
| 54 | | 6.6 |
| 55 | | 86.9 |
| 56 | 13.9 | 12.5 |
| 57 | 14.0 | Base line raised |
| 58 | | 12.6 |

-continued

| Example No. | Contraction increase ratio (%) $10^{-7}$M | $10^{-5}$M |
|---|---|---|
| 59 | 9.7 | 79.5 |
| 60 | | 46.2 |
| 61 | 2.3 | 73.8 |
| 62 | 3.3 | 71.6 |
| 63 | 4.7 | 40.1 |
| 64 | 19.0 | 130.1 |
| 65 | 2.6 | 13.3 |
| 67 | 2.6 | |
| 70 | 5.9 | |
| 71 | 5.9 | 7.9 |
| 72 | 6.8 | |
| 73 | 6.0 | |
| 74 | 4.8 | |
| 77 | 4.3 | |
| 79 | 3.4 | 8.4 |
| 80 | 18.5 | |
| 81 | 0.9 | |
| 82 | 13.3 | 77.4 |
| 83 | 4.6 | 8.6 |
| 84 | 4.4 | |
| 85 | 5.3 | 7.8 |

Finally, illustrative examples of a pharmaceutical composition which comprises as an active ingredient the present compound are Given below by way of the following Examples.

EXAMPLE 103

(Formulation Example 1)

| Tablets (one tablet) | |
|---|---|
| The compound of Example 33 | 1 mg |
| Lactose | 70 mg |
| Crystalline cellulose | 20 mg |
| Corn starch | 8 mg |
| Magnesium stearate | 1 mg |
| Total | 100 mg |

All components were uniformly mixed to form a powder for direct compression. This powder was formed to a tablet having a diameter of 6 mm and a weight of 100 mg.

(Formulation Example 2)

| Granules (one package) | |
|---|---|
| A: The compound of Example 34 | 1 mg |
| Lactose | 99 mg |
| Corn starch | 50 mg |
| Crystalline cellulose | 50 mg |
| B: Hydroxypropylcellulose | 10 mg |
| Ethanol | 9 mg |

After all components of the above group A were uniformly mixed, the solution of the above group B was added. The mixture was kneaded, graded by an extrusion granulation method and then dried in a drier at 50° C. The granules as dried up were sieved to a grain size of 297 μm–1460 μm to form granules. One package comprised 200 mg.

(Formulation Example 3)

| Syrups | |
|---|---|
| The compound of Example 1 | 0.100 g |
| Sucrose | 30.000 g |
| D-Sorbitol 70 w/v % | 25.900 g |
| Ethyl para-hydroxybenzoate | 0.030 g |
| Propyl para-hydroxybenzoate | 0.015 g |
| Flavors | 0.200 g |
| Glycerol | 0.150 g |
| 96% Ethanol | 0.500 g |
| Distilled water | any proper amount to make up a total amount to 100 ml |

The sucrose, D-sorbitol, ethyl-parahydroxybenzoate, propyl para-hydroxybenzoate and the compound of Example 1 were dissolved in 60 g of hot water. After cooling, a solution of the flavors in glycerol and ethanol was added. Then, the water was added to the resulting mixture to make up to a 100 ml volume.

Industrial Applicability

The pyrimidine derivatives (I) or pharmacologically acceptable salts thereof as provided by the present invention can be applied for the therapy of digestive tract disorders derived from chronic gastritis, diabetes mellitus, post-gastrectomy and peptic ulcer and digestive tract diseases including reflux esophagitis, irritable bowel syndrome and spurious ileus and are useful as a gastrointestinal prokinetic agent.

We claim:

1. A compound represented by the formula (I)

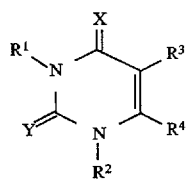

wherein:

X is O or $NR^5$, wherein $R^5$ is hydrogen, $C_1$–$C_6$ alkyl, $C_1$–$C_6$ alkylcarbonyl, phenyl group, phenyl $C_1$–$C_6$ alkyl, phenylaminocarbonyl, phenyl $C_1$–$C_4$ alkylaminocarbonyl, or $C_1$–$C_6$ alkylaminocarbonyl;

Y is S;

$R^1$ and $R^2$ are each independently the same or different and each is hydrogen, $C_1$–$C_6$ alkyl, $C_3$–$C_6$ cycloalkyl, phenyl, naphthyl, $C_3$–$C_6$ cycloalkyl $C_1$–$C_4$ alkyl, or phenyl $C_1$–$C_4$ alkyl;

$R^3$ is CN or $COOR^6$, wherein $R^6$ is $C_1$–$C_6$ alkyl, $C_3$–$C_6$ cycloalkyl, phenyl, or phenyl $C_1$–$C_4$ alkyl;

$R^4$ is —$NR^8R^9$;

$R^8$ is $C_1$–$C_4$ alkyl, phenyl $C_1$–$C_4$ alkyl, naphthyl $C_1$–$C_4$ alkyl, pyridyl $C_1$–$C_4$ alkyl, phenoxy $C_2$–$C_6$ alkyl, 1H-indol-3-yl $C_1$–$C_4$ alkyl, in which the phenyl, phenoxy, naphthyl and 1H-indol-3-yl moieties are unsubstituted or mono- to tri-substituted with halogen, $C_1$–$C_6$ alkyl, halo $C_1$–$C_6$ alkyl, $C_1$–$C_6$ alkoxy, $C_1$–$C_6$ alkoxycarbonyl or phenyl, or $R^8$ represents a group of a formulae (II)–(IX):

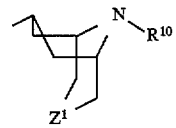

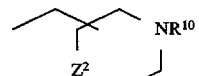

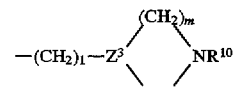

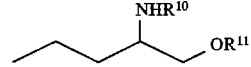

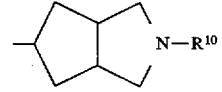

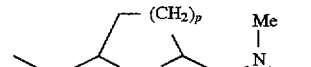

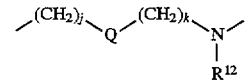

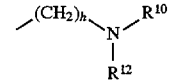

wherein $R^{10}$ is $C_1$–$C_6$ alkyl, phenyl $C_1$–$C_4$ alkyl, naphthyl $C_1$–$C_4$ alkyl, pyridyl $C_1$–$C_4$ alkyl, phenoxy $C_2$–$C_6$ alkyl, pyrrolidinylcarbonyl $C_1$–$C_4$ alkyl, in which the phenyl, phenoxy and naphthyl moieties are unsubstituted or mono- to tri-substituted with halogen, $C_1$–$C_6$ alkyl, halo $C_1$–$C_6$ alkyl, $C_1$–$C_6$ alkoxy, $C_1$–$C_6$ alkoxycarbonyl or phenyl; $R^{11}$ is hydrogen, $C_1$–$C_6$ alkyl, phenyl $C_1$–$C_4$ alkyl, phenyl or naphthyl; $Z^1$ is O, S, N($C_1$–$C_6$ alkyl) or $CH_2$; $Z^2$ is O, N($C_1$–$C_6$ alkyl) or $CH_2$; $Z^3$ is N or CH; l is 0–2; n is 4, when m is 0; n is 1 or 3, when m is 1; and n is 2, when m is 2; p is 1–2; j is 0–3; k is 0–3; a sum of j and k is 1–6; h is 1–6; Q is O, $NR^{13}$, $CHOR^{14}$ or $OCH_2CH_2O$; $R^{12}$ and $R^{13}$ is each independently the same or different and is hydrogen, $C_1$–$C_6$ alkyl or $C_1$–$C_4$ alkoxy $C_2$–$C_4$ alkyl; $R^{14}$ is hydrogen or $C_1$–$C_6$ alkyl; $R^9$ is hydrogen, $C_1$–$C_6$ alkyl or $C_1$–$C_6$ alkoxy $C_2$–$C_6$ alkyl;

or a pharmacologically acceptable salt thereof.

2. A compound having the formula (I):

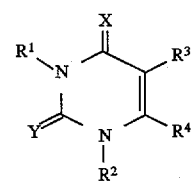

wherein

X is O or $NR^5$, wherein $R^5$ is hydrogen atom, $C_1$–$C_6$ alkyl, $C_1$–$C_6$ alkylcarbonyl, phenyl, phenyl $C_1$–$C_6$ alkyl, phenylaminocarbonyl, phenyl $C_1$–$C_4$ alkylaminocarbonyl, or $C_1$–$C_6$ alkylaminocarbonyl;

Y is S;

$R^1$ and $R^2$ are the same or different and each is hydrogen, $C_1$–$C_6$ alkyl, $C_3$–$C_6$ cycloalkyl, phenyl, naphthyl, $C_3$–$C_6$ cycloalkyl $C_1$–$C_4$ alkyl, or phenyl $C_1$–$C_4$ alkyl;

$R^3$ is CN or COOR$^6$, wherein $R^6$ is $C_1$–$C_6$ alkyl, $C_3$–$C_6$ cycloalkyl, phenyl, or phenyl $C_1$–$C_4$ alkyl;

$R^4$ is —NR$^8$R$^9$;

$R^8$ and $R^9$ represent, together with the nitrogen atom to which they are attached, an N-substituted piperazine ring of the formula (X):

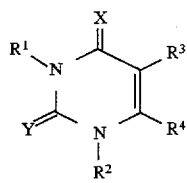

(X)

wherein $R^{10}$ is $C_1$–$C_6$ alkyl, phenyl $C_1$–$C_4$ alkyl, naphthyl $C_1$–$C_4$ alkyl, pyridyl $C_1$–$C_4$ alkyl, phenoxy $C_2$–$C_6$ alkyl, pyrrolidinylcarbonyl $C_1$–$C_4$ alkyl, in which the phenyl, phenoxy and naphthyl moieties are unsubstituted or mono- to tri-substituted with a halogen atom, $C_1$–$C_6$ alkyl group, halo $C_1$–$C_6$ alkyl, $C_1$–$C_6$ alkoxy, $C_1$–$C_6$ alkoxycarbonyl or phenyl; or a pharmacologically acceptable salt thereof.

3. A compound having the formula (I)

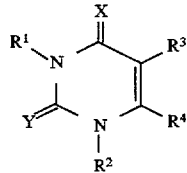

(I)

wherein

X is O or NR$^5$, wherein $R^5$ is hydrogen, $C_1$–$C_6$ alkyl, $C_1$–$C_6$ alkylcarbonyl, phenyl, phenyl $C_1$–$C_6$ alkyl, phenylaminocarbonyl, phenyl $C_1$–$C_4$ alkylaminocarbonyl, or $C_1$–$C_6$ alkylaminocarbonyl;

Y is S;

$R^1$ and $R^2$ are the same or different and each is hydrogen, $C_1$–$C_6$ alkyl, $C_3$–$C_6$ cycloalkyl, phenyl, naphthyl, $C_3$–$C_6$ cycloalkyl, $C_1$–$C_4$ alkyl, or phenyl $C_1$–$C_4$ alkyl;

$R^3$ is CN or COOR$^6$, wherein $R^6$ is $C_1$–$C_6$ alkyl, $C_3$–$C_6$ cycloalkyl, phenyl group, or phenyl $C_1$–$C_4$ alkyl;

$R^4$ is —SR$^7$, wherein $R^7$ is a $C_1$–$C_6$ alkyl;

or a pharmacologically acceptable salt thereof.

4. A compound having the formula (I):

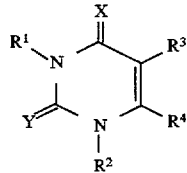

(I)

wherein

X is O or NR$^5$, wherein $R^5$ is hydrogen, $C_1$–$C_6$ alkyl, $C_1$–$C_6$ alkyl carbonyl, phenyl, phenyl $C_1$–$C_6$ alkyl, phenylamino carbonyl, a phenyl $C_1$–$C_4$ alkylamino carbonyl or $C_1$–$C_6$ alkylamino carbonyl;

Y is O;

$R^1$ and $R^2$ are the same or different and each is hydrogen, $C_1$–$C_6$ alkyl, $C_3$–$C_6$ cycloalkyl, phenyl, naphthyl, $C_3$–$C_6$ cycloalkyl $C_1$–$C_4$ alkyl, or phenyl $C_1$–$C_4$ alkyl;

$R^3$ is CN or COOR$^6$, wherein $R^6$ is $C_1$–$C_6$ alkyl, $C_3$–$C_6$ cycloakyl, phenyl, or phenyl $C_1$–$C_4$ alkyl;

$R^4$ is —NR$^8$R$^9$, $R^8$ represents a group of the formulae (II)–(IX):

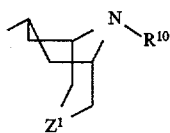

(II)

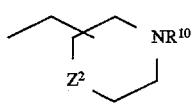

(III)

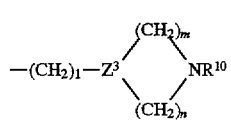

(IV)

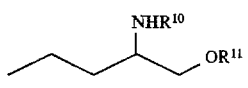

(V)

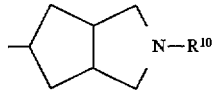

(VI)

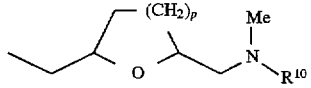

(VII)

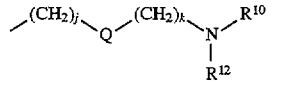

(VIII)

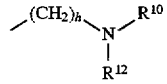

(IX)

wherein $R^{10}$ is $C_1$–$C_6$ alkyl, phenyl $C_1$–$C_4$ alkyl, naphthyl $C_1$–$C_4$ alkyl, pyridyl $C_1$–$C_4$ alkyl, phenoxy $C_2$–$C_6$ alkyl, pyrrolidinylcarbonyl $C_1$–$C_4$ alkyl, in which the phenyl, phenoxy and naphthyl moieties are unsubstituted or mono- to tri-substituted with halogen, $C_1$–$C_6$ alkyl, halo $C_1$–$C_6$ alkyl, $C_1$–$C_6$ alkoxy, $C_1$–$C_6$ alkoxycarbonyl or phenyl; $R^{11}$ is hydrogen, $C_1$–$C_6$ alkyl, phenyl $C_1$–$C_4$ alkyl, phenyl or naphthyl; $Z^1$ is O, S, N($C_1$–$C_6$ alkyl) or CH$_2$; $Z^2$ is O, N($C_1$–$C_6$ alkyl) or CH$_2$; $Z^3$ is N or CH; l is 0–2; n is 4, when m is 0; n is 1 or 3, when m is 1; and n is 2, when m is 2; p is 1–2; j is 0–3; k is 0–3; a sum of j and k is 1–6; h is 1–6; Q is O, NR$^{15}$, CHOR$^{14}$ or OCH$_2$CH$_2$O; $R^{12}$ and $R^{13}$ are the same or different and each is hydrogen, $C_1$–$C_6$ alkyl or a $C_1$–$C_4$ alkoxy $C_2$–$C_4$ alkyl; $R^{14}$ is hydrogen or $C_1$–$C_6$ alkyl; $R^9$ is hydrogen, $C_1$–$C_6$ alkyl or $C_1$–$C_6$ alkoxy $C_2$–$C_6$ alkyl;

or a pharmacologically acceptable salt thereof.

5. A compound having the formula (I):

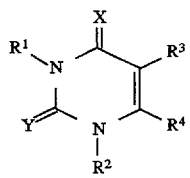

(I)

wherein

X is O or NR$^5$, wherein $R^5$ is hydrogen, $C_1$–$C_6$ alkyl, $C_1$–$C_6$ alkylcarbonyl, phenyl, phenyl $C_1$–$C_6$ alkyl, phenylaminocarbonyl, phenyl $C_1$–$C_4$ alkylaminocarbonyl, or $C_1$–$C_6$ alkylaminocarbonyl;

Y is O;

$R^1$ and $R^2$ are the same or different and each is hydrogen, $C_1$–$C_6$ alkyl, $C_3$–$C_6$ cycloalkyl, phenyl, naphthyl, $C_3$–$C_6$ cycloalkyl $C_1$–$C_4$ alkyl, or phenyl, $C_1$–$C_4$ alkyl;

$R^3$ is CN or $COOR^6$, wherein $R^6$ is $C_1$–$C_6$ alkyl, $C_3$–$C_6$ cycloalkyl $C_1$–$C_4$ alkyl, or phenyl $C_1$–$C_4$ alkyl;

$R^4$ is —$NR^8R^9$;

$R^8$ and $R^9$ represent, together with the nitrogen atom to which they are attached, an N-substituted piperazine ring of formula (X):

(X)

wherein $R^{10}$ is $C_1$–$C_6$ alkyl, phenyl $C_1$–$C_4$ alkyl, naphthyl $C_1$–$C_4$ alkyl, pyridyl $C_1$–$C_4$ alkyl, phenoxy $C_2$–$C_6$ alkyl, pyrrolidinylcarbonyl $C_1$–$C_4$ alkyl, in which the phenyl, phenoxy and naphthyl moieties are unsubstituted or mono- to tri-substituted with halogen, $C_1$–$C_6$ alkyl, halo $C_1$–$C_6$ alkyl, $C_1$–$C_6$ alkoxy, $C_1$–$C_6$ alkoxycarbonyl or phenyl; or pharmacologically acceptable salt thereof.

6. A gastrointestinal prokinetic composition which comprises as an active ingredient a compound defined in any one of claims 1–5 or a pharmacologically acceptable salt thereof in admixture with a pharmaceutically acceptable additive.

7. A gastrointestinal prokinetic agent for the treatment of digestive tract disorders derived from chronic gastritis, post-gastrectomy and peptic ulcer, which comprises an effective amount of a compound as defined in any one of claims 1–5 or a pharmacologically acceptable salt thereof.

8. A gastrointestinal prokinetic agent for the treatment for digestive tract disorders derived from delayed emptying of the gastric content due to diabetes mellitus, which comprises an effective amount of a compound as defined in any one of claims 1–5 or a pharmacologically acceptable salt thereof.

9. A gastrointestinal prokinetic agent for the treatment of digestive tract diseases including reflux esophagitis, irritable bowl syndrome and spurious ileus, which comprises an effective mount of a compound as defined in any one of claims 1–5 or a pharmacologically acceptable salt thereof.

* * * * *

UNITED STATES PATENT AND TRADEMARK OFFICE
CERTIFICATE OF CORRECTION

PATENT NO. : 5,736,550
DATED : April 7, 1998
INVENTOR(S) : Haruhiko KIKUCHI, et al.

It is certified that error appears in the above-identified patent and that said Letters Patent is hereby corrected as shown below:

Claim 1, Column 103, line 67, "a formulae" should read --the formulae--.
Column 104, line 46, "is each" should read --are each--.

Claim 4, Column 106, line 48, "$NR^{15}$" should read --$NR^{13}$--.

Claim 5, Column 107, line 4, "phenyl, $C_1$-$C_4$ alkyl" should read --phenyl $C_1$-$C_4$ alkyl--.

Claim 9, Column 108, line 19, "mount" should read --amount--.

Signed and Sealed this

Twenty-seventh Day of October, 1998

Attest:

BRUCE LEHMAN

*Attesting Officer*     *Commissioner of Patents and Trademarks*